(12) United States Patent
Dong et al.

(10) Patent No.: US 12,029,790 B2
(45) Date of Patent: Jul. 9, 2024

(54) BIOMIMETIC NANOMATERIALS AND USES THEREOF

(71) Applicant: Ohio State Innovation Foundation, Columbus, OH (US)

(72) Inventors: Yizhou Dong, Dublin, OH (US); Xinfu Zhang, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 845 days.

(21) Appl. No.: 16/635,786

(22) PCT Filed: Jul. 31, 2018

(86) PCT No.: PCT/US2018/044567
§ 371 (c)(1),
(2) Date: Jan. 31, 2020

(87) PCT Pub. No.: WO2019/027999
PCT Pub. Date: Feb. 7, 2019

(65) Prior Publication Data
US 2021/0069336 A1    Mar. 11, 2021

Related U.S. Application Data

(60) Provisional application No. 62/546,106, filed on Aug. 16, 2017, provisional application No. 62/539,001, filed on Jul. 31, 2017.

(51) Int. Cl.
| | |
|---|---|
| *A61K 47/54* | (2017.01) |
| *A61K 31/7105* | (2006.01) |
| *A61K 47/55* | (2017.01) |
| *A61K 47/69* | (2017.01) |
| *C07C 235/12* | (2006.01) |
| *C07C 401/00* | (2006.01) |
| *C07C 403/12* | (2006.01) |
| *C07F 9/09* | (2006.01) |
| *C07F 9/6509* | (2006.01) |

(52) U.S. Cl.
CPC ........ *A61K 47/543* (2017.08); *A61K 31/7105* (2013.01); *A61K 47/544* (2017.08); *A61K 47/549* (2017.08); *A61K 47/551* (2017.08); *A61K 47/6929* (2017.08); *C07C 235/12* (2013.01); *C07C 401/00* (2013.01); *C07F 9/09* (2013.01); *C07F 9/091* (2013.01); *C07F 9/650952* (2013.01); *C07C 403/12* (2013.01); *C07C 2601/14* (2017.05); *C07C 2601/16* (2017.05); *C07C 2602/14* (2017.05)

(58) Field of Classification Search
CPC .............. A61K 31/7105; A61K 47/543; A61K 47/544; A61K 47/549; A61K 47/551; A61K 47/6911; A61K 47/6929; C07C 217/08; C07C 229/16; C07C 235/12; C07C 2601/14; C07C 2601/16; C07C 2602/14; C07C 401/00; C07C 403/12; C07D 213/80; C07D 213/82; C07D 307/62; C07D 417/06; C07D 475/04; C07D 475/14; C07D 495/04; C07F 9/09; C07F 9/091; C07F 9/650952; C07H 15/04; C07H 15/26; G03G 5/0525

See application file for complete search history.

(56) References Cited

U.S. PATENT DOCUMENTS

| | | |
|---|---|---|
| 2014/0378532 A1 | 12/2014 | Russo et al. |
| 2015/0157721 A1 | 6/2015 | Wu |
| 2019/0099493 A1* | 4/2019 | Manoharan ............ C07H 21/02 |

FOREIGN PATENT DOCUMENTS

| | | | | |
|---|---|---|---|---|
| WO | 1991/014693 A1 | 10/1991 | | |
| WO | WO-9114693 A | * 10/1991 | ................ C07F 9/11 |
| WO | WO-9623526 A2 | * 8/1996 | ......... A61K 49/0002 |
| WO | WO-2010129709 A1 | * 11/2010 | ............. A61K 47/22 |
| WO | WO-2014106856 A1 | * 7/2014 | ............ A61K 31/166 |

OTHER PUBLICATIONS

Ren et al. Tetrahedron Letters 42 (2001) 1007-1010. (Year: 2010).*
European Patent Office. Extended European Search Report. Issued on Oct. 7, 2021, in Application No. EP 18842065.7. 17 pages.
Altschul, Stephen F., et al. "Basic local alignment search tool." Journal of molecular biology 215.3 (1990): 403-410.
Altschul, Stephen F., et al. "Gapped BLAST and PSI-BLAST: a new generation of protein database search programs." Nucleic acids research 25.17 (1997): 3389-3402.
Beaucage, S. L., and M. H. Caruthers. "Deoxynucleoside phosphoramidites-a new class of key intermediates for deoxypolynucleotide synthesis." Tetrahedron Letters 22.20 (1981): 1859-1862.
Boshart, Michael, et al. "A very strong enhancer is located upstream of an immediate early gene of human cytomegalovirus." cell 41.2 (1985): 521-530.
Henikoff, Steven, and Jorja G. Henikoff. "Amino acid substitution matrices from protein blocks." Proceedings of the National Academy of Sciences 89.22 (1992): 10915-10919.
Karlin, Samuel, and Stephen F. Altschul. "Applications and statistics for multiple high-scoring segments in molecular sequences." Proceedings of the National Academy of Sciences 90.12 (1993): 5873-5877.
Matteucci, Mark Douglas, and M. Ho Caruthers. "Synthesis of deoxyoligonucleotides on a polymer support." Journal of the American Chemical Society 103.11 (1981): 3185-3191.

(Continued)

*Primary Examiner* — Janet L Epps-Smith
(74) *Attorney, Agent, or Firm* — Meunier Carlin & Curfman LLC

(57) ABSTRACT

The present disclosure relates to biomimetic nanomaterials, compounds, compositions, and methods for delivery of therapeutic, diagnostic, or prophylactic agents (for example, a nucleic acid).

9 Claims, 2 Drawing Sheets

(56) References Cited

OTHER PUBLICATIONS

O'hare, K., C. Benoist, and R. Breathnach. "Transformation of mouse fibroblasts to methotrexate resistance by a recombinant plasmid expressing a prokaryotic dihydrofolate reductase." Proceedings of the National Academy of Sciences 78.3 (1981): 1527-1531.

Takebe, Yutaka, et al. "SR alpha promoter: an efficient and versatile mammalian cDNA expression system composed of the simian virus 40 early promoter and the R-U5 segment of human T-cell leukemia virus type 1 long terminal repeat." Molecular and cellular biology 8.1 (1988): 466-472.

International Preliminary Report on Patentability issued for Application No. PCT/US2018/044567 dated Feb. 13, 2020.

Communication pursuant to Article 94(3)EPC, issue for Application No. EP 18842065.7, dated Sep. 23, 2022.

European Patent Office. Communication pursuant to Rule 164(1) EPC, dated Jul. 2, 2021 in Application No. EP 18842065.7. 20 pages.

Ren, Tan, Guisheng Zhang, and Dexi Liu. "Synthesis of galactosyl compounds for targeted gene delivery." Bioorganic & medicinal chemistry 9.11 (2001): 2969-2978.

Ren, Tan, Guisheng Zhang, and Dexi Liu. "Synthesis of bifunctional cationic compound for gene delivery." Tetrahedron Letters 42.6 (2001): 1007-1010.

International Search Report and Written Opinion issued by the International Searching Authority (ISA/US) in PCT Application No. PCT/US2018/044567 dated Dec. 3, 2018. 11 pages.

\* cited by examiner

BIOMIMETIC NANOMATERIALS AND USES THEREOF

CROSS-REFERENCE TO RELATED APPLICATIONS

This application is a national stage application filed under 35 U.S.C. § 371 of PCT/US2018/044567 filed Jul. 31, 2018, which claims the benefit of U.S. Provisional Patent Application Ser. No. 62/539,001 filed Jul. 31, 2017, and U.S. Provisional Patent Application Ser. No. 62/546,106 filed Aug. 16, 2017, each of which is expressly incorporated herein by reference.

STATEMENT REGARDING FEDERALLY FUNDED RESEARCH

This invention was made with Government Support under Grant No. 1?c35GM119679 awarded by the National Institutes of Health. The Government has certain rights to the invention.

FIELD

The present disclosure relates to biomimetic nanomaterials, compounds, compositions, and methods for delivery of therapeutic, diagnostic, or prophylactic agents (for example, a nucleic acid).

BACKGROUND

Messenger RNA (mRNA) based therapeutics have shown great promise for expressing functional antibodies and proteins. Clinical studies have explored mRNA for use as vaccines through local administration of naked mRNA or mRNA-transfected dendritic cells in order to induce antigen-specific immune responses. Recently, extensive efforts have been devoted to achieving the systemic delivery of mRNA using liposomes, polymeric nanoparticles, and mRNA-protein complexes. Efficient delivery of mRNA is a key step and challenge for the application of mRNA therapeutics. Despite promising data from ongoing clinical trials, the clinical use of mRNA requires the discovery and development of more efficient delivery systems.

The compounds, compositions, and methods disclosed herein address these and other needs.

SUMMARY

The present disclosure provides new biomimetic compounds, nanomaterials, and uses thereof. Also provided are compositions including a compound of the invention and an agent (e.g., an mRNA). The present disclosure also provides methods using the compositions for delivering an agent to a subject. These biomimetic nanomaterials comprising carbohydrate, phosphate, or vitamin groups are used in applications such as gene therapy and drug delivery. These compounds were designed and synthesized with diverse carbohydrate, phosphate, or vitamin heads and tunable lipid tails. These materials show high delivery efficiency of mRNA in multiple cell lines.

In one aspect, disclosed herein is a compound of Formula A:

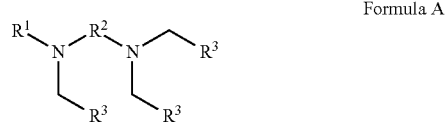

Formula A or a salt thereof, wherein:

$R^1$ is an alkyl or ether linker, wherein the alkyl or ether linker is substituted with a carbohydrate moiety, a phosphate moiety, or a vitamin moiety;

$R^2$ is alkyl, cycloalkyl, heterocycloalkyl, alkylheterocycloalkyl, amide, alkylamide, ether, alkylether,

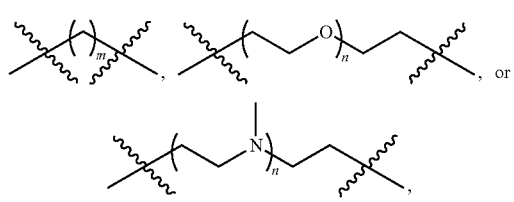

wherein m is an integer from 1 to 20, wherein n is an integer from 1 to 3; and each $R^3$ is independently selected from alkyl, alkenyl, alkynyl, ester, or alkylester.

In one aspect, disclosed herein is a compound of Formula I, II, III, IV, V, VI, VII, VIII, IX, or X:

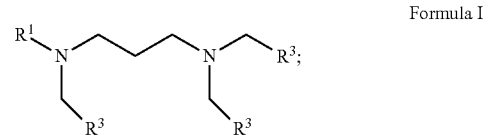

Formula I

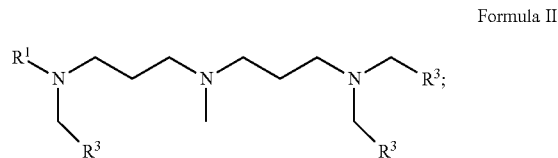

Formula II

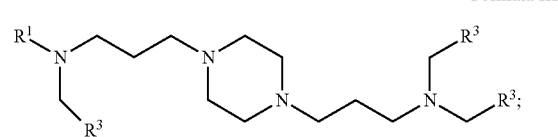

Formula III

Formula IV

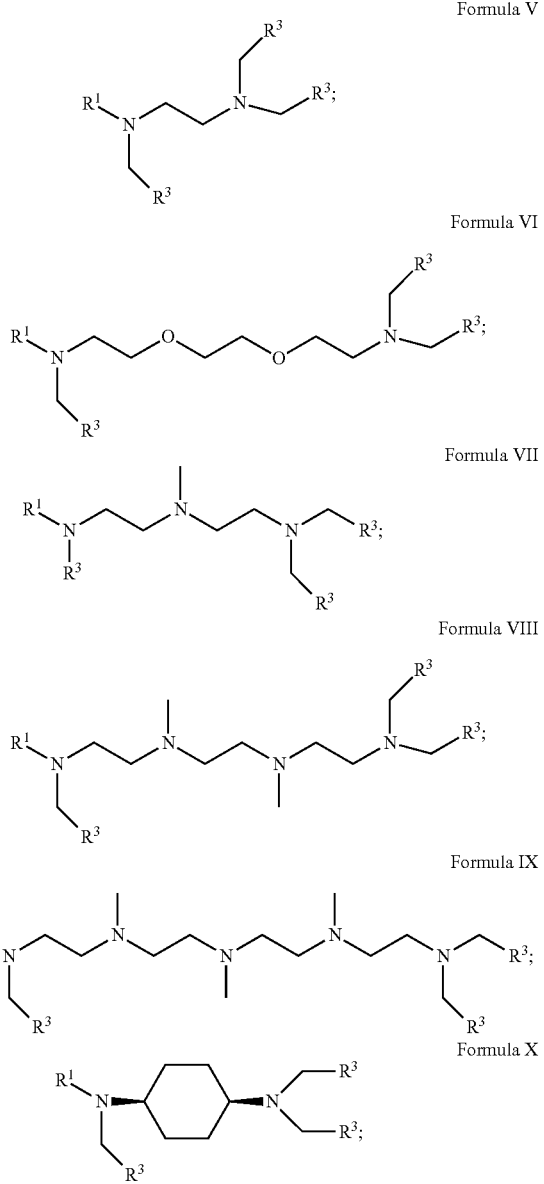

Formula V
Formula VI
Formula VII
Formula VIII
Formula IX
Formula X or a salt thereof, wherein:
R¹ is an alkyl or ether linker, wherein the alkyl or ether linker is substituted with a carbohydrate moiety, a phosphate moiety, or a vitamin moiety; and
each $R^3$ is independently selected from alkyl, alkenyl, alkynyl, ester, or alkylester.

In one aspect, the disclosure provides a nanoparticle comprising:
a compound of Formula A, I, II, III, IV, V, VI, VII, VIII, IX, or X;
a non-cationic lipid;
a polyethylene glycol-lipid; and
a sterol.

In one aspect, provided herein is a method for the delivery of an agent (for example, a polynucleotide) into a cell comprising;
introducing into the cell a composition comprising;
i) a nanoparticle, comprising;
a compound of Formula A, I, II, III, IV, V, VI, VII, VIII, IX, or X;
a non-cationic lipid;
a polyethylene glycol-lipid;
a sterol; and
ii) an agent.

In some embodiments, the agent is a therapeutic agent, diagnostic agent, or prophylactic agent. In some embodiments, the agent is a nucleic acid. In some embodiments, the agent is a polynucleotide (for example, an mRNA).

In some embodiments, provided herein are methods for the delivery of nucleic acid. In some embodiments, provided herein are methods for the delivery of polynucleotides.

BRIEF DESCRIPTION OF THE DRAWINGS

The accompanying figures, which are incorporated in and constitute a part of this specification, illustrate several aspects described below.

DETAILED DESCRIPTION

Figure 1:
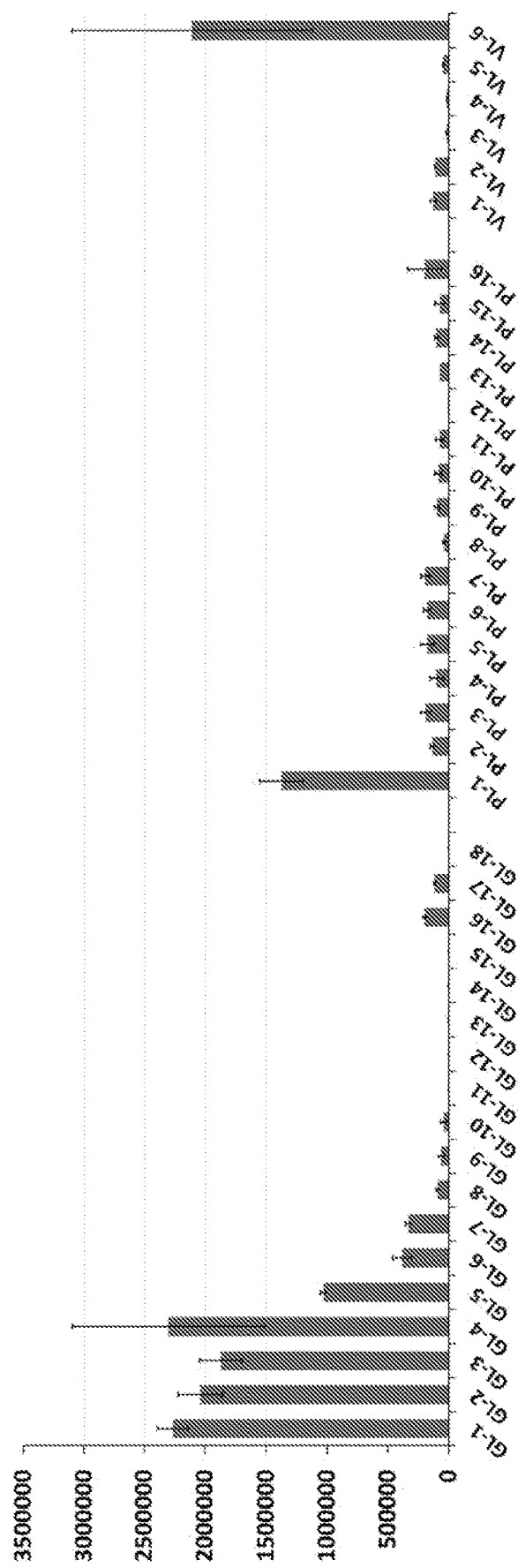
FIG. 1 shows in vitro expression of luciferase in Hep3B cells with formulations based on biomimetic nanomaterials.
Figure 2:
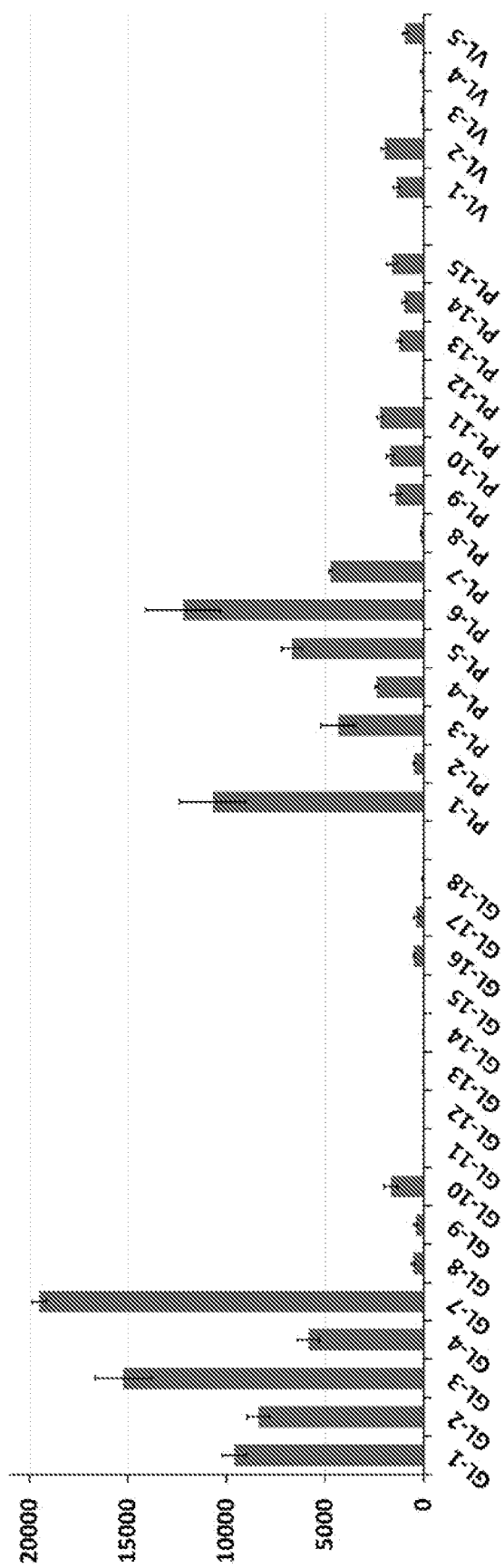
FIG. 2 shows in vitro expression of luciferase in Jurkat cells with formulations based on biomimetic nanomaterials.

The present disclosure provides new biomimetic compounds, nanomaterials, and uses thereof. Also provided are compositions including a compound of the invention and an agent (e.g., an mRNA). The present disclosure also provides methods using the compositions for delivering an agent to a subject. These biomimetic nanomaterials comprising carbohydrate, phosphate, or vitamin groups are used in applications such as gene therapy and drug delivery. These compounds were designed and synthesized with diverse carbohydrate, phosphate, or vitamin heads and tunable lipid tails. These materials show high delivery efficiency of mRNA in multiple cell lines.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed. The following definitions are provided for the full understanding of terms used in this specification.

Terminology

As used herein, the article "a," "an," and "the" means "at least one," unless the context in which the article is used clearly indicates otherwise.

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.*, 22:1859-1862 (1981), or by the triester method according to Matteucci, et al., *J. Am. Chem. Soc.*, 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, *Biochemistry*, Third Ed., (1988), incorporated herein by reference for all purposes.

The term "polynucleotide" refers to a single or double stranded polymer composed of nucleotide monomers. In some embodiments, the polynucleotide is composed of nucleotide monomers of generally greater than 100 nucleotides in length and up to about 8,000 or more nucleotides in length.

The term "polypeptide" refers to a compound made up of a single chain of D- or L-amino acids or a mixture of D- and L-amino acids joined by peptide bonds.

The term "complementary" refers to the topological compatibility or matching together of interacting surfaces of a probe molecule and its target. Thus, the target and its probe can be described as complementary, and furthermore, the contact surface characteristics are complementary to each other.

The term "hybridization" refers to a process of establishing a non-covalent, sequence-specific interaction between two or more complementary strands of nucleic acids into a single hybrid, which in the case of two strands is referred to as a duplex.

The term "anneal" refers to the process by which a single-stranded nucleic acid sequence pairs by hydrogen bonds to a complementary sequence, forming a double-stranded nucleic acid sequence, including the reformation (renaturation) of complementary strands that were separated by heat (thermally denatured).

The term "melting" refers to the denaturation of a double-stranded nucleic acid sequence due to high temperatures, resulting in the separation of the double strand into two single strands by breaking the hydrogen bonds between the strands.

The term "target" refers to a molecule that has an affinity for a given probe. Targets may be naturally-occurring or man-made molecules. Also, they can be employed in their unaltered state or as aggregates with other species.

The term "promoter" or "regulatory element" refers to a region or sequence determinants located upstream or downstream from the start of transcription and which are involved in recognition and binding of RNA polymerase and other proteins to initiate transcription. Promoters need not be of bacterial origin, for example, promoters derived from viruses or from other organisms can be used in the compositions, systems, or methods described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, Gene Expression Technology: Methods in Enzymology 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell*, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It is appreciated by those skilled in the art that the design of the expression vector can depend on such factors as the choice of the host cell to be transformed, the level of expression desired, etc.

The term "recombinant" refers to a human manipulated nucleic acid (e.g. polynucleotide) or a copy or complement of a human manipulated nucleic acid (e.g. polynucleotide), or if in reference to a protein (i.e, a "recombinant protein"), a protein encoded by a recombinant nucleic acid (e.g. polynucleotide). In embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature. For instance, human manipulated restriction sites or plasmid vector sequences may flank or separate the promoter from the second nucleic acid (e.g. polynucleotide). One of skill will recognize that nucleic acids (e.g. polynucleotides) can be manipulated in many ways and are not limited to the examples above.

The term "expression cassette" refers to a nucleic acid construct, which when introduced into a host cell, results in transcription and/or translation of a RNA or polypeptide, respectively. In embodiments, an expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or *Current Protocols in Molecular Biology* Volumes 1-3, John Wiley & Sons, Inc. (1994-1998)). In some embodiments, an expression cassette comprising a terminator (or termination sequence) operably linked to a second nucleic acid (e.g. polynucleotide) may include a terminator that is heterologous to the second nucleic acid (e.g. polynucleotide) as the result of human manipulation. In some embodiments, the expression cassette comprises a promoter operably linked to a second nucleic acid (e.g. polynucleotide) and a terminator operably linked to the second nucleic acid (e.g. polynucleotide) as the result of human manipulation. In some embodiments, the expression cassette comprises an endogenous promoter. In some embodiments, the expression cassette comprises an endogenous terminator. In some embodiments, the expression cassette comprises a synthetic (or non-natural) promoter. In some embodiments, the expression cassette comprises a synthetic (or non-natural) terminator.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The phrase "codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Such optimization includes replacing at least one, or more than one, or a significant number, of codons with one or more codons that are more frequently used in the genes of that selected organism.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

The term "nucleobase" refers to the part of a nucleotide that bears the Watson/Crick base-pairing functionality. The most common naturally-occurring nucleobases, adenine (A), guanine (G), uracil (U), cytosine (C), and thymine (T) bear the hydrogen-bonding functionality that binds one nucleic acid strand to another in a sequence specific manner.

As used throughout, by a "subject" (or a "host") is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms with a structural formula containing at least one carbon-carbon double bond. Asymmetric structures such as ($Z^1Z^2$)C=C($Z^3Z^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C═O.

The terms "amine" or "amino" as used herein are represented by the formula —$NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" or "carboxyl" group as used herein is represented by the formula —C(O)O⁻.

The term "ester" as used herein is represented by the formula —OC(O)$Z^1$ or —C(O)O$Z^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —$NO_2$.

The term "silyl" as used herein is represented by the formula —$SiZ^1Z^2$ where $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —$S(O)_2Z^1$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH$—.

The term "phosphonyl" is used herein to refer to the phospho-oxo group represented by the formula —$P(O)(OZ^1)_2$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "thiol" as used herein is represented by the formula —SH.

The term "thio" as used herein is represented by the formula —S—.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxyl group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compounds

In one aspect, disclosed herein is a compound of Formula A:

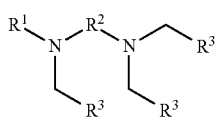

Formula A or a salt thereof, wherein:

R¹ is an alkyl or ether linker, wherein the alkyl or ether linker is substituted with a carbohydrate moiety, a phosphate moiety, or a vitamin moiety;

R² is alkyl, cycloalkyl, heterocycloalkyl, alkylheterocycloalkyl, amide, alkylamide, ether, alkylether,

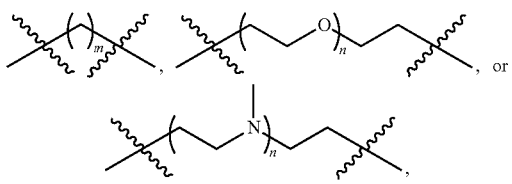

wherein m is an integer from 1 to 20,
wherein n is an integer from 1 to 3; and
each R³ is independently selected from alkyl, alkenyl, alkynyl, ester, or alkylester.

In one aspect, disclosed herein is a compound of Formula I, II, III, IV, V, VI, VII, VIII, IX, or X:

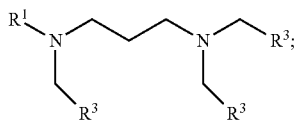

Formula I

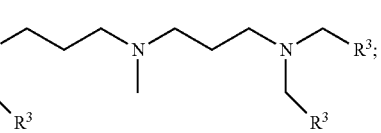

Formula II

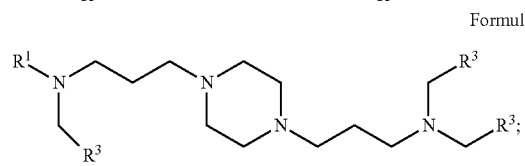

Formula III

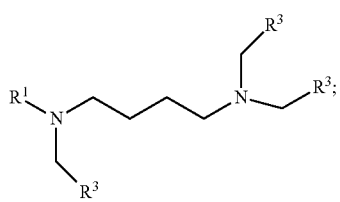

Formula IV

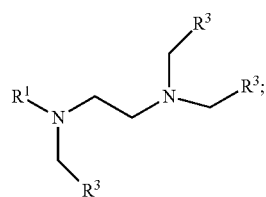

Formula V

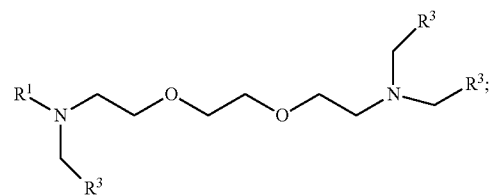

Formula VI

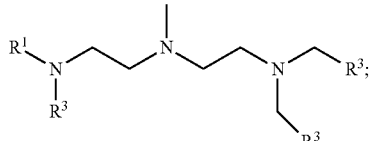

Formula VII

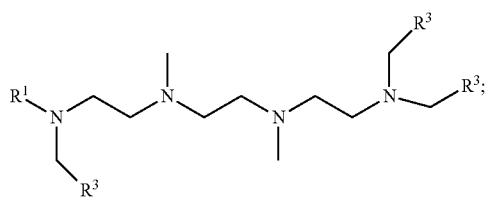

Formula VIII

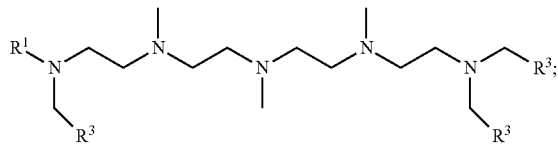

Formula IX

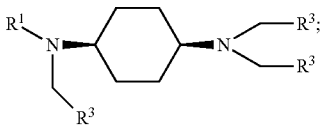

Formula X or a salt thereof, wherein:

R¹ is an alkyl or ether linker, wherein the alkyl or ether linker is substituted with a carbohydrate moiety, a phosphate moiety, or a vitamin moiety; and each R³ is independently selected from alkyl, alkenyl, alkynyl, ester, or alkylester.

In one aspect, disclosed herein is a compound of Formula I:

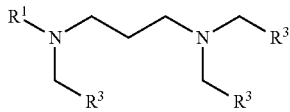

Formula I or a salt thereof, wherein:

R¹ is an alkyl or ether linker, wherein the alkyl or ether linker is substituted with a carbohydrate moiety, a phosphate moiety, or a vitamin moiety; and each R³ is independently selected from alkyl, alkenyl, alkynyl, ester, or alkylester.

In one aspect, disclosed herein is a compound of Formula II:

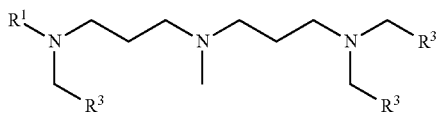

Formula II or a salt thereof, wherein:

R¹ is an alkyl or ether linker, wherein the alkyl or ether linker is substituted with a carbohydrate moiety, a phosphate moiety, or a vitamin moiety; and each R³ is independently selected from alkyl, alkenyl, alkynyl, ester, or alkylester.

In another aspect, the disclosure provides a compound of Formula III:

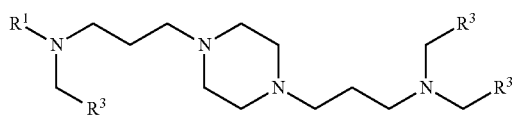

Formula III or a salt thereof, wherein:

R¹ is an alkyl or ether linker, wherein the alkyl or ether linker is substituted with a carbohydrate moiety, a phosphate moiety, or a vitamin moiety; and each R³ is independently selected from alkyl, alkenyl, alkynyl, ester, or alkylester.

In another aspect, the disclosure provides a compound of Formula IV:

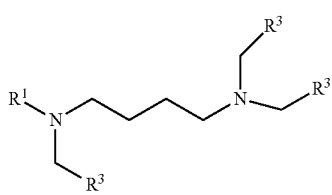

Formula IV or a salt thereof, wherein:

R¹ is an alkyl or ether linker, wherein the alkyl or ether linker is substituted with a carbohydrate moiety, a phosphate moiety, or a vitamin moiety; and each R³ is independently selected from alkyl, alkenyl, alkynyl, ester, or alkylester.

In another aspect, the disclosure provides a compound of Formula V:

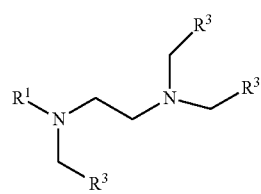

Formula V or a salt thereof, wherein:

R¹ is an alkyl or ether linker, wherein the alkyl or ether linker is substituted with a carbohydrate moiety, a phosphate moiety, or a vitamin moiety; and each R³ is independently selected from alkyl, alkenyl, alkynyl, ester, or alkylester.

In another aspect, the disclosure provides a compound of Formula VI:

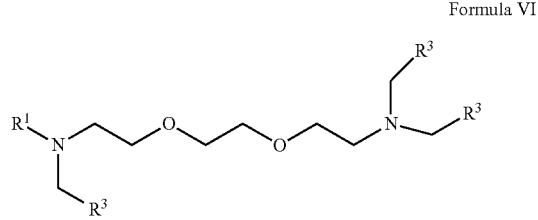

Formula VI or a salt thereof, wherein:

R¹ is an alkyl or ether linker, wherein the alkyl or ether linker is substituted with a carbohydrate moiety, a phosphate moiety, or a vitamin moiety; and each R³ is independently selected from alkyl, alkenyl, alkynyl, ester, or alkylester.

In another aspect, the disclosure provides a compound of Formula VII:

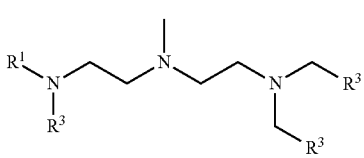

Formula VII or a salt thereof, wherein:

R¹ is an alkyl or ether linker, wherein the alkyl or ether linker is substituted with a carbohydrate moiety, a phosphate moiety, or a vitamin moiety; and each R³ is independently selected from alkyl, alkenyl, alkynyl, ester, or alkylester.

In another aspect, the disclosure provides a compound of Formula VIII:

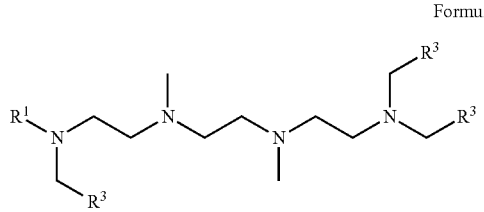

Formula VIII or a salt thereof, wherein:
R¹ is an alkyl or ether linker, wherein the alkyl or ether linker is substituted with a carbohydrate moiety, a phosphate moiety, or a vitamin moiety; and
each R³ is independently selected from alkyl, alkenyl, alkynyl, ester, or alkylester.

In another aspect, the disclosure provides a compound of Formula IX:

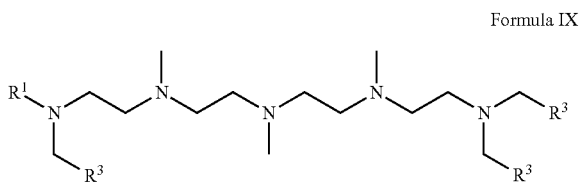

Formula IX or a salt thereof, wherein:
R¹ is an alkyl or ether linker, wherein the alkyl or ether linker is substituted with a carbohydrate moiety, a phosphate moiety, or a vitamin moiety; and
each R³ is independently selected from alkyl, alkenyl, alkynyl, ester, or alkylester.

In another aspect, the disclosure provides a compound of Formula X:

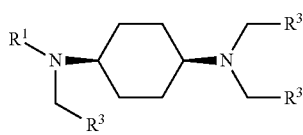

Formula X or a salt thereof, wherein:
R¹ is an alkyl or ether linker, wherein the alkyl or ether linker is substituted with a carbohydrate moiety, a phosphate moiety, or a vitamin moiety; and
each R³ is independently selected from alkyl, alkenyl, alkynyl, ester, or alkylester.

In one aspect, disclosed herein is a compound of Formula I:

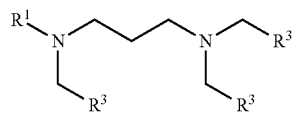

Formula I or a salt thereof, wherein:
R¹ is an alkyl, substituted with a carbohydrate moiety, a phosphate moiety, or a vitamin moiety; and
each R³ is independently selected from alkyl, alkenyl, alkynyl, ester, or alkylester.

In one aspect, disclosed herein is a compound of Formula II:

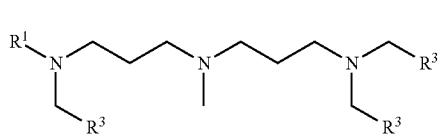

Formula II or a salt thereof, wherein:
R¹ is an alkyl, substituted with a carbohydrate moiety, a phosphate moiety, or a vitamin moiety; and
each R³ is independently selected from alkyl, alkenyl, alkynyl, ester, or alkylester.

In another aspect, the disclosure provides a compound of Formula III:

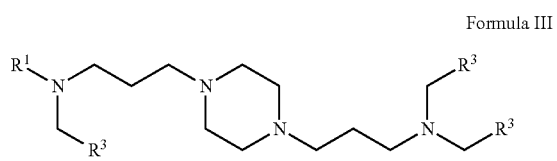

Formula III or a salt thereof, wherein:
R¹ is an alkyl, substituted with a carbohydrate moiety, a phosphate moiety, or a vitamin moiety; and
each R³ is independently selected from alkyl, alkenyl, alkynyl, ester, or alkylester.

In one aspect, disclosed herein is a compound of Formula IV:

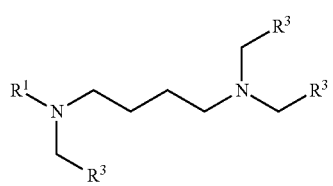

Formula IV or a salt thereof, wherein:
R¹ is an alkyl, substituted with a carbohydrate moiety, a phosphate moiety, or a vitamin moiety; and
each R³ is independently selected from alkyl, alkenyl, alkynyl, ester, or alkylester.

In another aspect, the disclosure provides a compound of Formula V:

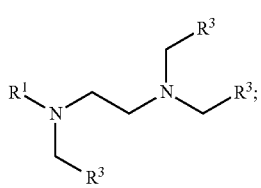

Formula V or a salt thereof, wherein:

$R^1$ is an alkyl, substituted with a carbohydrate moiety, a phosphate moiety, or a vitamin moiety; and each $R^3$ is independently selected from alkyl, alkenyl, alkynyl, ester, or alkylester.

In one aspect, disclosed herein is a compound of Formula VI:

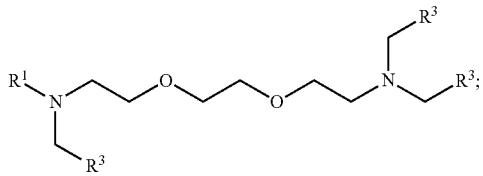

Formula VI or a salt thereof, wherein:

$R^1$ is an alkyl, substituted with a carbohydrate moiety, a phosphate moiety, or a vitamin moiety; and each $R^3$ is independently selected from alkyl, alkenyl, alkynyl, ester, or alkylester.

In one aspect, disclosed herein is a compound of Formula VII:

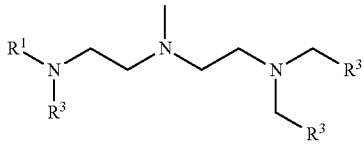

Formula VII or a salt thereof, wherein:

$R^1$ is an alkyl, substituted with a carbohydrate moiety, a phosphate moiety, or a vitamin moiety; and each $R^3$ is independently selected from alkyl, alkenyl, alkynyl, ester, or alkylester.

In one aspect, disclosed herein is a compound of Formula VIII:

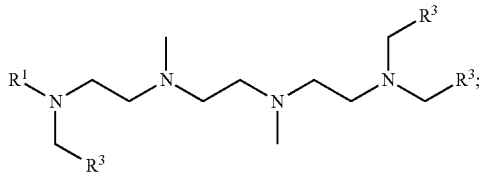

Formula VIII or a salt thereof, wherein:

$R^1$ is an alkyl, substituted with a carbohydrate moiety, a phosphate moiety, or a vitamin moiety; and each $R^3$ is independently selected from alkyl, alkenyl, alkynyl, ester, or alkylester.

In another aspect, the disclosure provides a compound of Formula IX:

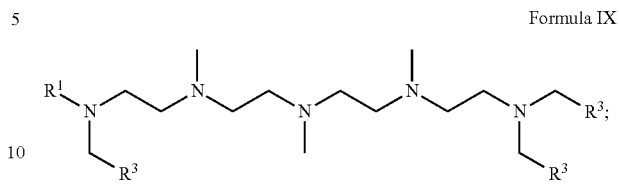

Formula IX or a salt thereof, wherein:

$R^1$ is an alkyl, substituted with a carbohydrate moiety, a phosphate moiety, or a vitamin moiety; and each $R^3$ is independently selected from alkyl, alkenyl, alkynyl, ester, or alkylester.

In one aspect, disclosed herein is a compound of Formula X:

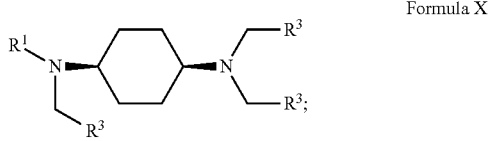

Formula X or a salt thereof, wherein:

$R^1$ is an alkyl, substituted with a carbohydrate moiety, a phosphate moiety, or a vitamin moiety; and each $R^3$ is independently selected from alkyl, alkenyl, alkynyl, ester, or alkylester.

In one aspect, the disclosure provides a compound of Formula A, I, II, III, IV, V, VI, VII, VIII, IX, X, or a salt thereof, wherein:

$R^1$ is an alkyl, substituted with a carbohydrate moiety; and each $R^3$ is independently selected from alkyl, alkenyl, alkynyl, ester, or alkylester.

In one aspect, the disclosure provides a compound of Formula A, I, II, III, IV, V, VI, VII, VIII, IX, X, or a salt thereof, wherein:

$R^1$ is an alkyl, substituted with a phosphate moiety; and each $R^3$ is independently selected from alkyl, alkenyl, alkynyl, ester, or alkylester.

In one aspect, the disclosure provides a compound of Formula A, I, II, III, IV, V, VI, VII, VIII, IX, X, or a salt thereof, wherein:

$R^1$ is an alkyl, substituted with a vitamin moiety; and each $R^3$ is independently selected from alkyl, alkenyl, alkynyl, ester, or alkylester.

In one aspect, the disclosure provides a compound of Formula A, I, II, III, IV, V, VI, VII, VIII, IX, X, or a salt thereof, wherein:

$R^1$ is a $C_3$-$C_6$ alkyl, substituted with a carbohydrate moiety, a phosphate moiety, or a vitamin moiety; and each $R^3$ is independently selected from alkyl, alkenyl, alkynyl, ester, or alkylester.

In one aspect, the disclosure provides a compound of Formula A, I, II, III, IV, V, VI, VII, VIII, IX, X, or a salt thereof, wherein:

$R^1$ is an alkyl, substituted with a carbohydrate moiety, a phosphate moiety, or a vitamin moiety; and each $R^3$ is independently selected from $C_{7-17}$ alkyl, $C_{7-20}$ alkenyl, or $C_{1-10}$ alkylester, wherein the $C_{1-10}$ alkylester is substituted with an alkyl or alkenyl group.

In one aspect, the disclosure provides a compound of Formula A, I, II, III, IV, V, VI, VII, VIII, IX, X, or a salt thereof, wherein:
$R^1$ is a $C_3$–$C_6$alkyl, substituted with a carbohydrate moiety, a phosphate moiety, or a vitamin moiety; and
each $R^3$ is independently selected from $C_{7-17}$ alkyl, $C_{7-20}$alkenyl, or $C_{1-10}$alkylester, wherein the $C_{1-10}$alkylester is substituted with an alkyl or alkenyl group.

In one aspect, the disclosure provides a compound of Formula A, I, II, III, IV, V, VI, VII, VIII, IX, X, or a salt thereof, wherein:
$R^1$ is an ether linker, substituted with a carbohydrate moiety; and
each $R^3$ is independently selected from alkyl, alkenyl, alkynyl, ester, or alkylester.

In one aspect, the disclosure provides a compound of Formula A, I, II, III, IV, V, VI, VII, VIII, IX, X, or a salt thereof, wherein:
$R^1$ is an ether linker, substituted with a phosphate moiety; and
each $R^3$ is independently selected from alkyl, alkenyl, alkynyl, ester, or alkylester.

In one aspect, the disclosure provides a compound of Formula A, I, II, III, IV, V, VI, VII, VIII, IX, X, or a salt thereof, wherein:
$R^1$ is an ether linker, substituted with a vitamin moiety; and
each $R^3$ is independently selected from alkyl, alkenyl, alkynyl, ester, or alkylester.

In one aspect, the disclosure provides a compound of Formula A, I, II, III, IV, V, VI, VII, VIII, IX, X, or a salt thereof, wherein:
$R^1$ is an ether linker, substituted with a carbohydrate moiety, a phosphate moiety, or a vitamin moiety; and
each $R^3$ is independently selected from $C_{7-17}$ alkyl, $C_{7-20}$alkenyl, or $C_{1-10}$alkylester, wherein the $C_{1-10}$alkylester is substituted with an alkyl or alkenyl group.

For Formula A in the compounds above, $R^2$ is alkyl, cycloalkyl, heterocycloalkyl, alkylheterocycloalkyl, amide, alkylamide, ether, alkylether,

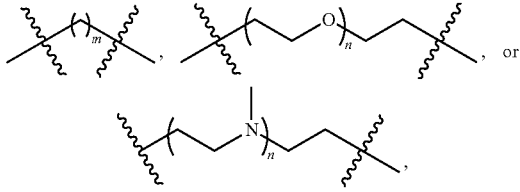
, or wherein m is an integer from 1 to 20; and
wherein n is an integer from 1 to 3.

In some embodiments, $R^1$ is an alkyl substituted with a carbohydrate moiety, a phosphate moiety, or a vitamin moiety. In some embodiments, $R^1$ is a $C_1$-$C_6$alkyl substituted with a carbohydrate moiety, a phosphate moiety, or a vitamin moiety. In some embodiments, $R^1$ is a $C_3$-$C_6$alkyl substituted with a carbohydrate moiety, a phosphate moiety, or a vitamin moiety.

In some embodiments, $R^1$ is an alkyl substituted with a carbohydrate moiety. In some embodiments, $R^1$ is a $C_1$-$C_6$alkyl substituted with a carbohydrate moiety. In some embodiments, $R^1$ is a $C_3$alkyl substituted with a carbohydrate moiety.

In some embodiments, $R^1$ is an ether linker substituted with a carbohydrate moiety, a phosphate moiety, or a vitamin moiety.

In some embodiments, $R^1$ is an ether linker substituted with a carbohydrate moiety.

Various alkyl and ether linkers can be used to link the carbohydrate moiety, the phosphate moiety, or the vitamin moiety to the lipid tail. Examples of linkers can include:

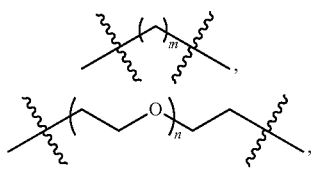

wherein m is an integer from 1 to 20; and
wherein n is an integer from 1 to 3.

Various starting compounds can be used for the synthesis of the alkyl and ether linkers. For example, compounds used for synthesis can include:

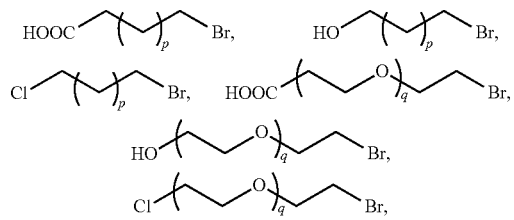

wherein p is an integer from 1 to 20; and
wherein q is an integer from 1 to 3.

In some embodiments, the carbohydrate moiety is selected from beta-D-galactose, beta-D-glucose, beta-D-maltose, beta-D-ribofuranose, or beta-D-galactose pentapivalate.

In some embodiments, the carbohydrate moiety is selected from D-fructose, N-acetyl-glucosamine, D-mannose, D-arabinose, myo-inositol, D-tagatose, D-glucose, D-ribose, D-sorbitol. In some embodiments, the carbohydrate moiety is selected from a monosaccharide, oligosaccharide, polysaccharide, or a derivative thereof.

In some embodiments, the carbohydrate moiety is selected from lactose, lactulose, chitobiose, maltose, cellobiose, nigerose, isomaltose, sophorose, laminaribose, gentiobiose, isomaltulose, 2α-mannobiose, 3α-mannobiose, melibiose, melibiulose, and rutinose. The structures of these carbohydrate moieties are shown below:

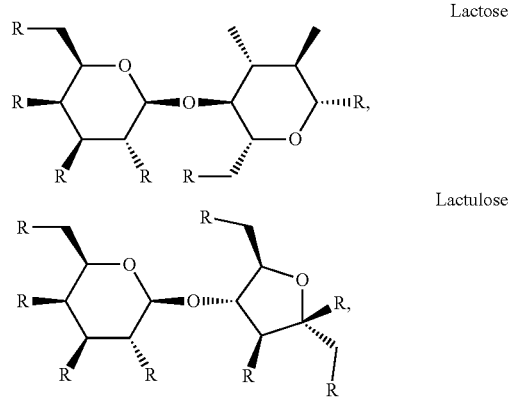

Lactose

Lactulose

-continued

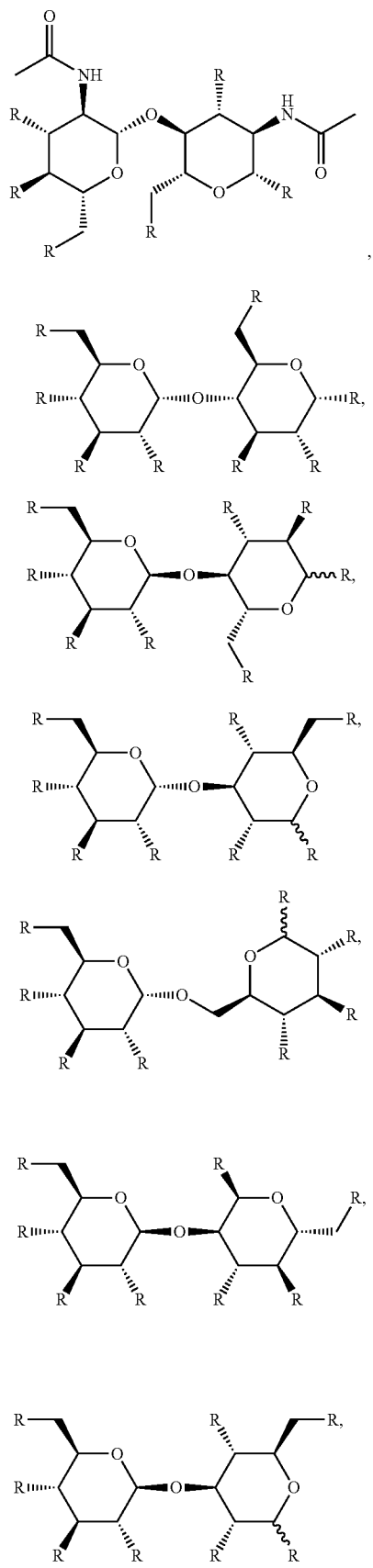

Chitobiose

Maltose

Cellobiose

Nigerose

Isomaltose

Sophorose

Laminaribiose

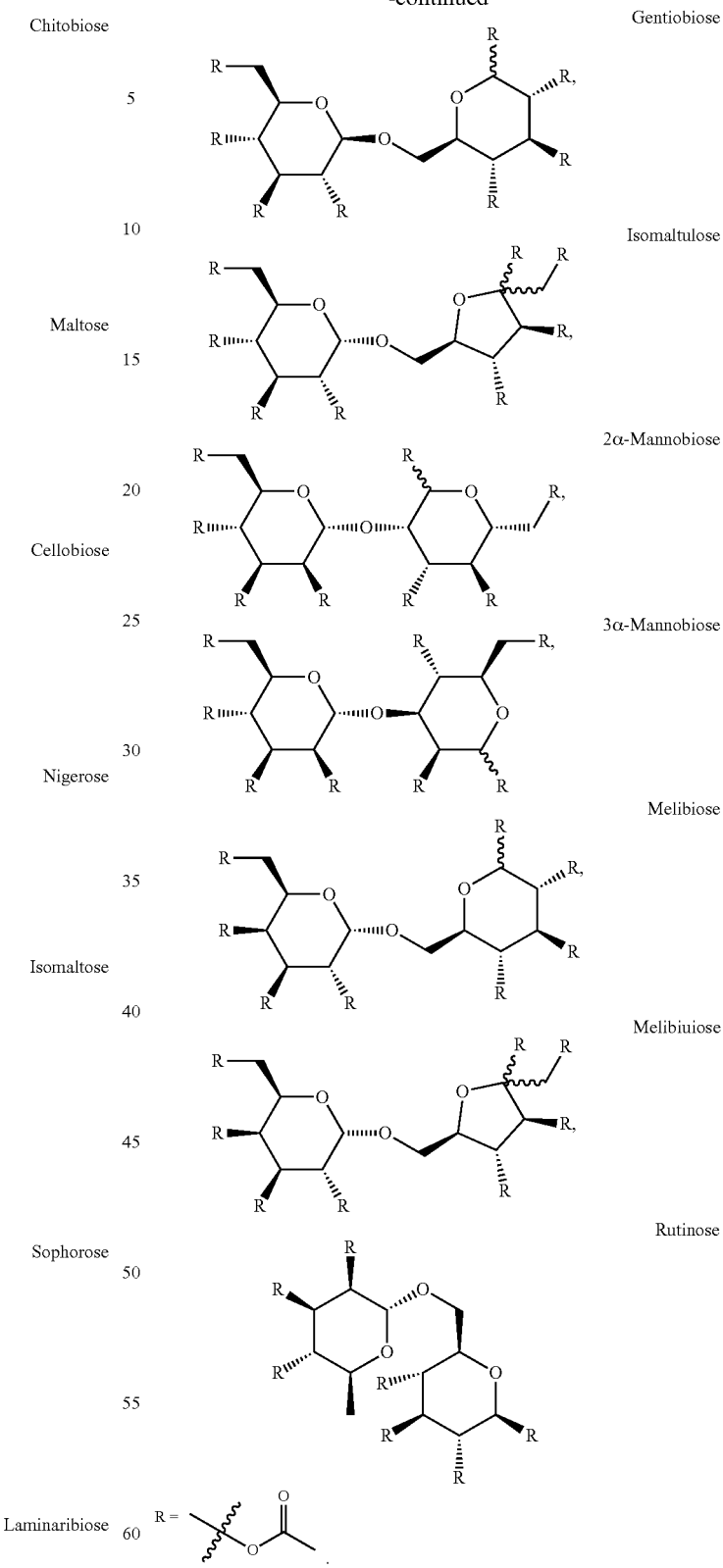

Gentiobiose

Isomaltulose

2α-Mannobiose

3α-Mannobiose

Melibiose

Melibiuiose

Rutinose

In some embodiments, $R^1$ is an alkyl substituted with a phosphate moiety. In some embodiments, $R^1$ is a $C_3$alkyl substituted with a phosphate moiety. In some embodiments, $R^1$ is an ether linker substituted with a phosphate moiety.

In some embodiments, the phosphate moiety has the formula —(O)P(=O)(OR$^4$)(OR$^5$), wherein R$^4$ and R$^5$ are independently selected from alkyl, alkenyl, alkynyl, ester, or alkylester. In some embodiments, R$^4$ and R$^5$ are both alkyl. In some embodiments, R$^4$ and R$^5$ are both ethyl.

In some embodiments, R$^1$ is an alkyl substituted with a vitamin moiety. In some embodiments, R$^1$ is a C$_{5-6}$alkyl substituted with a vitamin moiety. In some embodiments, R$^1$ is an ether linker substituted with a vitamin moiety.

In some embodiments, the vitamin moiety is selected from the group consisting of vitamin A, vitamin B, vitamin C, vitamin D, vitamin E, vitamin K, biotin, folic acid, folate, para-aminobenzoic acid (PABA), and a derivative or salt thereof. In some embodiments, the vitamin moiety is selected from the group consisting of vitamin A (retinol), vitamin B1 (thiamin), vitamin B2 (riboflavin), vitamin B3 (nicotinic acid or nicotinamide), vitamin B5 (pantothenic acid), vitamin B6 (pyridoxal phosphate), vitamin B7 (biotin), vitamin B9 (folic acid), vitamin B12 (cobalamin), vitamin C, vitamin D (cholecalciferol), vitamin E (alpha-tocopherol), and a derivative or salt thereof.

In some embodiments, the vitamin moiety is selected from the following:

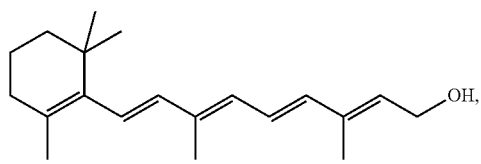

Vitamin A (retinol)

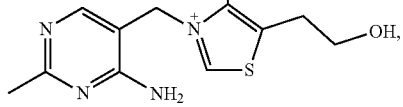

Vitamin B1 (thiamin)

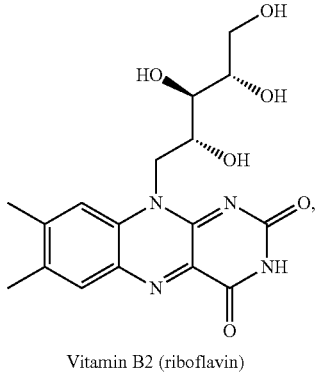

Vitamin B2 (riboflavin)

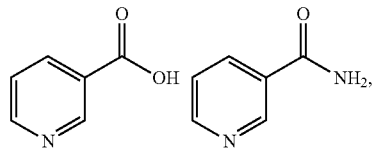

Vitamin B3 (nicotinic acid & nicotineamide)

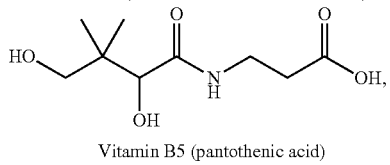

Vitamin B5 (pantothenic acid)

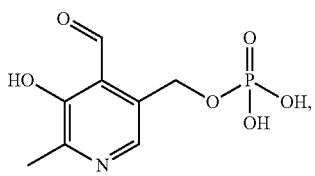

Vitamin B6 (pyridoxal phosphate)

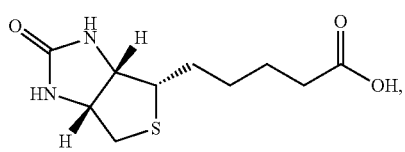

Vitamin B7 (biotin)

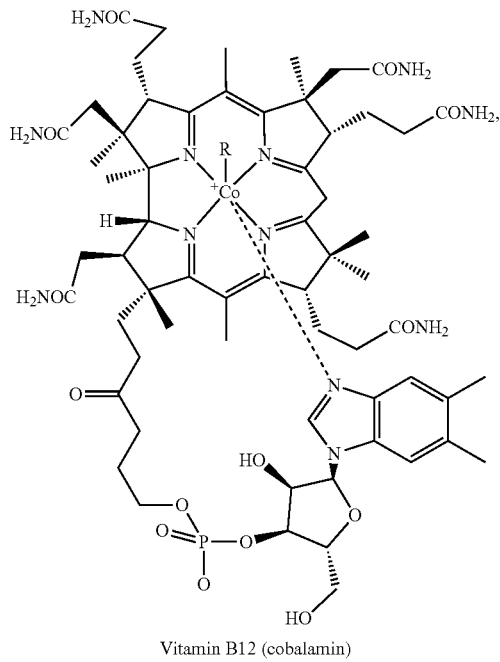

Vitamin B12 (cobalamin)

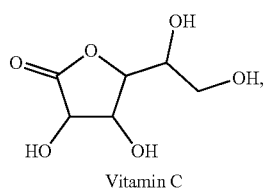

Vitamin C

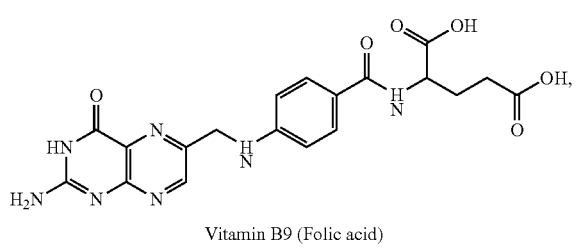

Vitamin B9 (Folic acid)

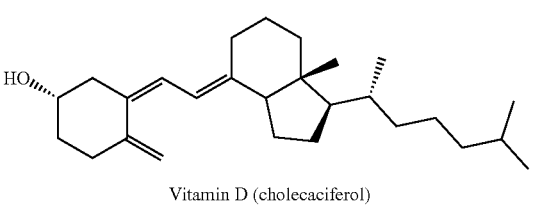

Vitamin D (cholecaciferol)

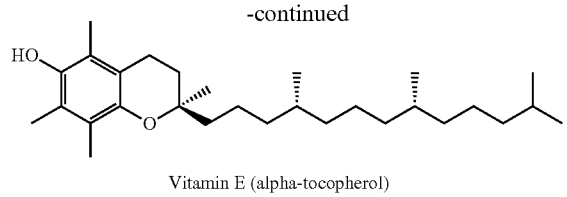

Vitamin E (alpha-tocopherol)

In some embodiments, each $R^3$ is independently selected from alkyl, alkenyl, alkynyl, ester, or alkylester. In some embodiments, each $R^3$ is independently selected from alkyl, alkenyl, or alkylester. In some embodiments, each $R^3$ is independently selected from $C_{7-17}$alkyl, $C_{7-20}$alkenyl, or $C_{1-10}$alkylester, wherein the $C_{1-10}$alkylester is substituted with an alkyl or alkenyl group.

In some embodiments, each $R^3$ is independently selected from an alkyl. In some embodiments, each $R^3$ is independently selected from a $C_{7-17}$alkyl. In some embodiments, each $R^3$ is independently selected from a $C_{9-12}$alkyl. In some embodiments, each $R^3$ is independently selected from a $C_9$alkyl. In some embodiments, each $R^3$ is independently selected from a $C_{10}$alkyl. In some embodiments, each $R^3$ is independently selected from a $C_{11}$alkyl. In some embodiments, each $R^3$ is independently selected from a $C_{12}$alkyl.

In some embodiments, each $R^3$ is independently selected from an alkenyl. In some embodiments, each $R^3$ is independently selected from a $C_{7-20}$alkenyl. In some embodiments, each $R^3$ is independently selected from a $C_9$alkenyl.

In some embodiments, each $R^3$ is independently selected from a alkylester. In some embodiments, each $R^3$ is independently selected from a alkylester, wherein the alkylester is substituted with an alkyl or alkenyl group. In some embodiments, each $R^3$ is independently selected from a $C_{1-10}$alkylester, wherein the $C_{1-10}$alkylester is substituted with an alkyl or alkenyl group. In some embodiments, each $R^3$ is independently selected from a $C_{1-10}$alkylester, wherein the $C_{1-10}$alkylester is substituted with $C_{6-8}$alkyl group. In some embodiments, each $R^3$ is independently selected from a $C_{1-10}$alkylester, wherein the $C_{1-10}$alkylester is substituted with $C_{6-10}$alkenyl group.

In some embodiments, each $R^3$ is independently selected from a linear or branched saturated alkyl chain comprising 7 to 17 carbons. In some embodiments, each $R^3$ is independently selected from

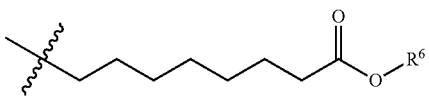

wherein each $R^6$ is independently selected from a linear or branched saturated alkyl chain comprising 4 to 9 carbons.

In some embodiments, the compound is selected from the following:

GL-1

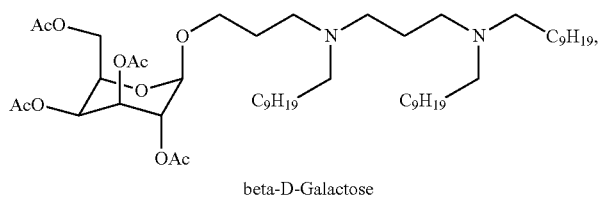

beta-D-Galactose

GL-2

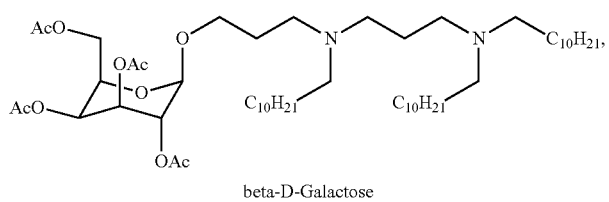

beta-D-Galactose

GL-3

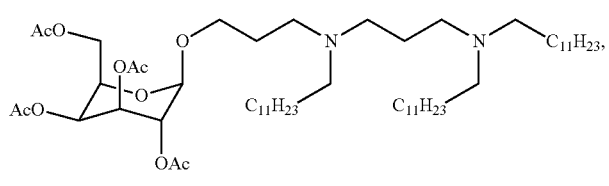

beta-D-Galactose

GL-4

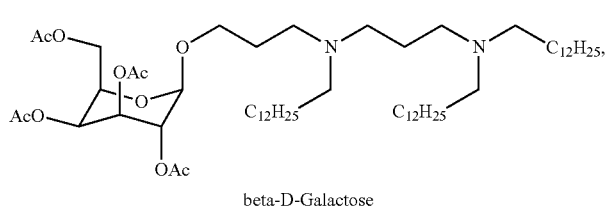

beta-D-Galactose

-continued
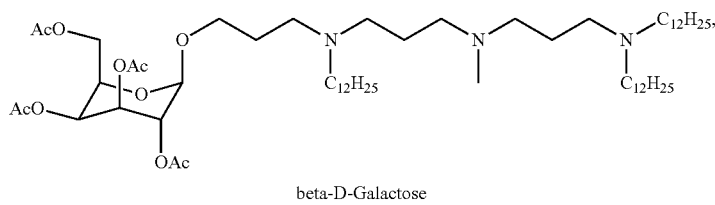
beta-D-Galactose
GL-5
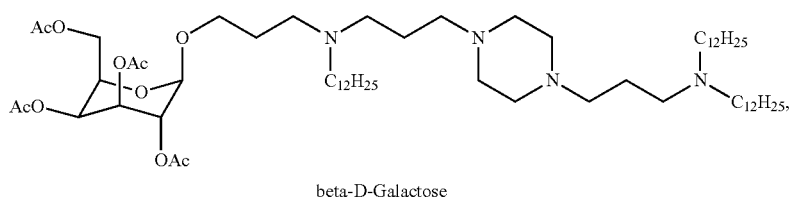
beta-D-Galactose
GL-6
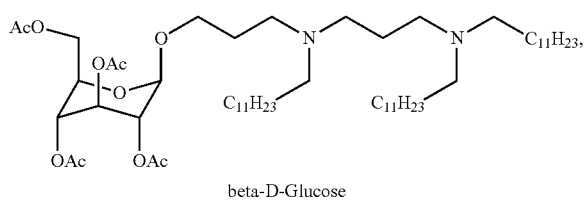
beta-D-Glucose
GL-7
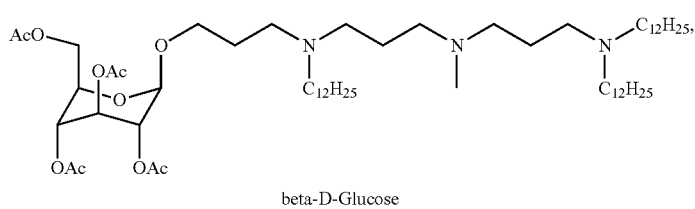
beta-D-Glucose
GL-8
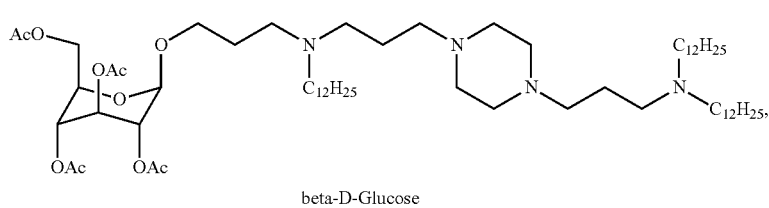
beta-D-Glucose
GL-9
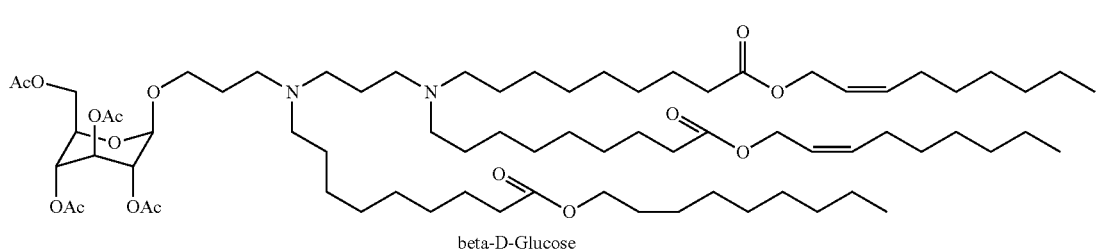
beta-D-Glucose
GL-10
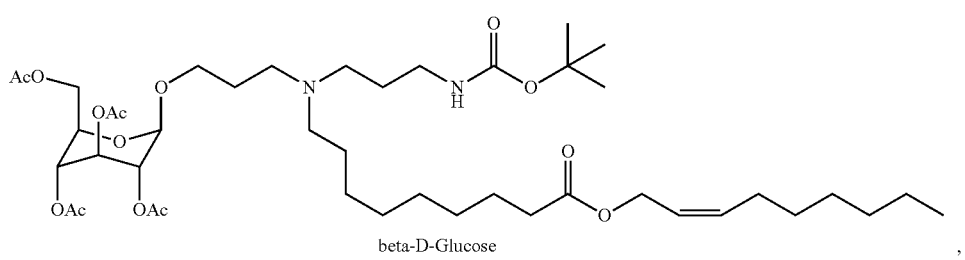
beta-D-Glucose
GL-11

-continued
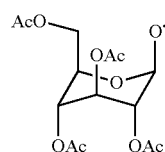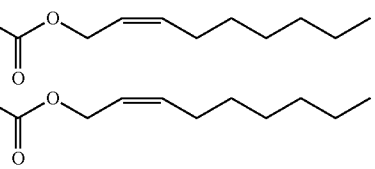
GL-12
beta-D-Glucose
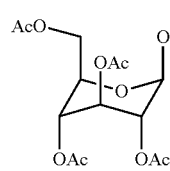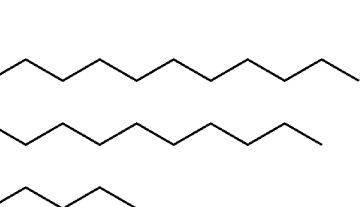
GL-13
beta-D-Glucose
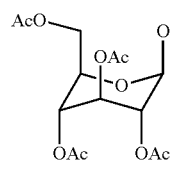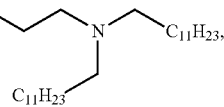
GL-14
beta-D-Glucose
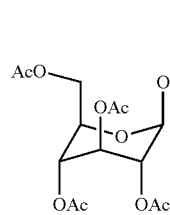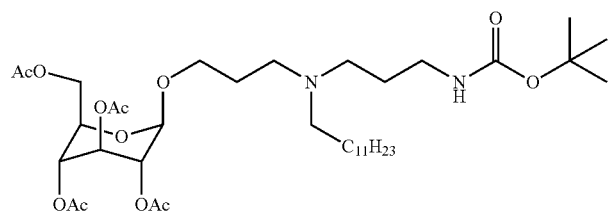
GL-15
beta-D-Glucose
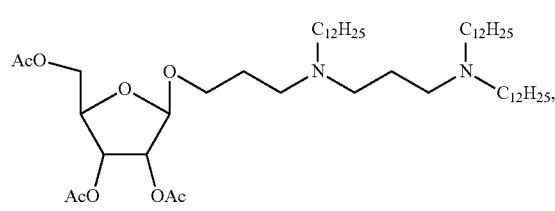
GL-16
beta-D-Ribofuranose
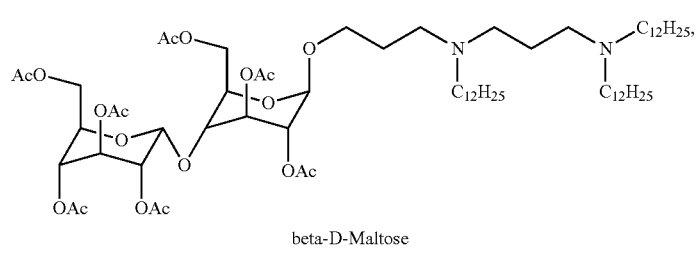
GL-17
beta-D-Maltose -continued

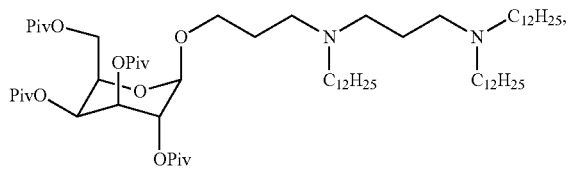
beta-D-Galaxtose pentapivalate

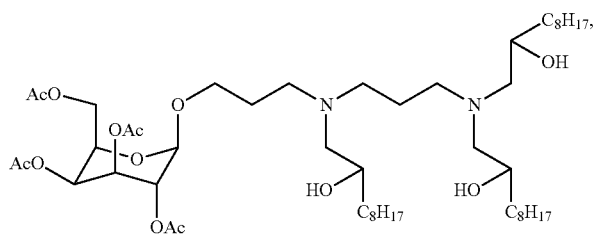

or a salt thereof.

In some embodiments, the compound is:

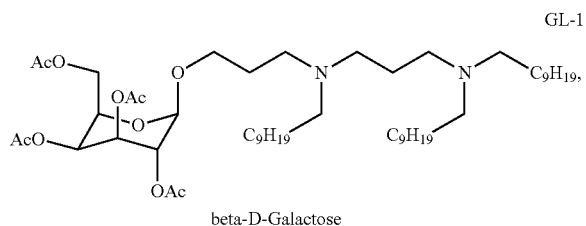
beta-D-Galactose or a salt thereof.

In some embodiments, the compound is:

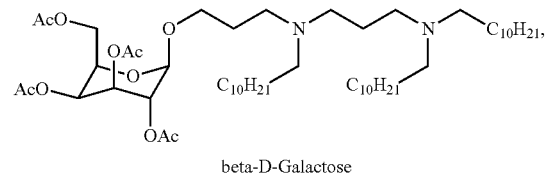
beta-D-Galactose or a salt thereof.

In some embodiments, the compound is:

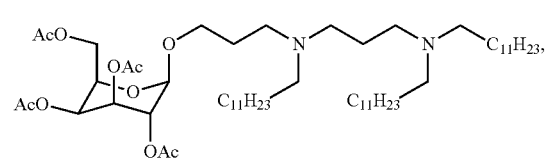
beta-D-Galactose or a salt thereof.

In some embodiments, the compound is:

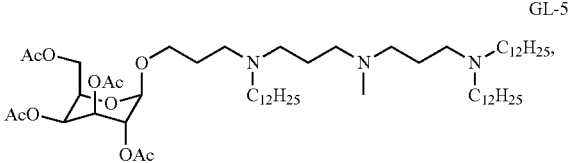
beta-D-Galactose or a salt thereof.

In some embodiments, the compound is:

or a salt thereof.

In some embodiments, the compound is:
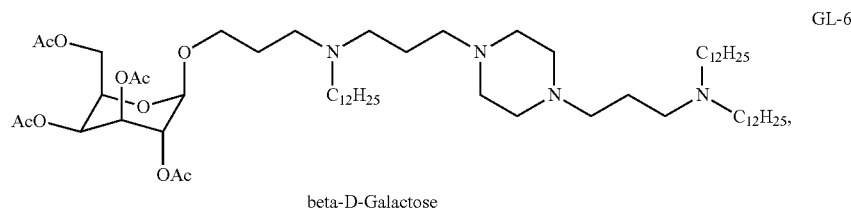
GL-6
beta-D-Galactose
or a salt thereof.
In some embodiments, the compound is:
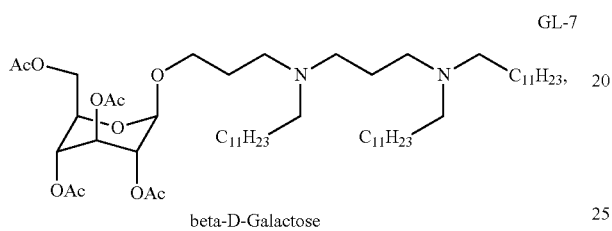
GL-7
beta-D-Galactose
or a salt thereof.
In some embodiments, the compound is selected from the following:
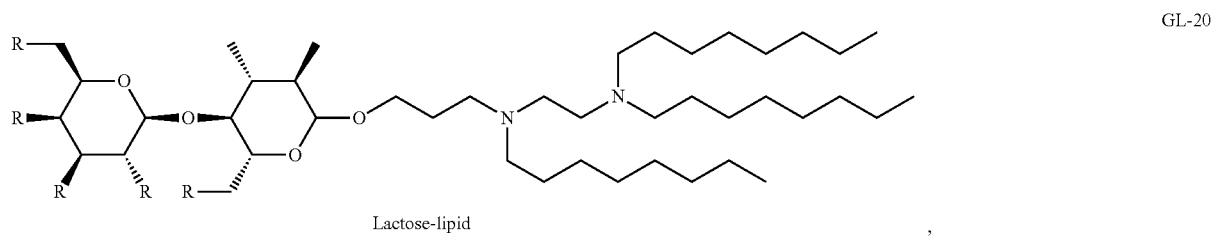
GL-20
Lactose-lipid
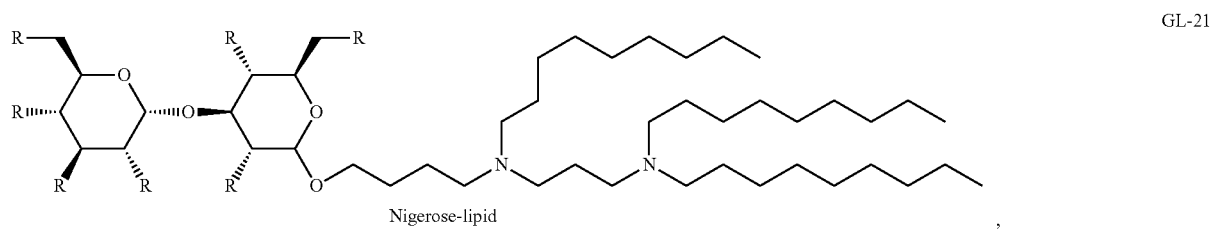
GL-21
Nigerose-lipid
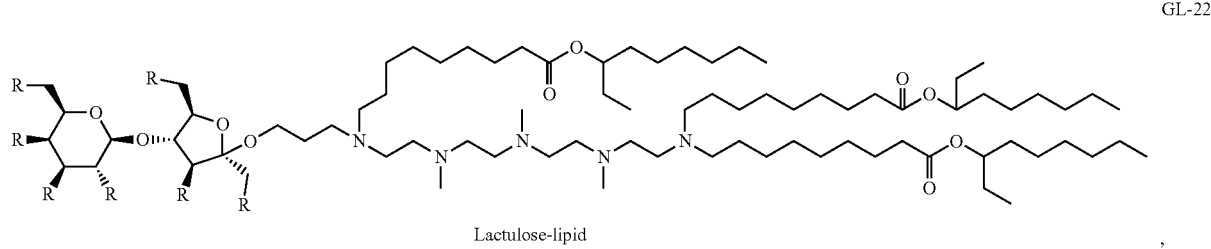
GL-22
Lactulose-lipid -continued
GL-23
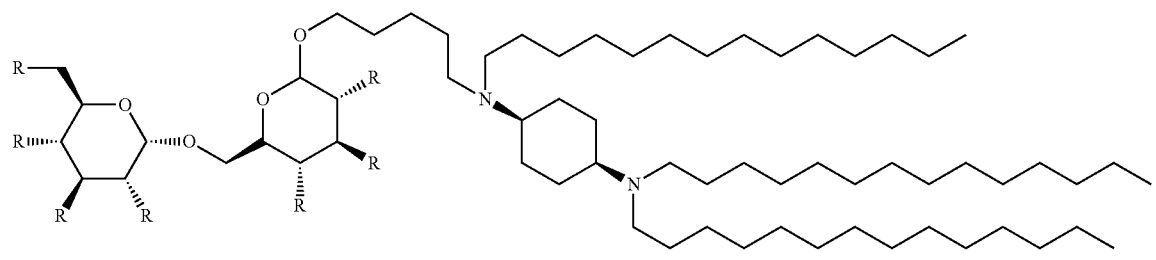
Isomaltose-lipid
GL-24
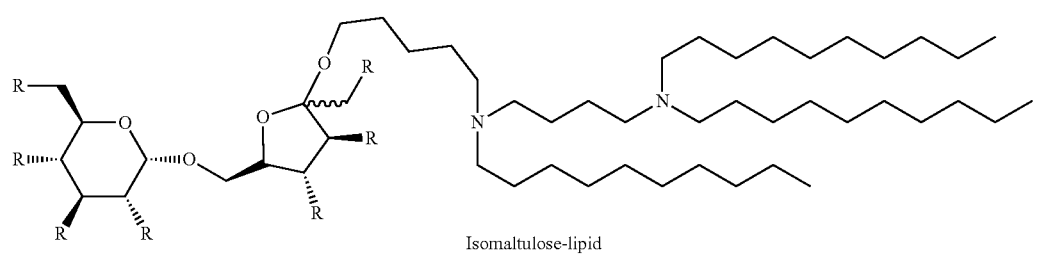
Isomaltulose-lipid
GL-25
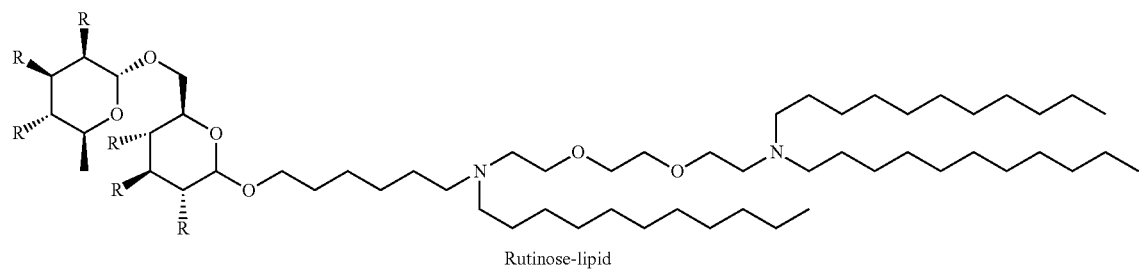
Rutinose-lipid
GL-26
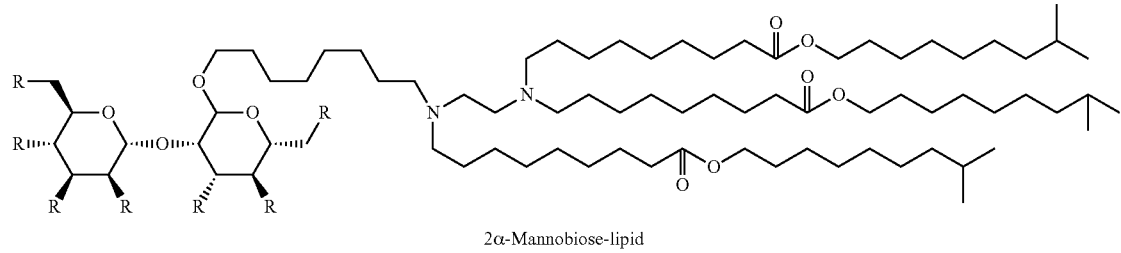
2α-Mannobiose-lipid
GL-27
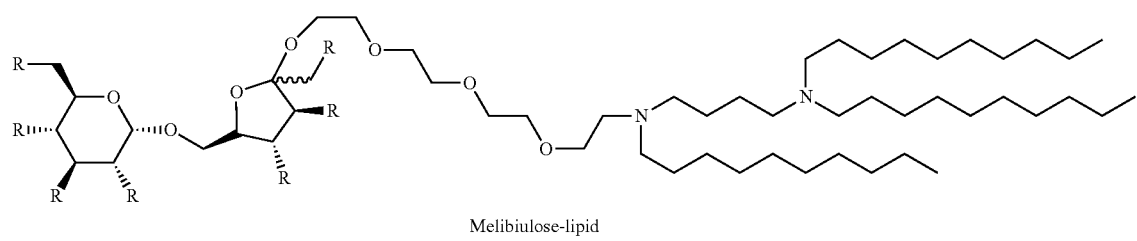
Melibiulose-lipid -continued
GL-28
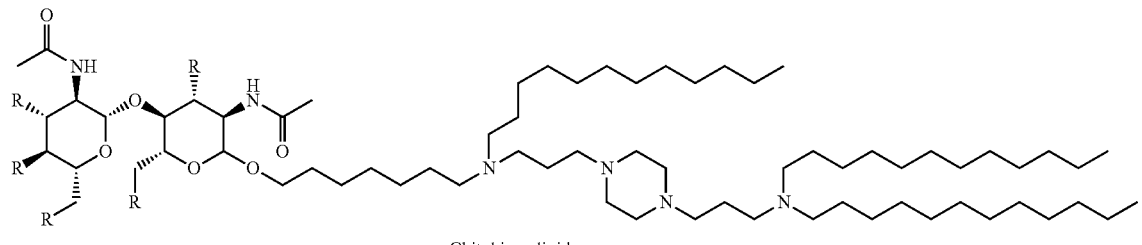
Chitobiose-lipid,
GL-29
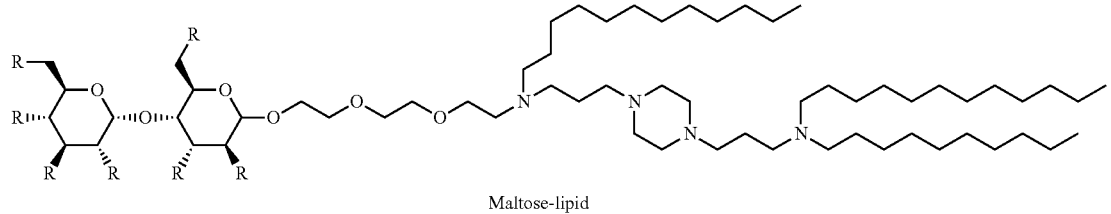
Maltose-lipid,
GL-30
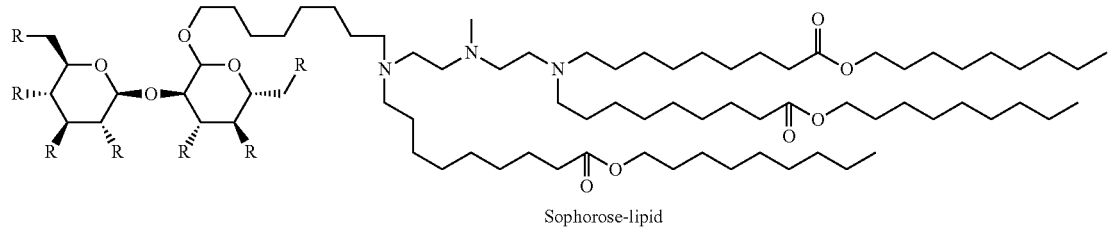
Sophorose-lipid,
GL-31
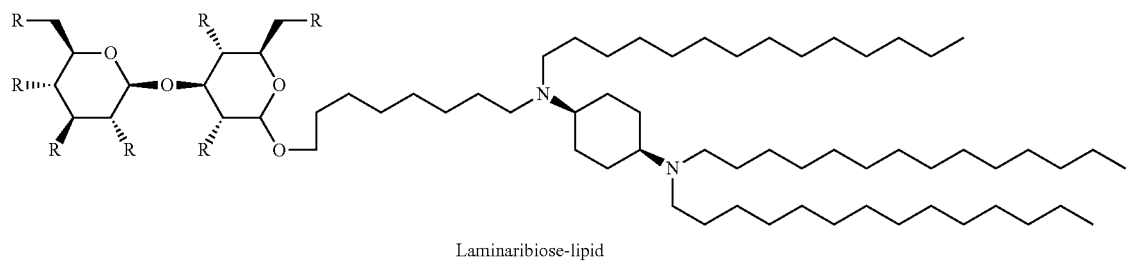
Laminaribiose-lipid,
GL-32
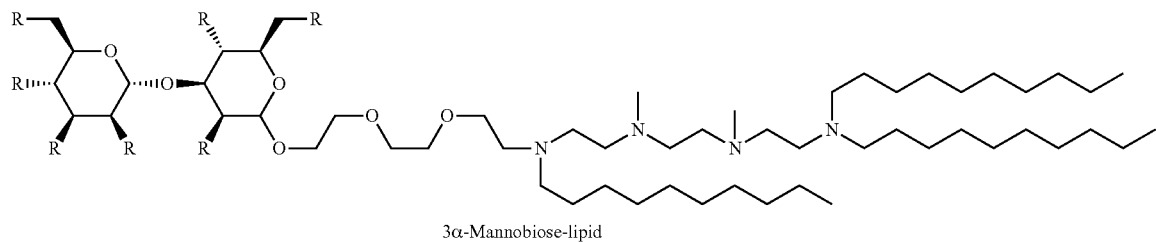
3α-Mannobiose-lipid,
GL-33
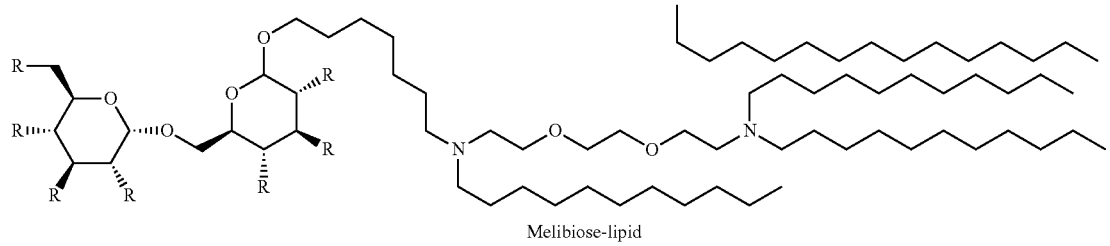
Melibiose-lipid,

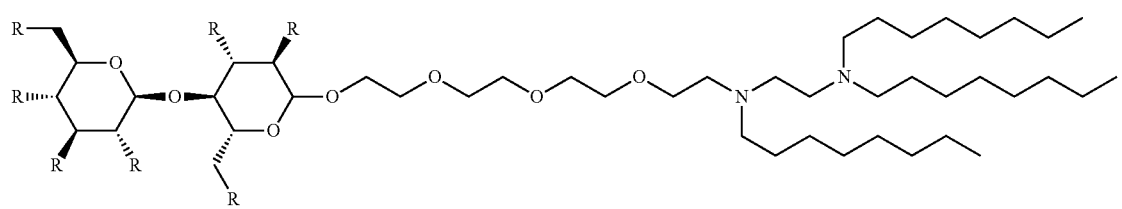
Cellobiose-lipid, GL-34
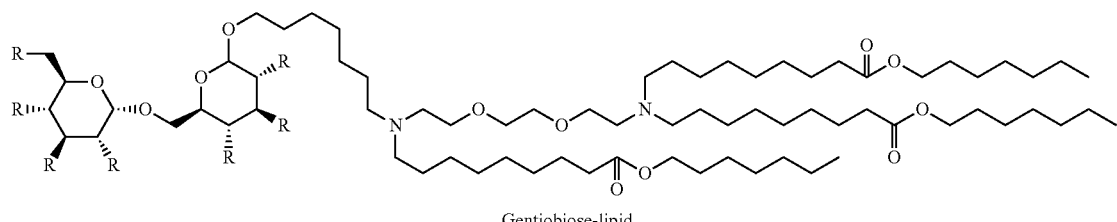
Gentiobiose-lipid, GL-35
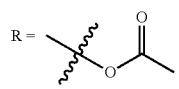
or a salt thereof.
In some embodiments, the compound is selected from the following:
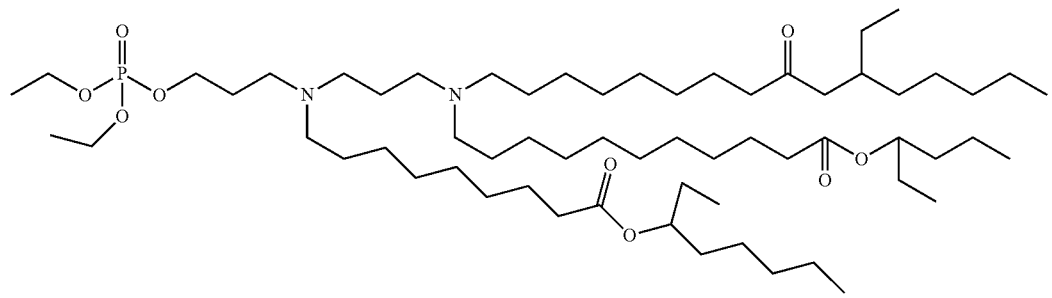
PL-1
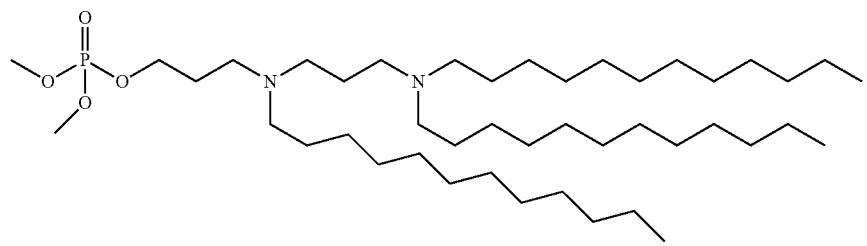
PL-2
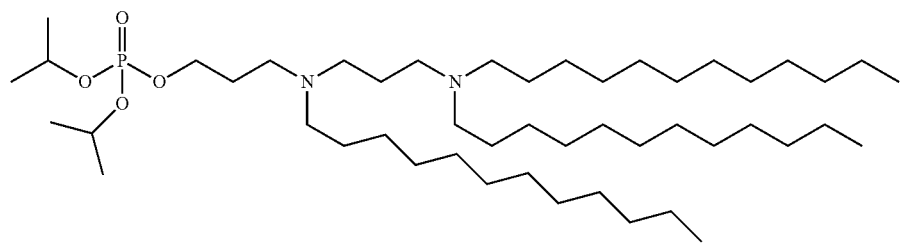
PL-3

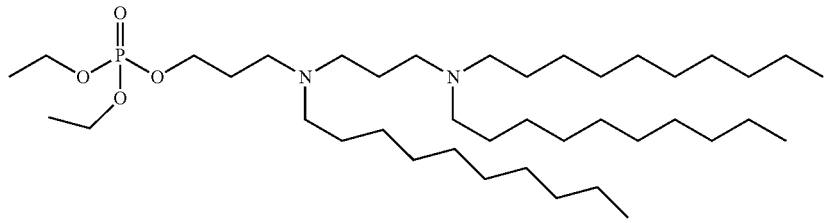
PL-4
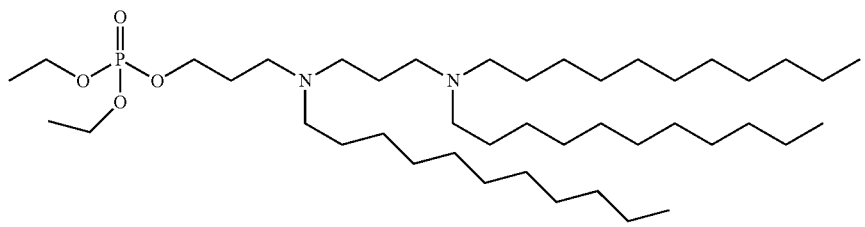
PL-5
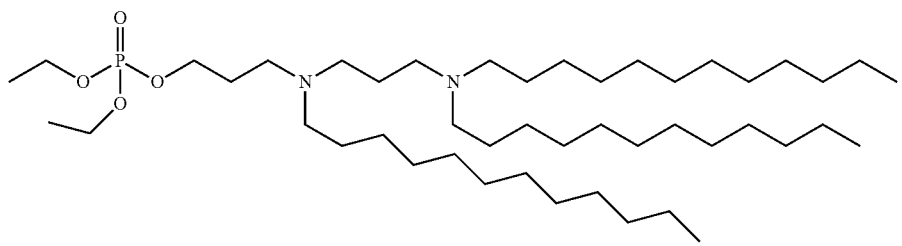
PL-6
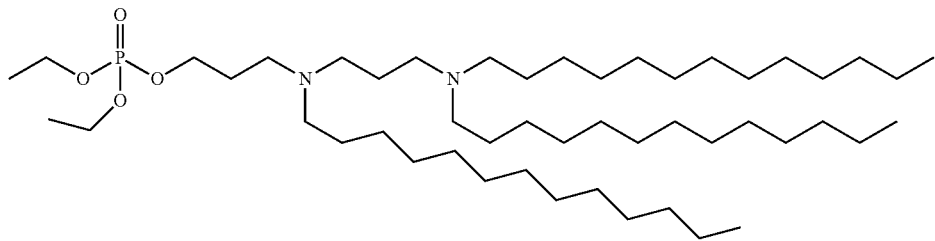
PL-7
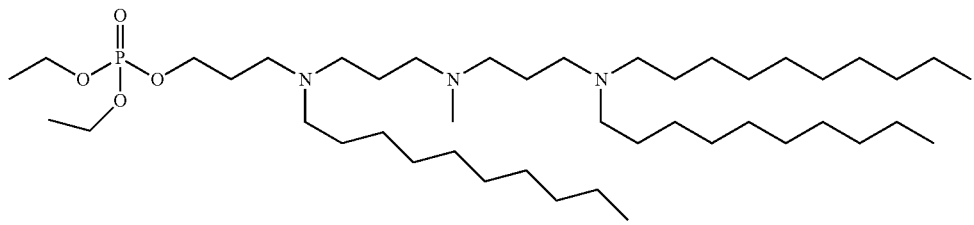
PL-8
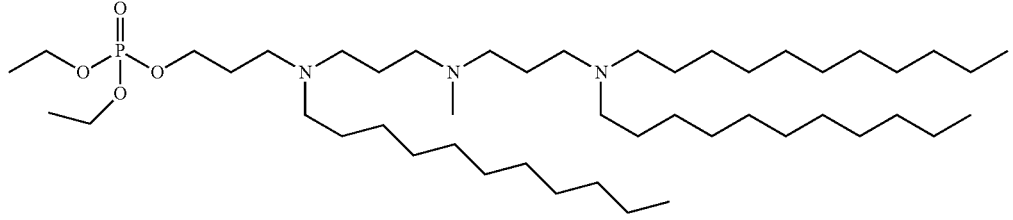
PL-9

-continued
PL-10
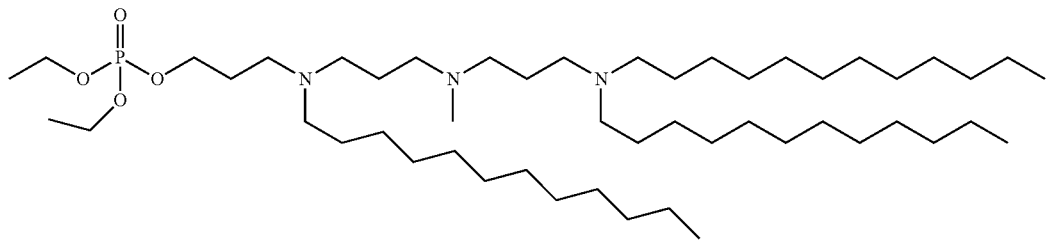
,
PL-11
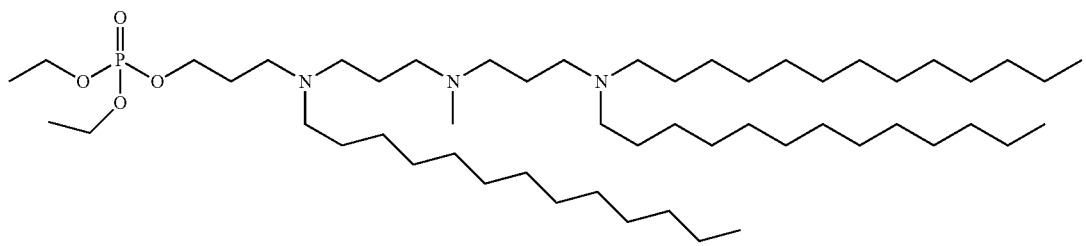
,
PL-12
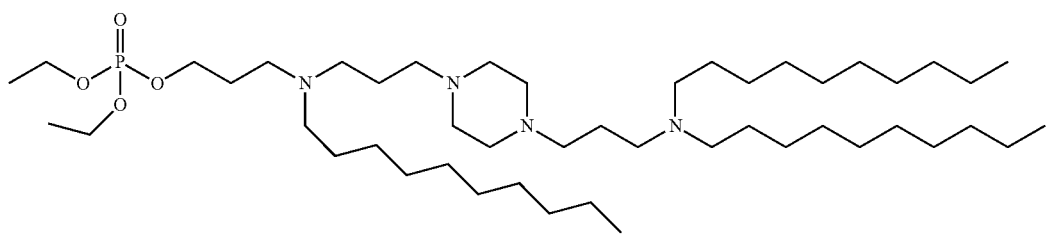
,
PL-13
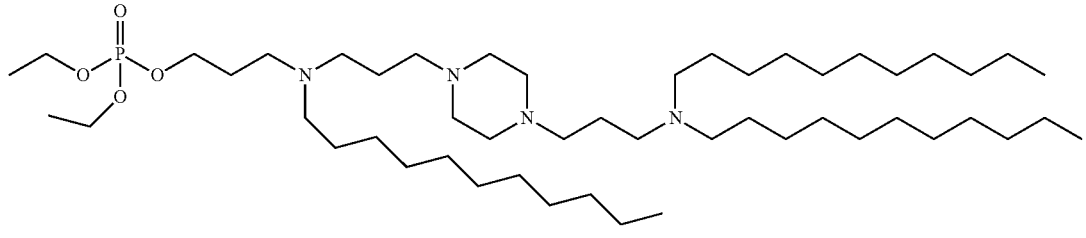
,
PL-14
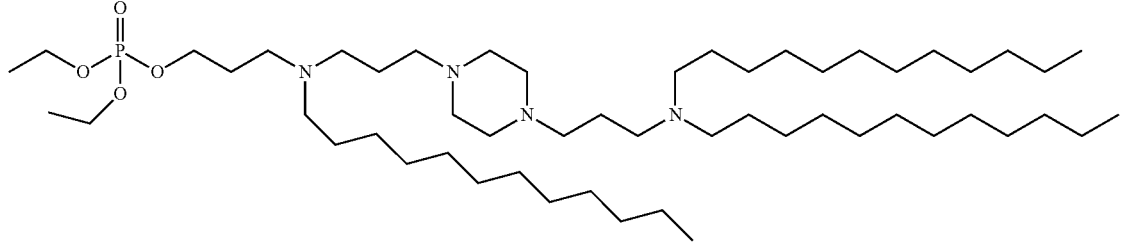
,
PL-15
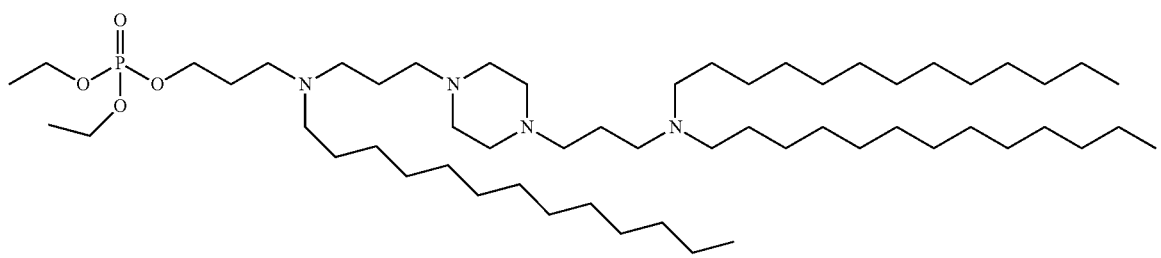
,

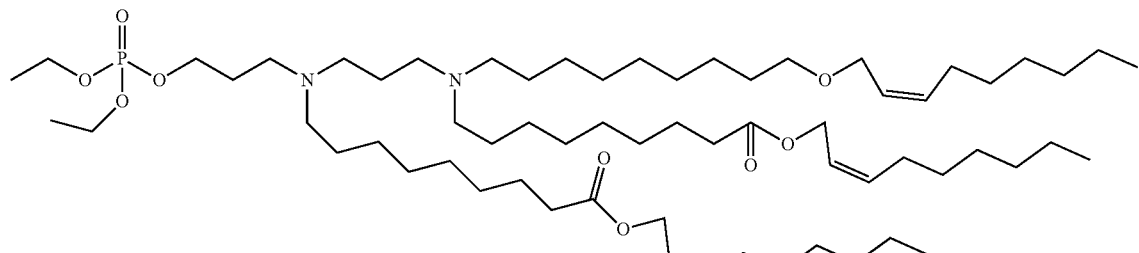
PL-16
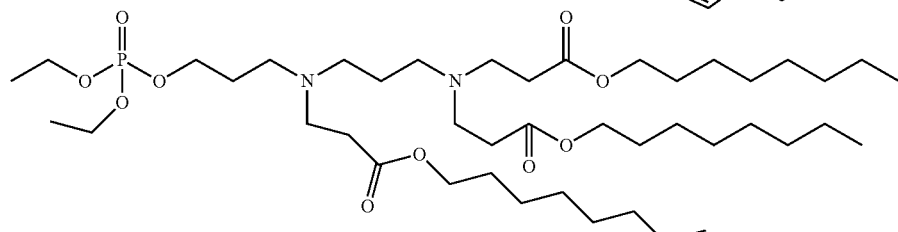
, PL-17
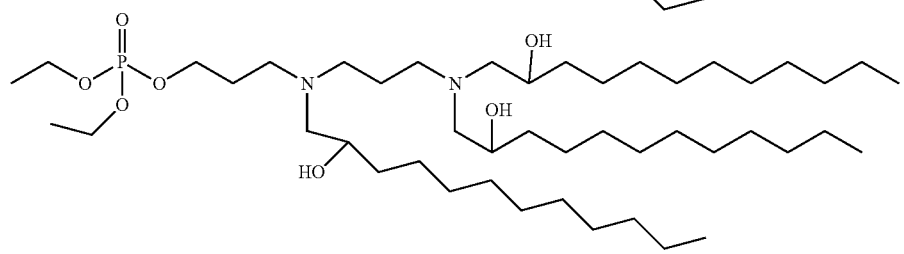
, PL-18
or a salt thereof.
In some embodiments, the compound is:
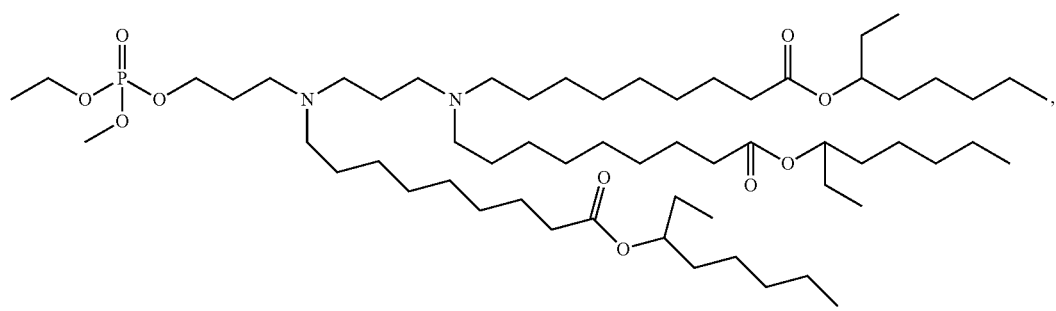
PL-1
or a salt thereof.
In some embodiments, the compound is selected from the following:
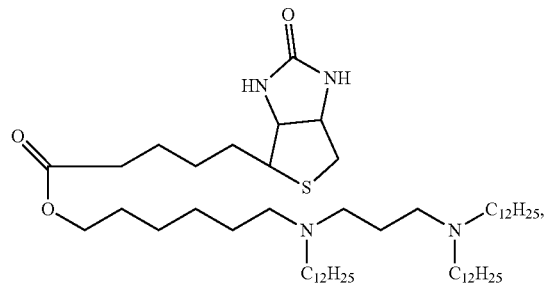
VL-1

-continued
VL-2
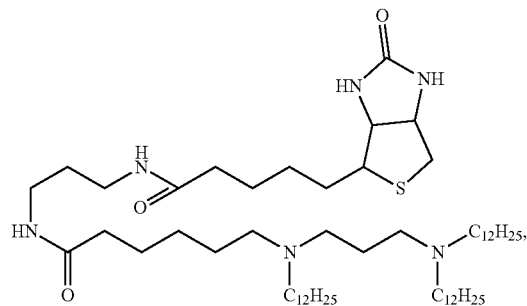
VL-3
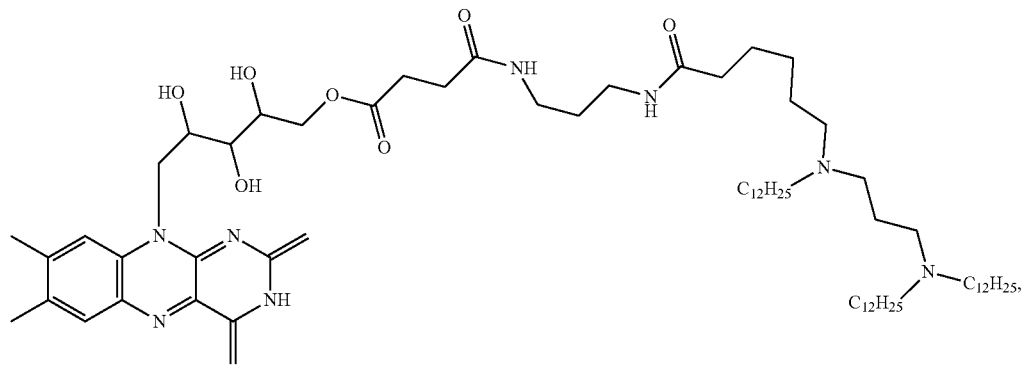
VL-4
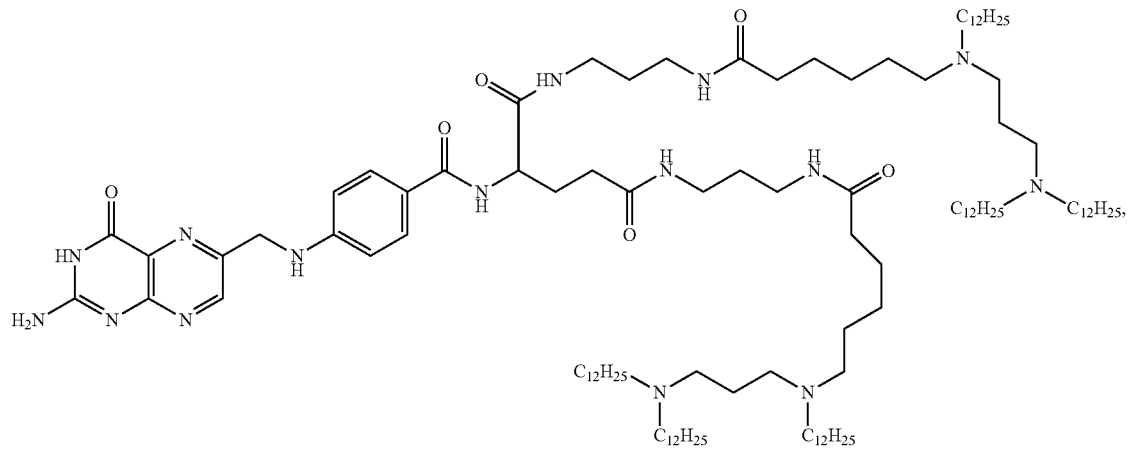
VL-5
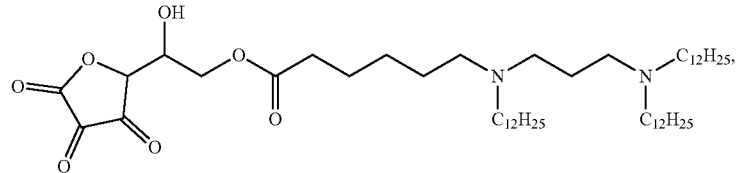
VL-6
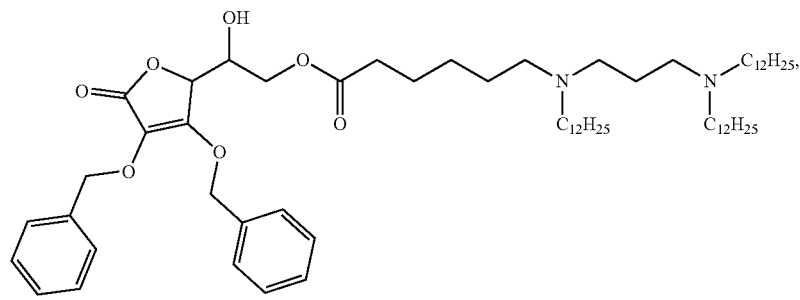

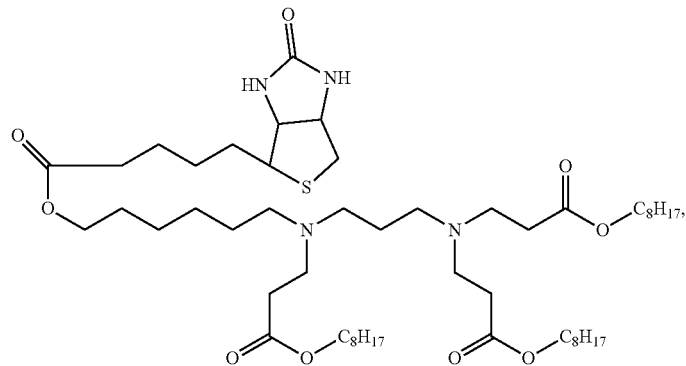
VL-7
or a salt thereof.
In some embodiments, the compound is:
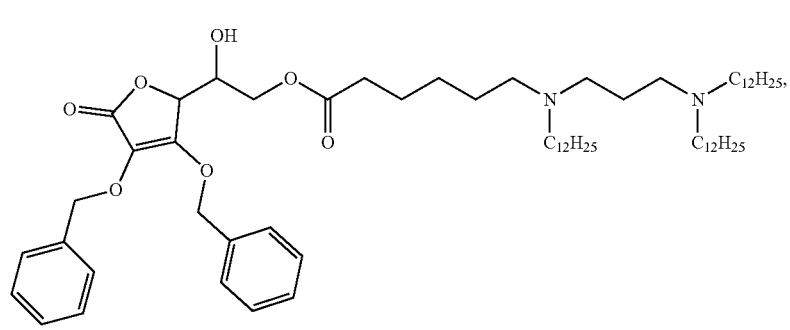
VL-6
or a salt thereof.
In some embodiments, the compound is selected from the following:
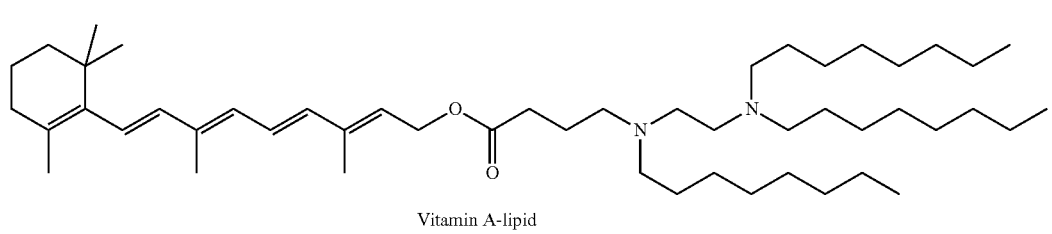
Vitamin A-lipid
VL-8
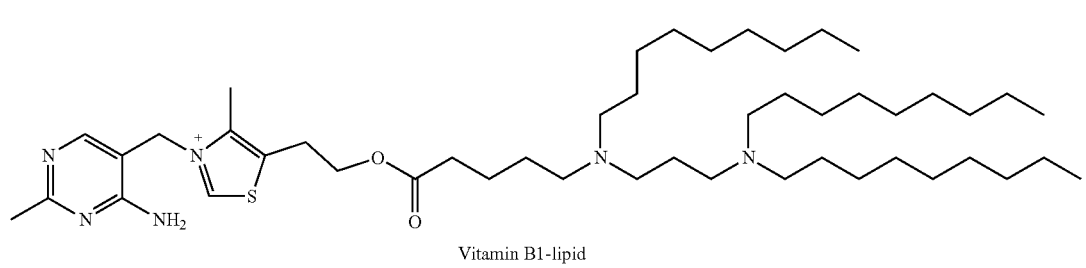
Vitamin B1-lipid
VL-9

-continued
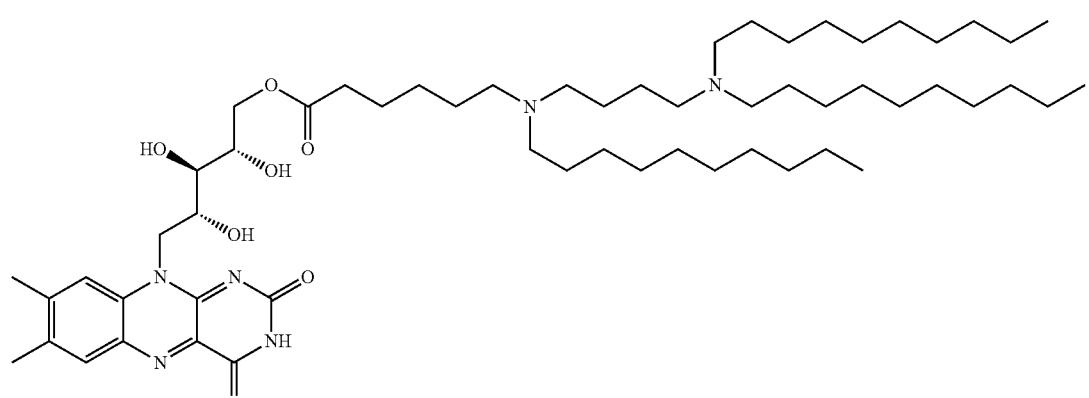
Vitamin B2-lipid, VL-10
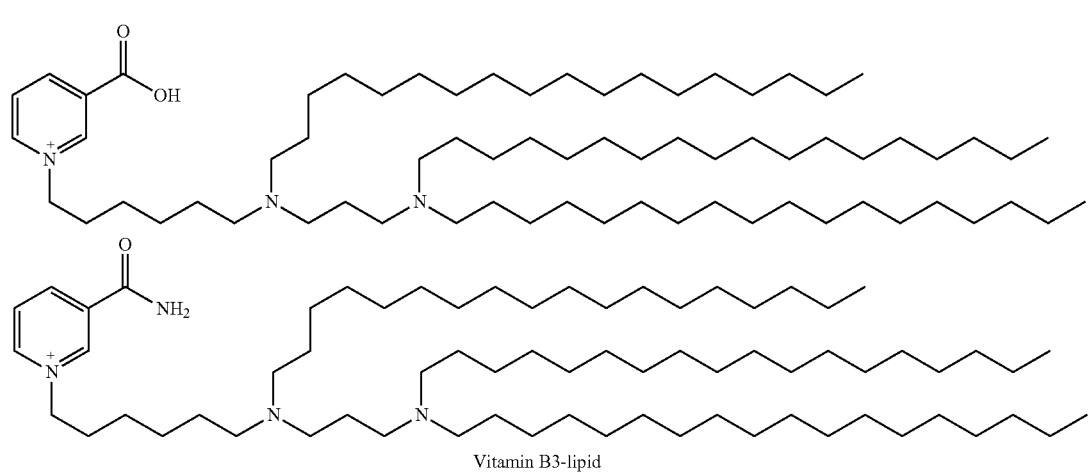
Vitamin B3-lipid, VL-11
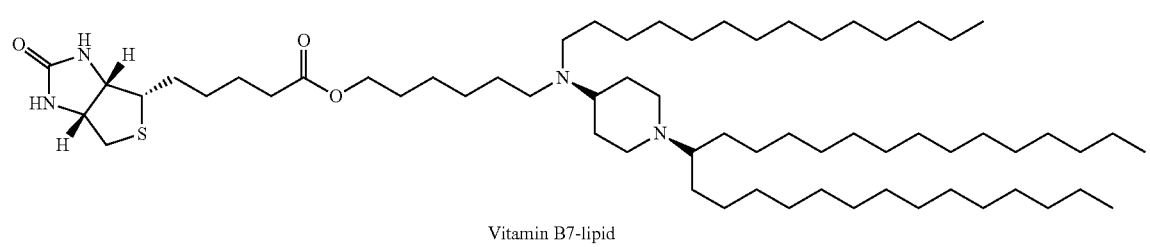
Vitamin B7-lipid, VL-12

VL-13
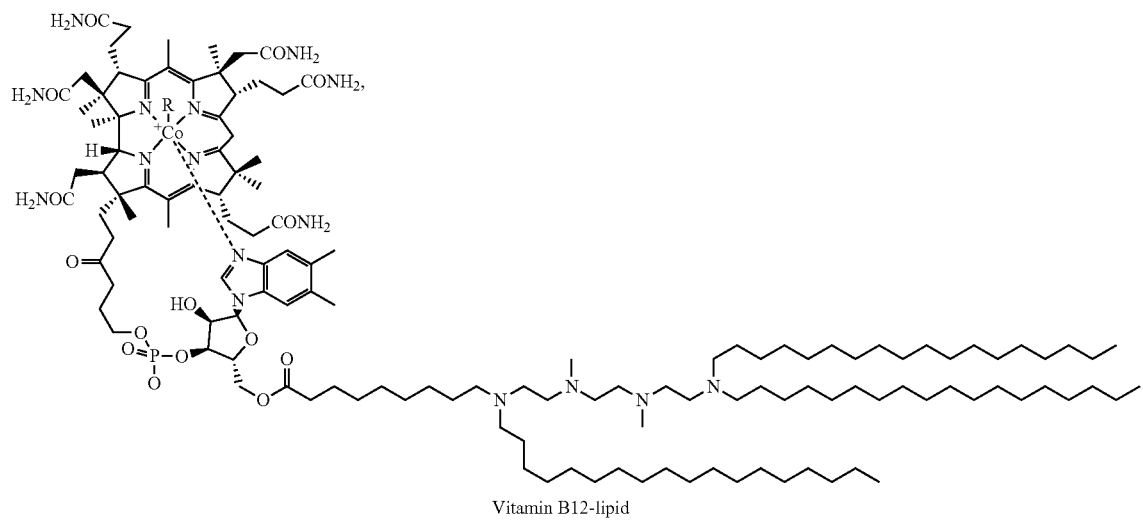
Vitamin B12-lipid
VL-14
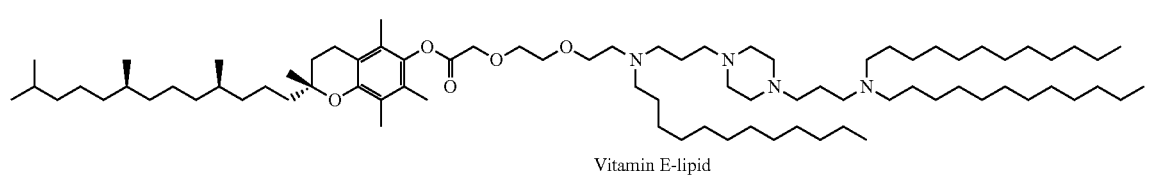
Vitamin E-lipid
VL-15
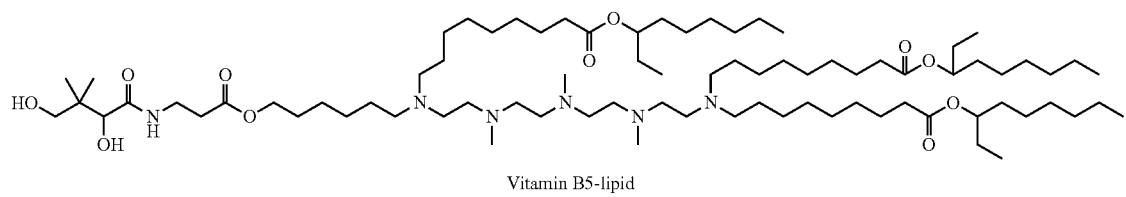
Vitamin B5-lipid
VL-16
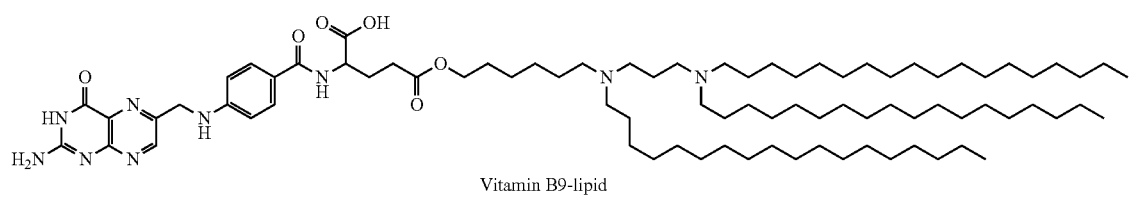
Vitamin B9-lipid
VL-17
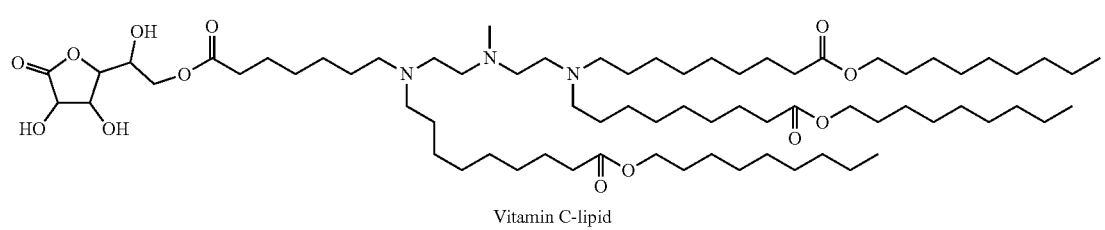
Vitamin C-lipid

VL-18

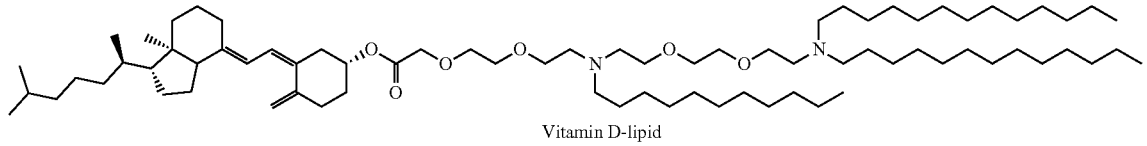

Vitamin D-lipid or a salt thereof.

In some embodiments, at least one $R^3$ is $C_7$-$C_{17}$ alkyl. In some embodiments, at least one $R^3$ is $C_{7-20}$alkenyl. In some embodiments, at least one $R^3$ is $C_{1-10}$alkylester. In some embodiments, at least one $R^3$ is $C_{1-10}$alkylester substituted with an alkyl or alkenyl group.

In some embodiments, at least one $R^3$ is a branched alkyl. In some embodiments, at least one $R^3$ is an unbranched alkyl. In some embodiments, at least one $R^3$ is a branched alkenyl. In some embodiments, at least one $R^3$ is an unbranched alkenyl.

In another aspect, disclosed herein is a composition comprising:
a compound of Formula A, I, II, III, IV, V, VI, VII, VIII, IX, or X; and
an agent.

In some embodiments, the agent is a nucleic acid. In some embodiments, the agent is a polynucleotide. In some embodiments, the agent is an RNA. In some embodiments, the agent is an mRNA.

Nanoparticles

In one aspect, the disclosure provides a nanoparticle comprising:
a compound of Formula A, I, II, III, IV, V, VI, VII, VIII, IX, or X;
a non-cationic lipid;
a polyethylene glycol-lipid; and
a sterol.

In one aspect, the disclosure provides a nanoparticle comprising: a compound of Formula A; a non-cationic lipid; a polyethylene glycol-lipid; and a sterol.

In one aspect, the disclosure provides a nanoparticle comprising: a compound of Formula I; a non-cationic lipid; a polyethylene glycol-lipid; and a sterol.

In one aspect, the disclosure provides a nanoparticle comprising: a compound of Formula II; a non-cationic lipid; a polyethylene glycol-lipid; and a sterol.

In one aspect, the disclosure provides a nanoparticle comprising: a compound of Formula III; a non-cationic lipid; a polyethylene glycol-lipid; and a sterol.

In one aspect, the disclosure provides a nanoparticle comprising: a compound of Formula IV; a non-cationic lipid; a polyethylene glycol-lipid; and a sterol.

In one aspect, the disclosure provides a nanoparticle comprising: a compound of Formula V; a non-cationic lipid; a polyethylene glycol-lipid; and a sterol.

In one aspect, the disclosure provides a nanoparticle comprising: a compound of Formula VI; a non-cationic lipid; a polyethylene glycol-lipid; and a sterol.

In one aspect, the disclosure provides a nanoparticle comprising: a compound of Formula VII; a non-cationic lipid; a polyethylene glycol-lipid; and a sterol.

In one aspect, the disclosure provides a nanoparticle comprising: a compound of Formula VIII; a non-cationic lipid; a polyethylene glycol-lipid; and a sterol.

In one aspect, the disclosure provides a nanoparticle comprising: a compound of Formula IX; a non-cationic lipid; a polyethylene glycol-lipid; and a sterol.

In one aspect, the disclosure provides a nanoparticle comprising: a compound of Formula X; a non-cationic lipid; a polyethylene glycol-lipid; and a sterol.

The various compounds of Formula A, I, II, III, IV, V, VI, VII, VIII, IX, or X are described in the Compounds section above. In some embodiments, the nanoparticle comprises a compound of Formula A, I, II, III, IV, V, VI, VII, VIII, IX, or X in a molar ratio of about 10% to about 40%. In some embodiments, the nanoparticle comprises a compound of Formula A, I, II, III, IV, V, VI, VII, VIII, IX, or X in a molar ratio of about 10%, about 15%, about 20%, about 25%, about 30%, about 35%, or about 40%. In one embodiment, the nanoparticle comprises a compound of Formula A, I, II, III, IV, V, VI, VII, VIII, IX, or X in a molar ratio of about 20%.

In some embodiments, the nanoparticle comprises a non-cationic lipid. In some embodiments, the non-cationic lipid interacts with the lipids as a helper lipid. In some embodiments, the non-cationic lipid can include, but is not limited to, 1,2-dioleoyl-sn-glycero-3-phosphoethanolamine (DOPE), 1-palmitoyl-2-oleoyl-sn-glycero-3-phosphoethanolamine (POPE), 1,2-distearoyl-sn-glycero-3-phosphocholine (DSPC), 1-stearoyl-2-oleoyl-sn-glycero-3-phosphoethanolamine (SOPE), DPPC (1,2-dipalmitoyl-sn-glycero-3-phosphocholine), 1,2-dioleyl-sn-glycero-3-phosphotidyl choline (DOPC), 1,2-dipalmitoyl-sn-glycero-3-phosphoethanolamine (DPPE), 1,2-dimyristoyl-sn-glycero-3-phosphoethanolamine (DMPE), 1,2-dioleoyl-5/7-glycero-3-phospho-(1'-rac-glycerol) (DOPG), or combinations thereof. In one embodiment, the non-cationic lipid is 1,2-dioleoyl-sn-glycero-3-phosphoethanolamine (DOPE). In one embodiment, the non-cationic lipid is 1-palmitoyl-2-oleoyl-sn-glycero-3-phosphoethanolamine (POPE), In one embodiment, the non-cationic lipid is 1,2-distearoyl-sn-glycero-3-phosphocholine (DSPC). In one embodiment, the non-cationic lipid is 1-stearoyl-2-oleoyl-sn-glycero-3-phosphoethanolamine (SOPE). While several non-cationic lipids are described here, additional non-cationic lipids can be used in combination with the compounds disclosed herein.

In some embodiments, the nanoparticle comprises a non-cationic lipid in a molar ratio of about 10% to about 40%. In some embodiments, the nanoparticle comprises a non-cationic lipid in a molar ratio of about 10%, about 15%, about 20%, about 25%, about 30%, about 35%, or about 40%. In one embodiment, the nanoparticle comprises a non-cationic lipid in a molar ratio of about 30%.

In some embodiments, the nanoparticle includes a polyethylene glycol-lipid (PEG-lipid). PEG-lipid is incorporated to form a hydrophilic outer layer and stabilize the particles. Nonlimiting examples of polyethylene glycol-lipids include PEG-modified lipids such as PEG-modified phosphatidylethanolamines, PEG-modified phosphatidic acids, PEG-modified ceramides, PEG-modified dialkylamines, PEG-modified diacylglycerols, and PEG-modified dialkylglycerols. Representative polyethylene glycol-lipids include DMG-PEG, DLPE-PEGs, DMPE-PEGs, DPPC-PEGs, and DSPE-PEGs. In one embodiment, the polyethylene glycol-lipid is 1,2-dimyristoyl-sn-glycerol, methoxypolyethylene glycol (DMG-PEG). In one embodiment, the polyethylene glycol-lipid is 1,2-dimyristoyl-sn-glycerol, methoxypolyethylene glycol-2000 (DMG-PEG2000). DMG-PEGXXXX means 1,2-dimyristoyl-sn-glycerol, methoxypolyethylene glycol-XXXX, wherein XXXX signifies the molecular weight of the polyethylene glycol moiety, e.g. DMG-PEG2000 or DMG-PEG5000.

In some embodiments, the nanoparticle comprises a polyethylene glycol-lipid in a molar ratio of about 0% to about 5%. In some embodiments, the nanoparticle comprises a polyethylene glycol-lipid in a molar ratio of about 0%, about 0.25%, about 0.5%, about 0.75%, about 1%, about 1.5%, about 2%, about 3%, about 4%, or about 5%. In one embodiment, the nanoparticle comprises a polyethylene glycol-lipid in a molar ratio of about 0.75%.

In some embodiments, the nanoparticle includes a sterol. Sterols are well known to those skilled in the art and generally refers to those compounds having a perhydrocyclopentanophenanthrene ring system and having one or more OH substituents. Examples of sterols include, but are not limited to, cholesterol, campesterol, ergosterol, sitosterol, and the like.

In some embodiments, the sterol is selected from a cholesterol-based lipid. In some embodiments, the one or more cholesterol-based lipids are selected from cholesterol, PEGylated cholesterol, DC-Choi (N,N-dimethyl-N-ethylcarboxamidocholesterol), 1,4-bis(3-N-oleylamino-propyl) piperazine, or combinations thereof.

The sterol can be used to tune the particle permeability and fluidity base on its function in cell membranes. In one embodiment, the sterol is cholesterol.

In some embodiments, the nanoparticle comprises a sterol in a molar ratio of about 25% to about 50%. In some embodiments, the nanoparticle comprises a sterol in a molar ratio of about 25%, about 30%, about 35%, about 40%, about 45%, or about 50%. In one embodiment, the nanoparticle comprises a sterol in a molar ratio of about 40%.

In one embodiment, the disclosure provides a nanoparticle comprising:
a compound of Formula A, I, II, III, IV, V, VI, VII, VIII, IX, or X;
1,2-dioleoyl-sn-glycero-3-phosphoethanolamine (DOPE);
1,2-dimyristoyl-sn-glycerol, methoxypolyethylene glycol (DMG-PEG2000); and cholesterol.

In one embodiment, the disclosure provides a nanoparticle comprising:
a compound of Formula A, I, II, III, IV, V, VI, VII, VIII, IX, or X;
1-palmitoyl-2-oleoyl-sn-glycero-3-phosphoethanolamine (POPE);
1,2-dimyristoyl-sn-glycerol, methoxypolyethylene glycol (DMG-PEG2000); and cholesterol.

In one embodiment, the disclosure provides a nanoparticle comprising:
a compound of Formula A, I, II, III, IV, V, VI, VII, VIII, IX, or X;
1,2-di stearoyl-sn-glycero-3-phosphocholine (DSPC);
1,2-dimyristoyl-sn-glycerol, methoxypolyethylene glycol (DMG-PEG2000); and cholesterol.

In one embodiment, the nanoparticle further comprises an agent. In one embodiment, the nanoparticle further comprises a therapeutic agent. In one embodiment, the nanoparticle further comprises a diagnostic agent.

The agents delivered into cells can be a polynucleotide. Polynucleotides or oligonucleotides that can be introduced according to the methods herein include DNA, cDNA, and RNA sequences of all types. For example, the polynucleotide can be double stranded DNA, single-stranded DNA, complexed DNA, encapsulated DNA, naked RNA, encapsulated RNA, messenger RNA (mRNA), tRNA, short interfering RNA (siRNA), double stranded RNA (dsRNA), micro-RNA (miRNA), antisense RNA (asRNA) and combinations thereof. The polynucleotides can also be DNA constructs, such as expression vectors, expression vectors encoding a desired gene product (e.g., a gene product homologous or heterologous to the subject into which it is to be introduced), and the like. In one embodiment, the agent is an mRNA.

Compositions

Compositions, as described herein, comprising an active compound and an excipient of some sort may be useful in a variety of medical and non-medical applications. For example, pharmaceutical compositions comprising an active compound and an excipient may be useful in the delivery of an effective amount of an agent to a subject in need thereof. Nutraceutical compositions comprising an active compound and an excipient may be useful in the delivery of an effective amount of a nutraceutical, e.g., a dietary supplement, to a subject in need thereof. Cosmetic compositions comprising an active compound and an excipient may be formulated as a cream, ointment, balm, paste, film, or liquid, etc., and may be useful in the application of make-up, hair products, and materials useful for personal hygiene, etc. Compositions comprising an active compound and an excipient may be useful for non-medical applications, e.g., such as an emulsion or emulsifier, useful, for example, as a food component, for extinguishing fires, for disinfecting surfaces, for oil cleanup, etc.

In certain embodiments, the composition further comprises an agent, as described herein. For example, in certain embodiments, the agent is a small molecule, organometallic compound, nucleic acid, protein, peptide, polynucleotide, metal, targeting agent, an isotopically labeled chemical compound, drug, vaccine, immunological agent, or an agent useful in bioprocessing. In certain embodiments, the agent is a polynucleotide. In certain embodiments, the polynucleotide is DNA or RNA. In certain embodiments, the RNA is RNAi, dsRNA, siRNA, shRNA, miRNA, or antisense RNA. In certain embodiments, the polynucleotide and the one or more active compounds are not covalently attached.

In one aspect, the disclosure provides a composition comprising:
a compound of Formula A, I, II, III, IV, V, VI, VII, VIII, IX, or X; and
an agent.

In one aspect, the disclosure provides a composition comprising:
a nanoparticle, comprising a compound of Formula A, I, II, III, IV, V, VI, VII, VIII, IX, or X; and
an agent.

Agents

Agents to be delivered by the compounds, compositions, and systems described herein may be therapeutic, diagnostic, or prophylactic agents. Any chemical compound to be administered to a subject may be delivered using the particles or nanoparticles described herein. The agent may be an organic molecule (e.g., a therapeutic agent, a drug), inorganic molecule, nucleic acid, protein, amino acid, peptide, polypeptide, polynucleotide, targeting agent, isotopically labeled organic or inorganic molecule, vaccine, immunological agent, etc.

In certain embodiments, the agents are organic molecules with pharmaceutical activity, e.g., a drug. In certain embodiments, the drug is an antibiotic, anti-viral agent, anesthetic, steroidal agent, anti-inflammatory agent, anti-neoplastic agent, anti-cancer agent, antigen, vaccine, antibody, decongestant, antihypertensive, sedative, birth control agent, progestational agent, anti-cholinergic, analgesic, anti-depressant, anti-psychotic, f3-adrenergic blocking agent, diuretic, cardiovascular active agent, vasoactive agent, non-steroidal anti-inflammatory agent, nutritional agent, etc.

In certain embodiments of the present disclosure, the agent to be delivered may be a mixture of agents.

Diagnostic agents include gases; metals; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

Therapeutic and prophylactic agents include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Therapeutic and prophylactic agents may be combined with interleukins, interferon, cytokines, and adjuvants such as cholera toxin, alum, Freund's adjuvant, etc. Prophylactic agents include antigens of such bacterial organisms as *Streptococccus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia rickettsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

Methods

In one aspect, provided herein is a method for the delivery of an agent (for example, a polynucleotide) into a cell comprising;
    introducing into the cell a composition comprising;
        a nanoparticle, comprising;
            a compound of Formula A, I, II, III, IV, V, VI, VII, VIII, IX, or X;
            a non-cationic lipid;
            a polyethylene glycol-lipid;
            a sterol; and
        an agent.

In one aspect, disclosed herein is a method for the delivery of an agent into a cell comprising;
    introducing into the cell a composition comprising;
        a nanoparticle comprising;
a compound of Formula A:

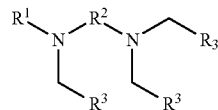

Formula A or a salt thereof, wherein:
$R^1$ is an alkyl or ether linker, wherein the alkyl or ether linker is substituted with a carbohydrate moiety, a phosphate moiety, or a vitamin moiety;
$R^2$ is alkyl, cycloalkyl, heterocycloalkyl, alkylheterocycloalkyl, amide, alkylamide, ether, alkylether,

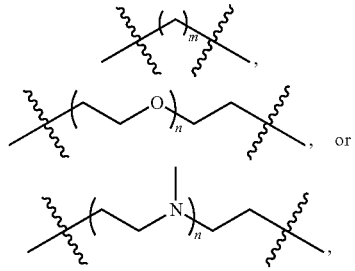

, or

, wherein m is an integer from 1 to 20,
wherein n is an integer from 1 to 3; and
each $R^3$ is independently selected from alkyl, alkenyl, alkynyl, ester, or alkylester;
a non-cationic lipid;
a polyethylene glycol-lipid;
a sterol; and
    an agent.

In one aspect, disclosed herein is a method for the delivery of an agent into a cell comprising;
    introducing into the cell a composition comprising;
        a nanoparticle comprising;
a compound of Formula I, II, III, IV, V, VI, VII, VIII, IX, or X:

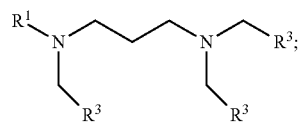

Formula I

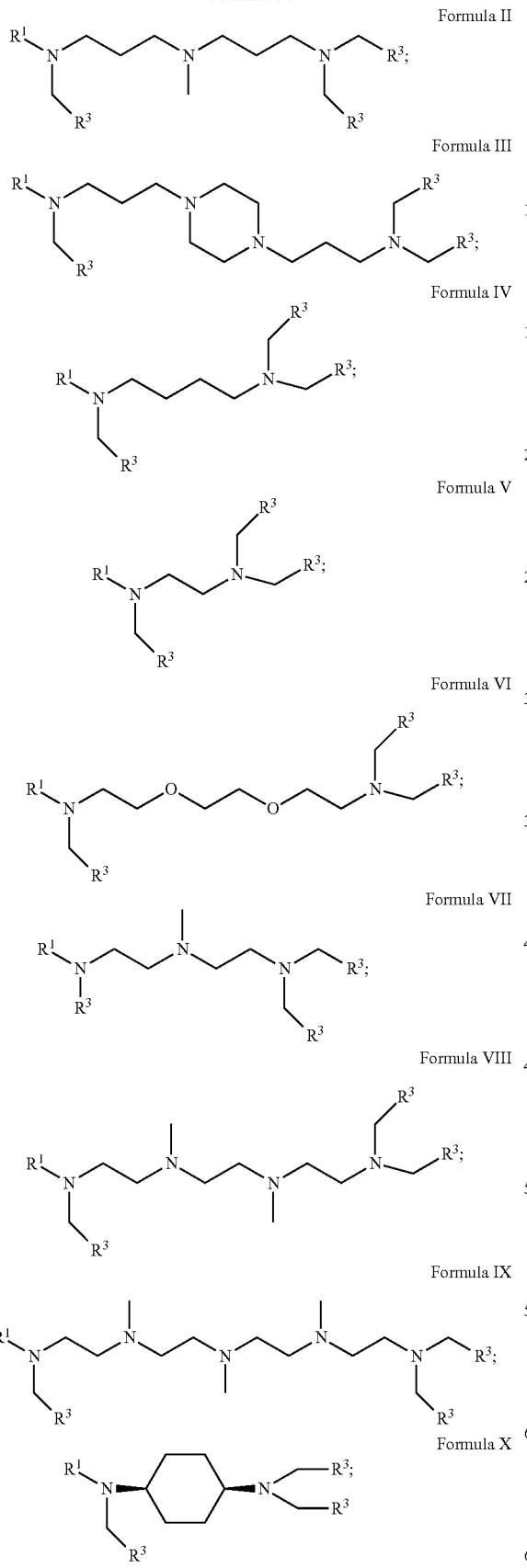

or a salt thereof, wherein:

$R^1$ is an alkyl or ether linker, wherein the alkyl or ether linker is substituted with a carbohydrate moiety, a phosphate moiety, or a vitamin moiety; and each $R^3$ is independently selected from alkyl, alkenyl, alkynyl, ester, or alkylester;

a non-cationic lipid;

a polyethylene glycol-lipid;

a sterol; and an agent.

In some embodiments, a nanoparticle comprising any compound as described in the Compounds section above, is used in the methods herein, for delivery of an agent into a cell.

In some embodiments, the agent is a polynucleotide. In some embodiments, the agent is an RNA. In some embodiments, the agent is an mRNA. In some embodiments, the agent is a therapeutic agent, diagnostic agent, or prophylactic agent.

In some embodiments, provided herein are methods for the delivery of polynucleotides. In some embodiments, provided herein are methods for the delivery of polynucleotides (for example, mRNA) to correct a mutation in a genome. For example, mRNAs can be delivered to correct mutations that cause hemophilia (due to mutations in the genes encoding Factor VIII (F8; hemophilia A) or Factor IX (F9; hemoglobin B). In some embodiments, provided herein are methods for the delivery of polynucleotides. In some embodiments, provided herein are methods for the delivery of polynucleotides (for example, mRNA) to provide expression of the mRNA (and translation to produce a protein) in a cell.

EXAMPLES

The following examples are set forth below to illustrate the compounds, compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Biomimetic Nanomaterials for Nucleic Acid Delivery

Efficient delivery of mRNA is a key step and challenge for the application of mRNA therapeutics. Despite promising data from ongoing clinical trials, the clinical use of mRNA requires the discovery and development of more efficient delivery systems.

Disclosed herein is a library of biomimetic nanomaterials containing carbohydrate, phosphate or vitamin groups for gene therapy and drug delivery applications. These compounds were designed and synthesized with diverse carbohydrate, phosphate, and vitamin heads and tunable lipid tails. These materials showed high delivery efficiency of mRNA in Hep3B and Jurkat cells. Specifically, the compounds demonstrate significantly higher expression of luciferase compared to the control group and are useful for gene therapy and drug delivery.

These nanomaterials are composed of three parts, including the carbohydrate, phosphate or vitamin heads, the amino cores and lipid tails. Schemes 1-15 shows the synthetic routes to these materials. Schemes 16-18 listed synthesized compounds.

Chemical Synthesis

1. Add Di-tert-butyl dicarbonate in a $CH_2Cl_2$ dropwise into an excess amount of diamine in $CH_2Cl_2$ under stirring at room temperature. 5 hours later, 1N $NaHCO_3$ is added to the reacting mixture slowly. The organic layer is collected and washed with additional 1N $NaHCO_3$ and saturated brine, successively. After dried over $Na_2SO_4$, the organic layer is evaporated to obtain the single Boc-protected diamine.

2. Single Boc-protected diamine and bromine containing glucosyl-group are stirred with triethylamine in DMF for 48 hours at room temperature. The intermediate is obtained after purification through silica column.

3. The intermediate from step two and an excess amount of trifluoroacetic acid are stirred in $CH_2Cl_2$ for 2 hours at room temperature to remove the Boc group. Trifluoroacetic acid is removed through evaporation to obtain the rough product.

4. The crude mixture from step three, aldehyde and $NaBH(AcO)_3$ are stirred in THF for 5-12 hours at room temperature. The final product is obtained after purifying the reacting mixture through a silica column.

Scheme 1: (A) General synthetic routes of triple-tail glycolipids using aldehyde containing chains; (B) One example, synthesis of GL-1.

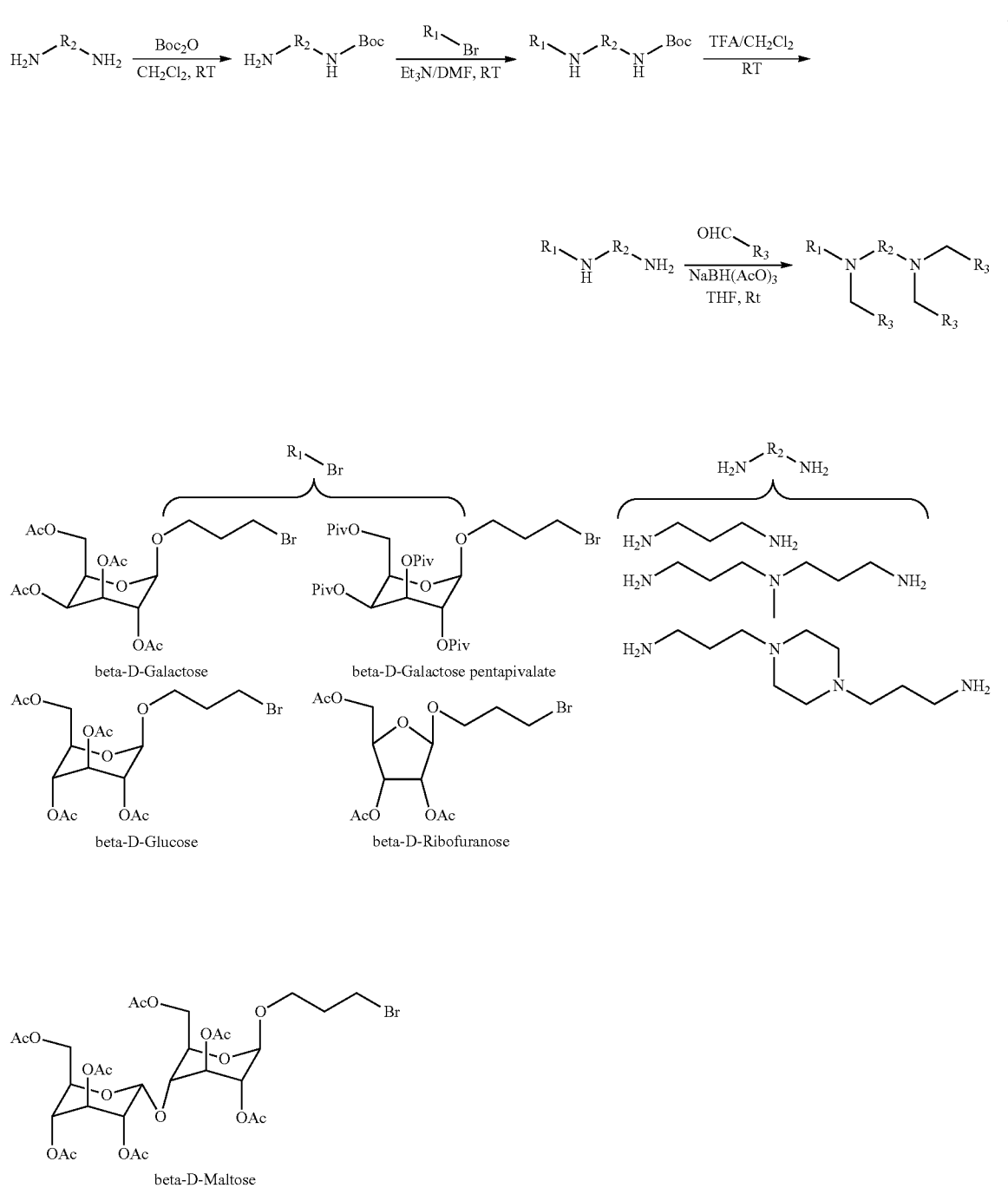

-continued

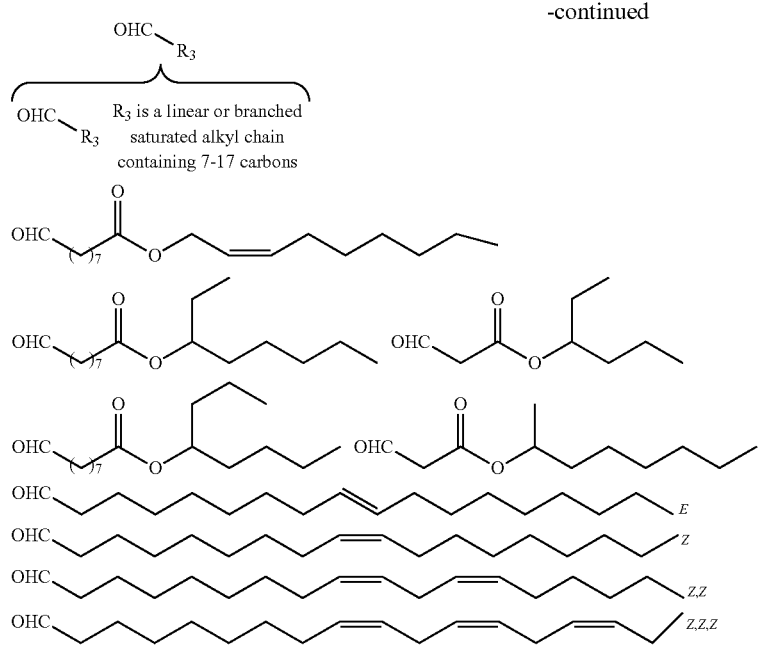

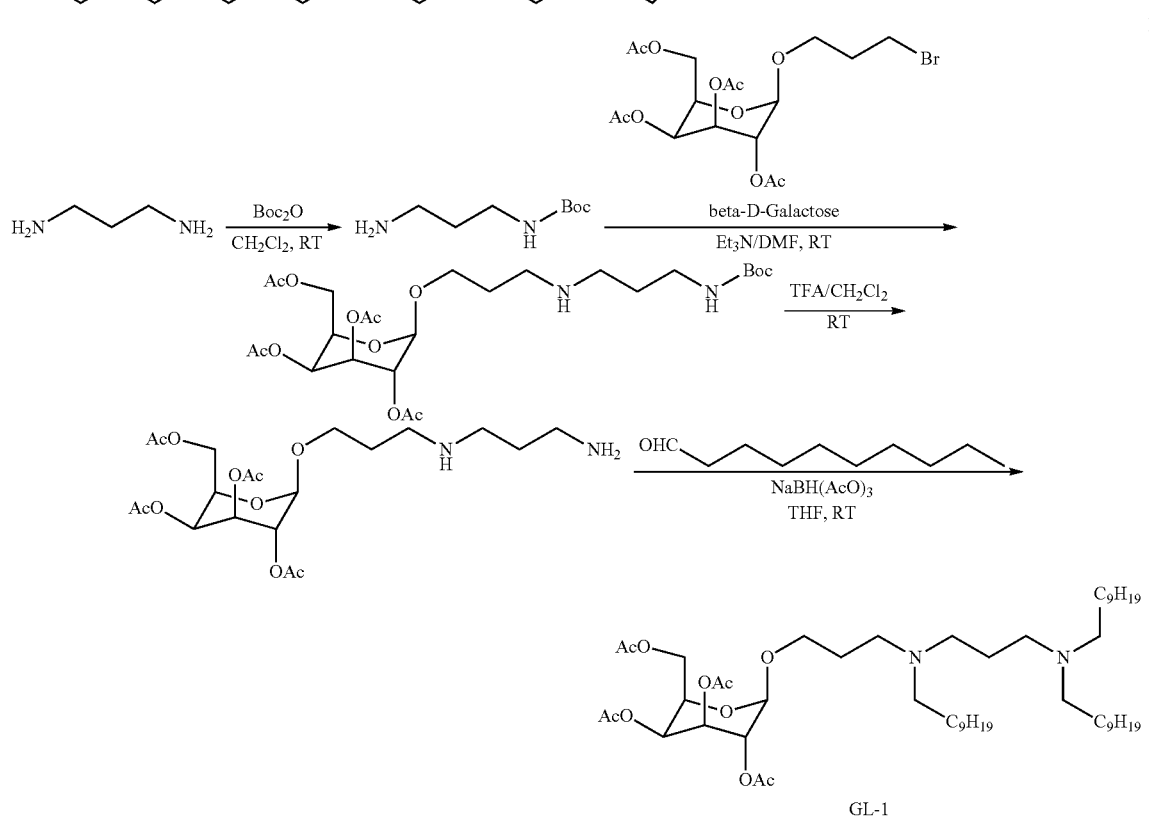

GL-1

Synthetic Route of GL-1:

To a solution of diamine in CHCl₃ was slowly added a solution of Boc₂O in CHCl₃ via an additional funnel over 2.5 h. The resulting suspension was stirred and NaHCO₃ (1N) was slowly added. The organic layer was washed with 1N NaHCO₃ and brine, and then dried over solid MgSO₄. The solution was then filtered, evaporated and dried under high vacuum in order to afford intermediate 1.

Intermediate 1 was stirred in DMF with beta-D-Galactose derivative and trimethylamine for 48 h. After adding CH₂Cl₂ the organic phase was washed with water for three times and then dried over solid MgSO₄. The solution was then filtered, evaporated and dried under high vacuum. The product was purified by silica column chromatography in order to afford intermediate 2.

Intermediate 2 was stirred in excess amount of trifluoroacetic acid for 2 h at room temperature. The reacting mixture was evaporated under reduced pressure to yield intermediate 3 that was used for the next step without further purification.

To a solution of intermediate 3 in THF was added trimethylamine, decanal and sodium triacetoxyborohydride. The reacting mixture was stirred at room temperature for 24 h and was evaporated under reduced pressure. The resulting product was purified through silica column chromatography to afford GL-1.

Scheme 2: (A) General synthetic routes of single-tail glycolipids using aldehyde containing chains; (B) One example, synthesis of GL-15.

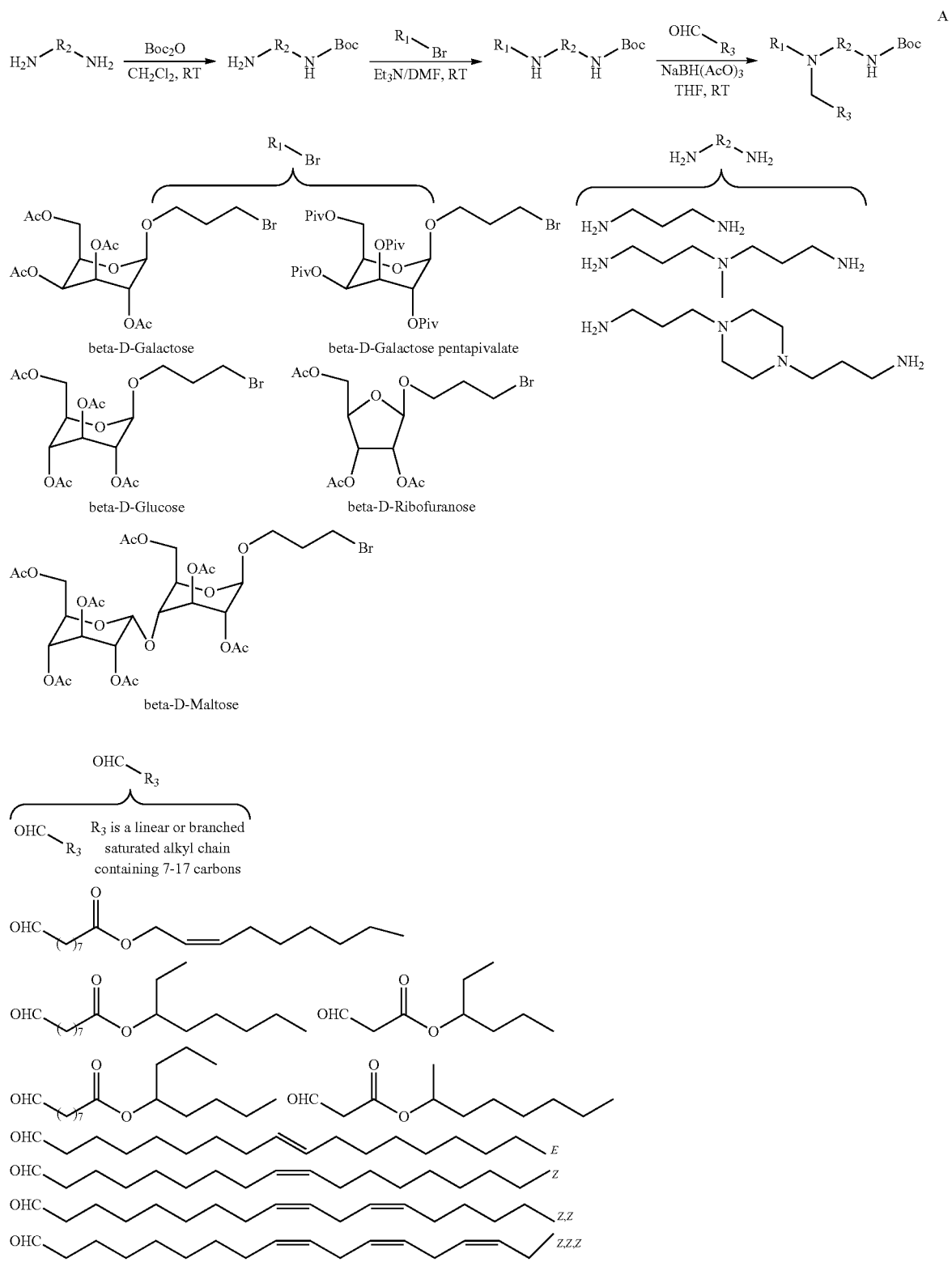

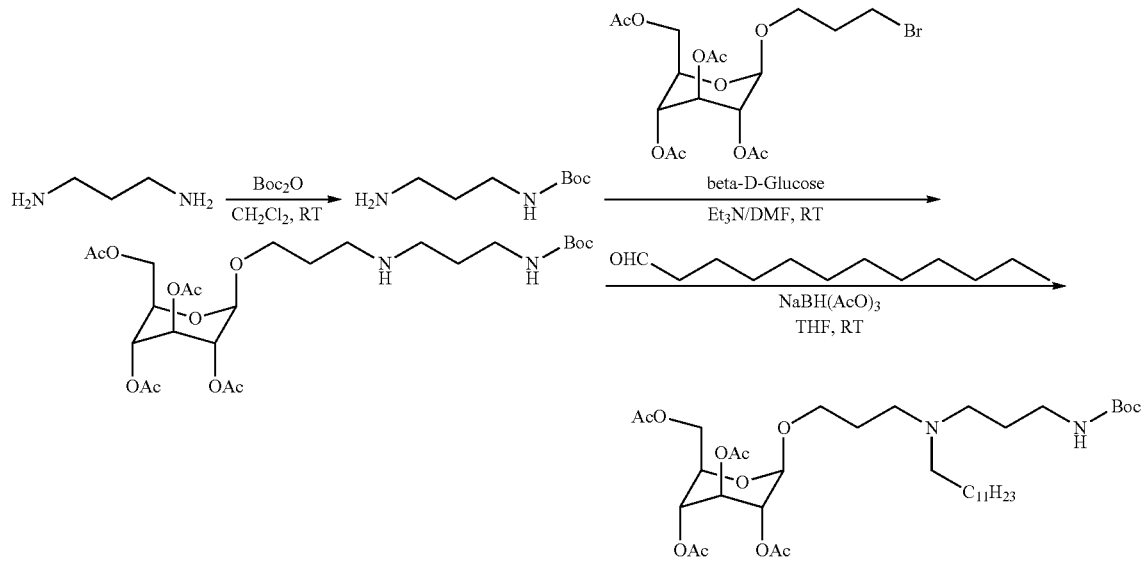

Synthetic Route of GL-15:

To a solution of diamine in CHCl$_3$ was slowly added a solution of Boc$_2$O in CHCl$_3$ via an additional funnel over 2.5 h. The resulting suspension was stirred and NaHCO$_3$ (1N) was slowly added. The organic layer was washed with 1N NaHCO$_3$ and brine, and then dried over solid MgSO$_4$. The solution was then filtered, evaporated and dried under high vacuum in order to afford intermediate 1.

Intermediate 1 was stirred in DMF with beta-D-Glucose derivative and trimethylamine for 48 h. After adding CH$_2$Cl$_2$ the organic phase was washed with water for three times and then dried over solid MgSO$_4$. The solution was then filtered, evaporated and dried under high vacuum. The product was purified by silica column chromatography in order to afford intermediate 2.

To a solution of intermediate 2 in THF was added trimethylamine, dodecyl aldehyde and sodium triacetoxyborohydride. The reacting mixture was stirred at room temperature for 24 h and was evaporated under reduced pressure. The resulting product was purified through silica column chromatography to afford GL-15.

Scheme 3: (A) General synthetic routes of double-tail glycolipids using aldehyde containing chains; (B) One example, synthesis of GL-14.

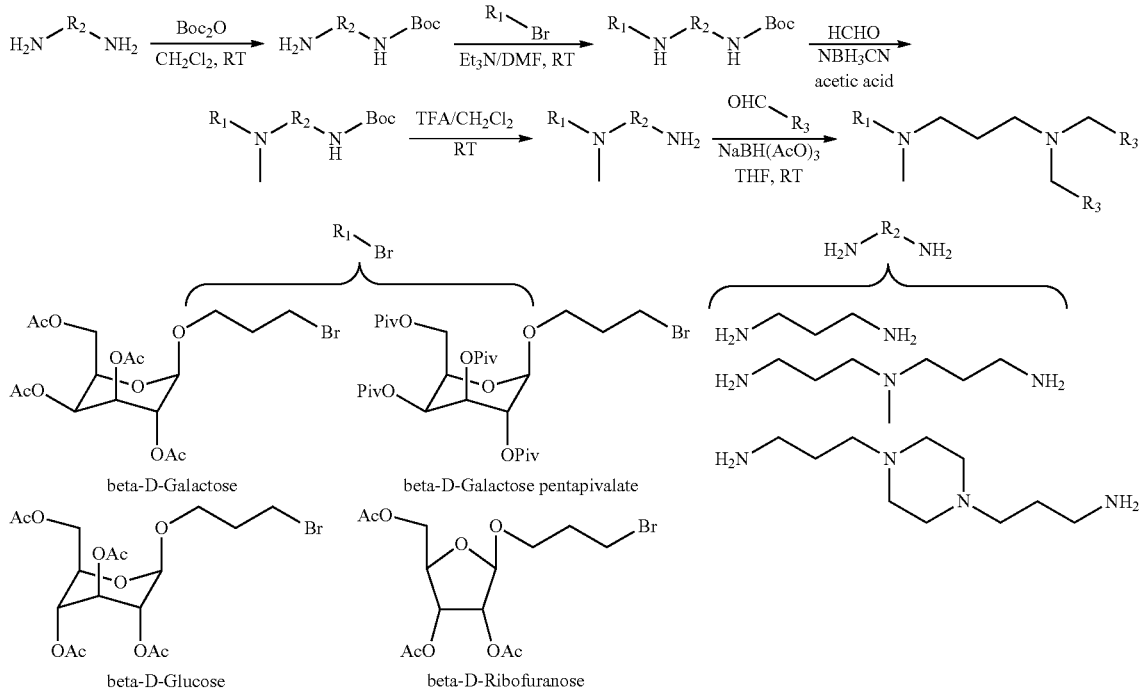

-continued
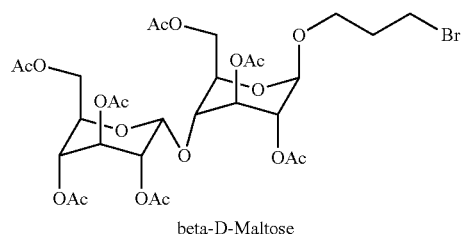
beta-D-Maltose
R₃ is a linear or branched saturated alkyl chain containing 7-17 carbons
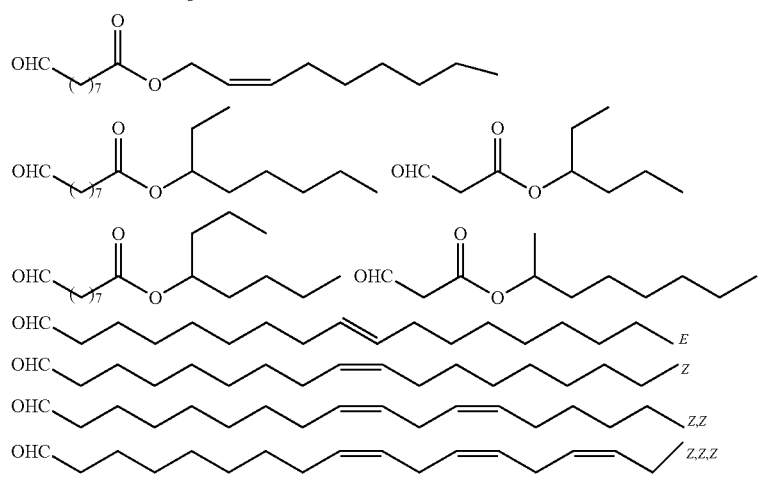
B
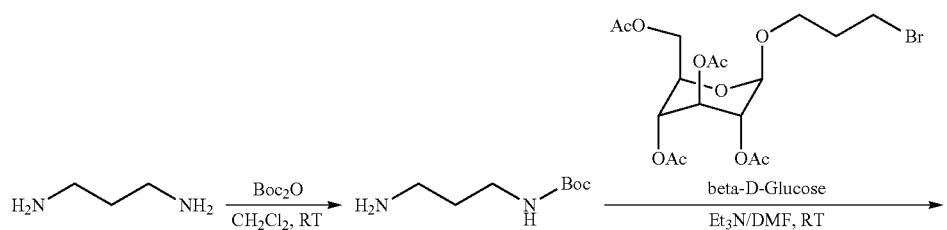
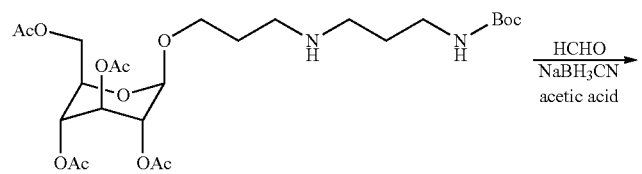
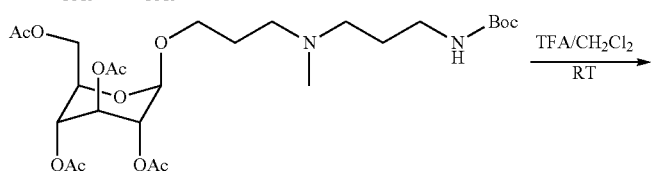
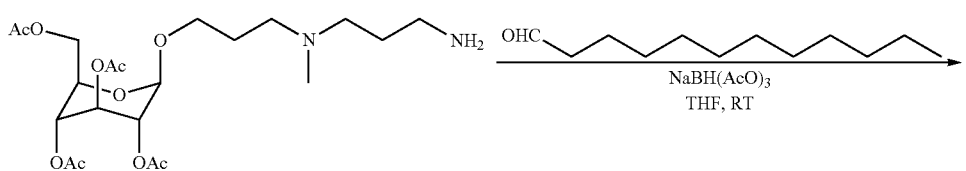

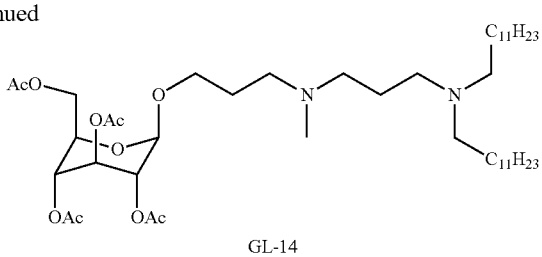

GL-14

Synthetic Route of GL-14:

To a solution of diamine in CHCl$_3$ was slowly added a solution of Boc$_2$O in CHCl$_3$ via an additional funnel over 2.5 h. The resulting suspension was stirred and NaHCO$_3$ (1N) was slowly added. The organic layer was washed with 1N NaHCO$_3$ and brine, and then dried over solid MgSO$_4$. The solution was then filtered, evaporated and dried under high vacuum in order to afford intermediate 1.

Intermediate 1 was stirred in DMF with beta-D-Glucose derivative and trimethylamine for 48 h. After adding CH$_2$Cl$_2$ the organic phase was washed with water for three times and then dried over solid MgSO$_4$. The solution was then filtered, evaporated and dried under high vacuum. The product was purified by silica column chromatography in order to afford intermediate 2.

To a solution of intermediate 2 in THF was added trimethylamine, formaldehyde aqueous and sodium triacetoxyborohydride. The reacting mixture was stirred at room temperature for 24 h and was evaporated under reduced pressure. The resulting product was purified through silica column chromatography to afford intermediate 3.

Intermediate 3 was stirred in excess amount of trifluoroacetic acid for 2 h at room temperature. The reacting mixture was evaporated under reduced pressure to yield intermediate 4 and was used for the next step without further purification.

To a solution of intermediate 4 in THF was added trimethylamine, dodecyl aldehyde and sodium triacetoxyborohydride. The reacting mixture was stirred at room temperature for 24 h and was evaporated under reduced pressure. The resulting product was purified through column to yield GL-14.

Scheme 4

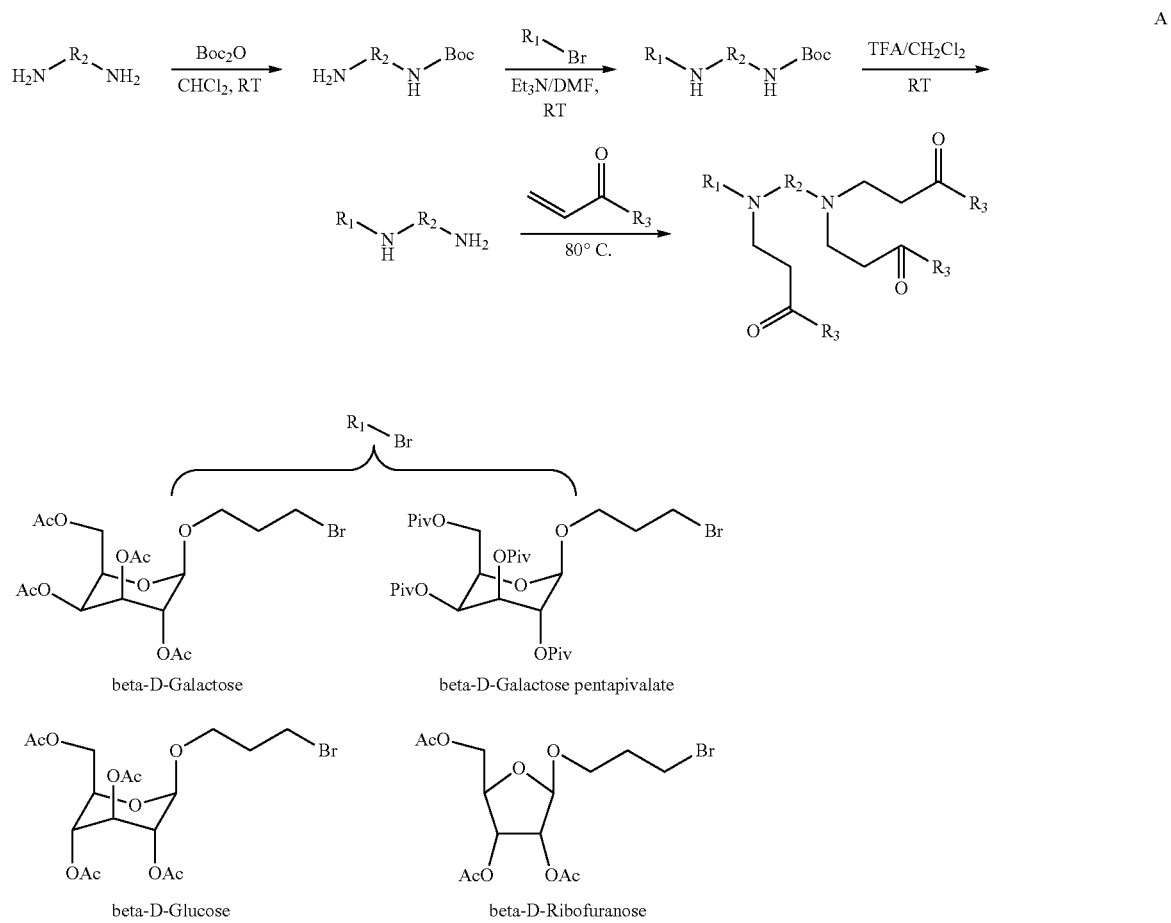

-continued
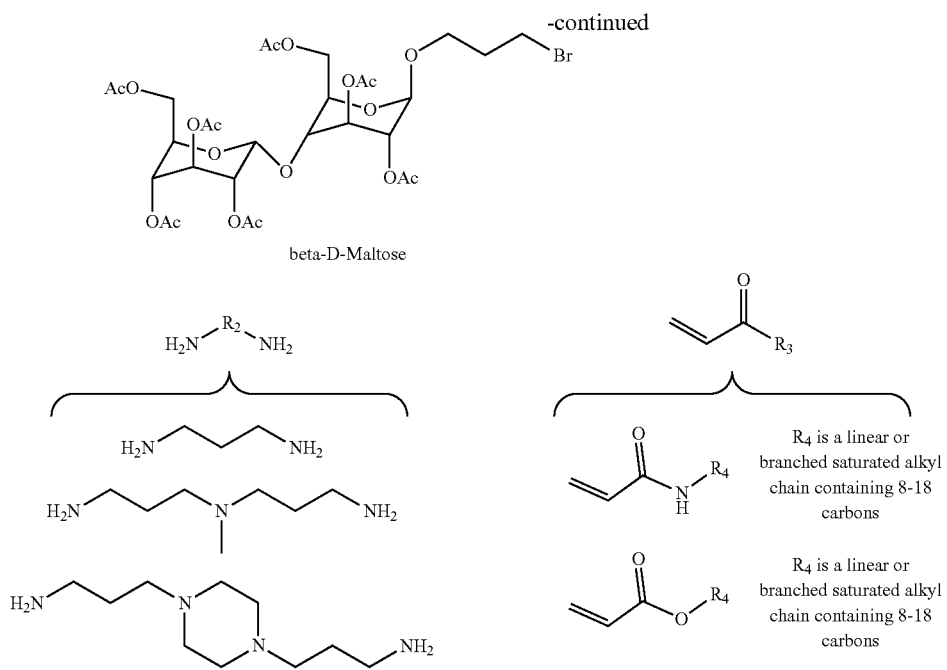
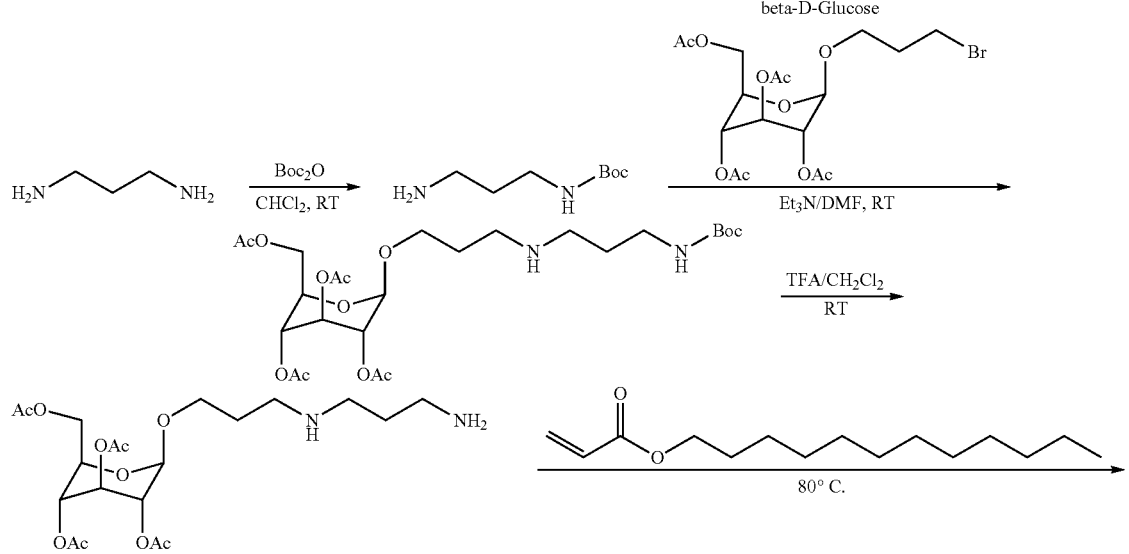
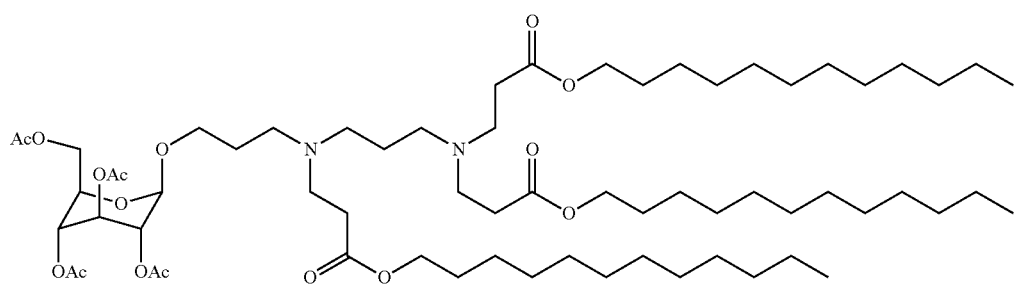
GL-13
(A) General synthetic routes of triple-tail glycolipids using allyl containing chains; (B) One example, synthesis of GL-13.

Synthetic Route of GL-13:

To a solution of diamine in CHCl$_3$ was slowly added a solution of Boc$_2$O in CHCl$_3$ via an additional funnel over 2.5 h. The resulting suspension was stirred and NaHCO$_3$ (1N) was slowly added. The organic layer was washed with 1N NaHCO$_3$ and brine, and then dried over solid MgSO$_4$. The solution was then filtered, evaporated and dried under high vacuum in order to afford intermediate 1.

Intermediate 1 was stirred in DMF with beta-D-Glucose derivative and trimethylamine for 48 h. After adding CH$_2$Cl$_2$ the organic phase was washed with water for three times and then dried over solid MgSO$_4$. The solution was then filtered, evaporated and dried under high vacuum. The product was purified by silica column chromatography in order to afford intermediate 2.

Intermediate 2 was stirred in excess amount of trifluoroacetic acid for 2 h at room temperature. The reacting mixture was evaporated under reduced pressure to yield intermediate 3 that was used for the next step without further purification.

Intermediate 3 was stirred within excess amount of dodecyl acrylate at 120° C. for 8 h. After cooling to room temperature, the reacting mixture was purified through silica column chromatography to afford GL-13.

Scheme 5: (A) General synthetic routes of triple-tail glycolipids using epoxide containing chains; (B) One example, synthesis of GL-19.

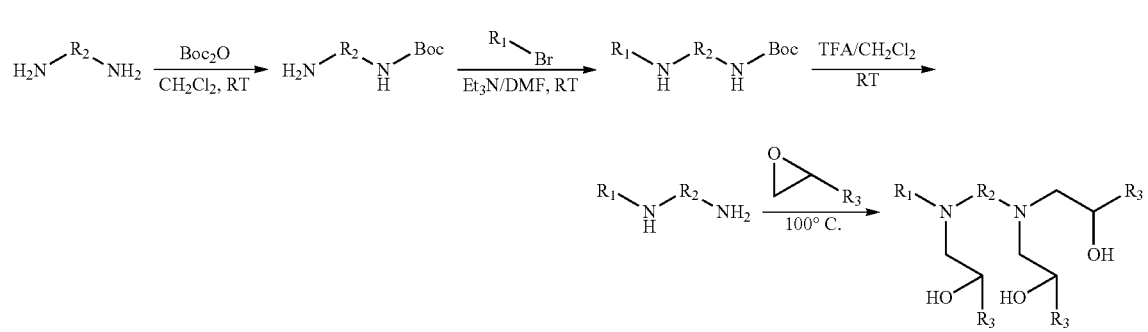

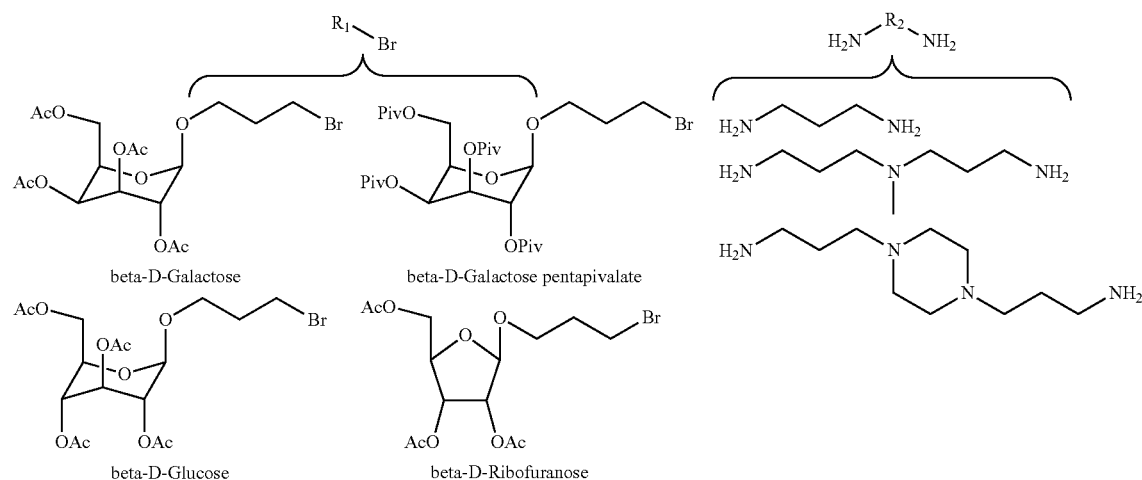

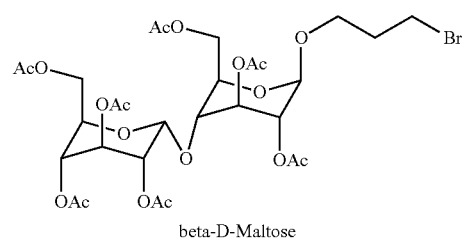

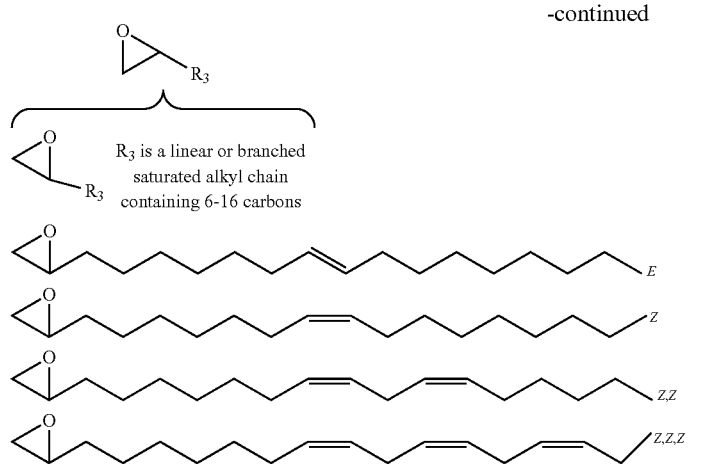

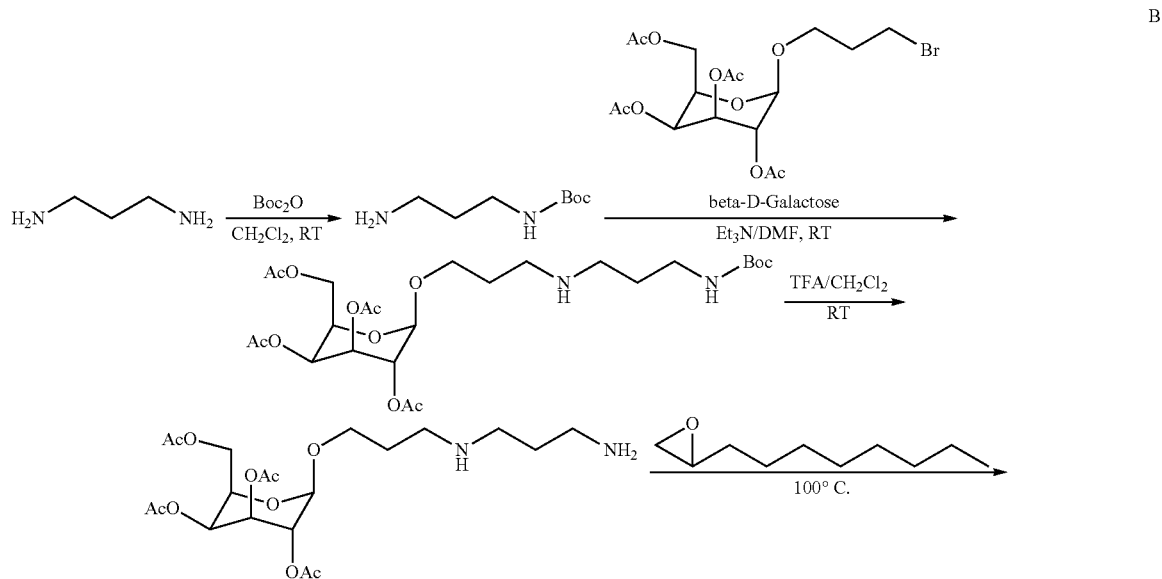

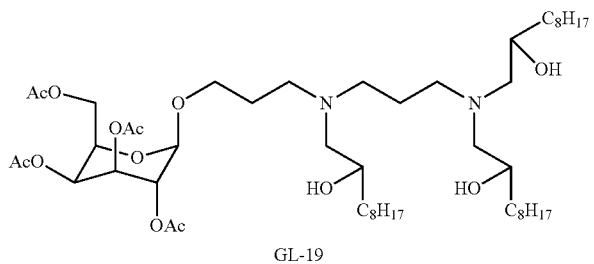

GL-19

Synthetic Route of GL-19:

To a solution of diamine in CHCl$_3$ was slowly added a solution of Boc$_2$O in CHCl$_3$ via an additional funnel over 2.5 h. The resulting suspension was stirred and NaHCO$_3$ (1N) was slowly added. The organic layer was washed with 1N NaHCO$_3$ and brine, and then dried over solid MgSO$_4$. The solution was then filtered, evaporated and dried under high vacuum in order to afford intermediate 1.

Intermediate 1 was stirred in DMF with beta-D-Galactose derivative and trimethylamine for 48 h. After adding CH$_2$Cl$_2$ the organic phase was washed with water for three times and then dried over solid MgSO$_4$. The solution was then filtered, evaporated and dried under high vacuum. The product was purified by silica column chromatography in order to afford intermediate 2.

Intermediate 2 was stirred in excess amount of trifluoroacetic acid for 2 h at room temperature. The reacting mixture was evaporated under reduced pressure to yield intermediate 3 that was used for the next step without further purification.

Intermediate 3 was stirred in ethanol with excess amount of 1,2-epoxydecane at 110° C. for 12 h. After cooling to room temperature, the reacting mixture was purified through silica column chromatography to afford GL-19.

Scheme 6: (A) General synthetic routes of phospholipids using aldehyde containing chains; (B) One example, synthesis of PL-1.
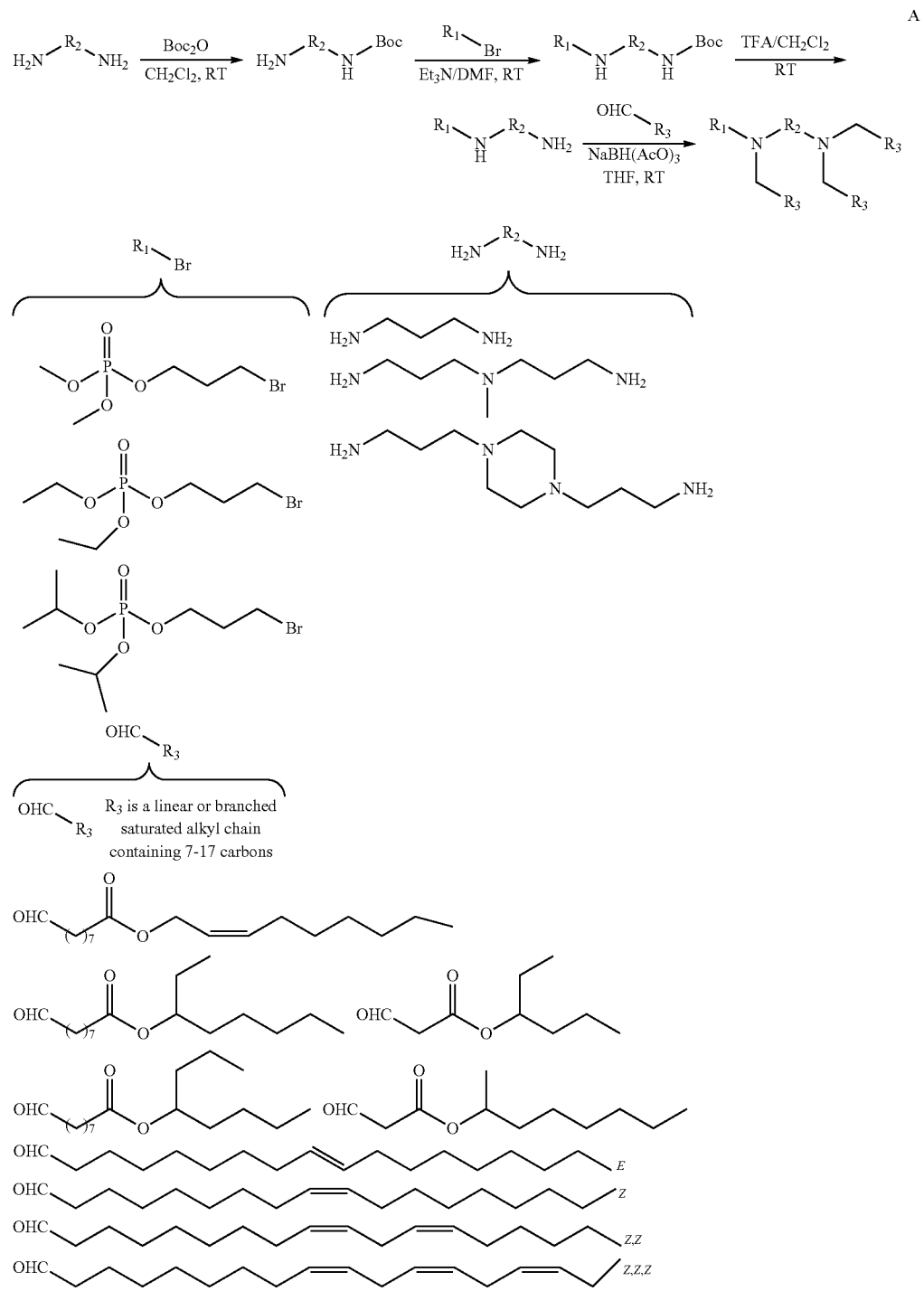
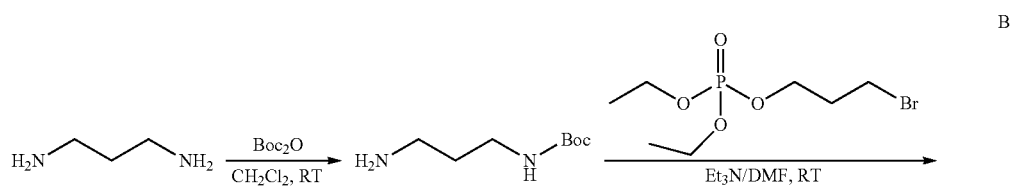

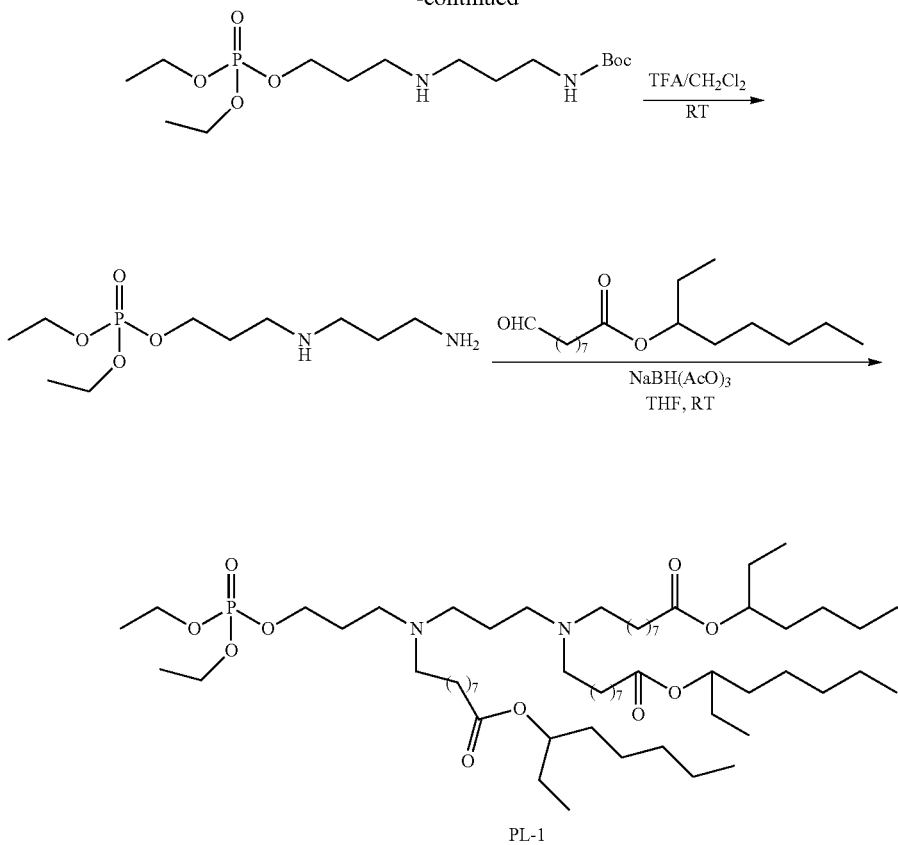

Synthetic Route of PL-1:

To a solution of diamine in CHCl₃ was slowly added a solution of Boc₂O in CHCl₃ via an additional funnel over 2.5 h. The resulting suspension was stirred and NaHCO₃ (1N) was slowly added. The organic layer was washed with 1N NaHCO₃ and brine, and then dried over solid MgSO₄. The solution was then filtered, evaporated and dried under high vacuum in order to afford intermediate 1.

Intermediate 1 was stirred in DMF with Diethyl phosphate derivative and trimethylamine for 48 h. After adding CH₂Cl₂ the organic phase was washed with water for three times and then dried over solid MgSO₄. The solution was then filtered, evaporated and dried under high vacuum. The product was purified by silica column chromatography in order to afford intermediate 2.

Intermediate 2 was stirred in excess amount of trifluoroacetic acid for 2 h at room temperature. The reacting mixture was evaporated under reduced pressure to yield intermediate 3 that was used for the next step without further purification.

To a solution of intermediate 3 in THF was added trimethylamine, branched aldehyde and sodium triacetoxyborohydride. The reacting mixture was stirred at room temperature for 24 h and was evaporated under reduced pressure. The resulting product was purified through silica column chromatography to afford PL-1.

Scheme 7: (A) General synthetic routes of phospholipids using allyl containing chains; (B) One example, synthesis of PL-17.

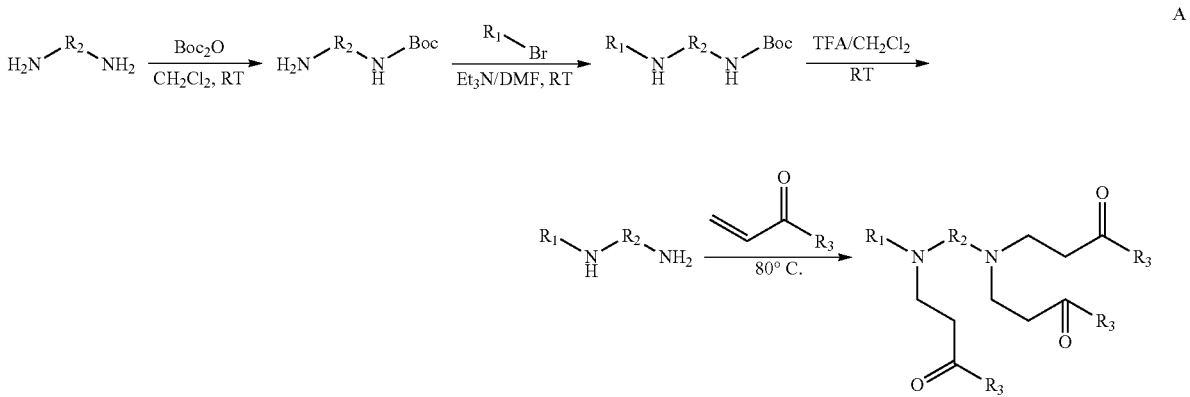

A

-continued

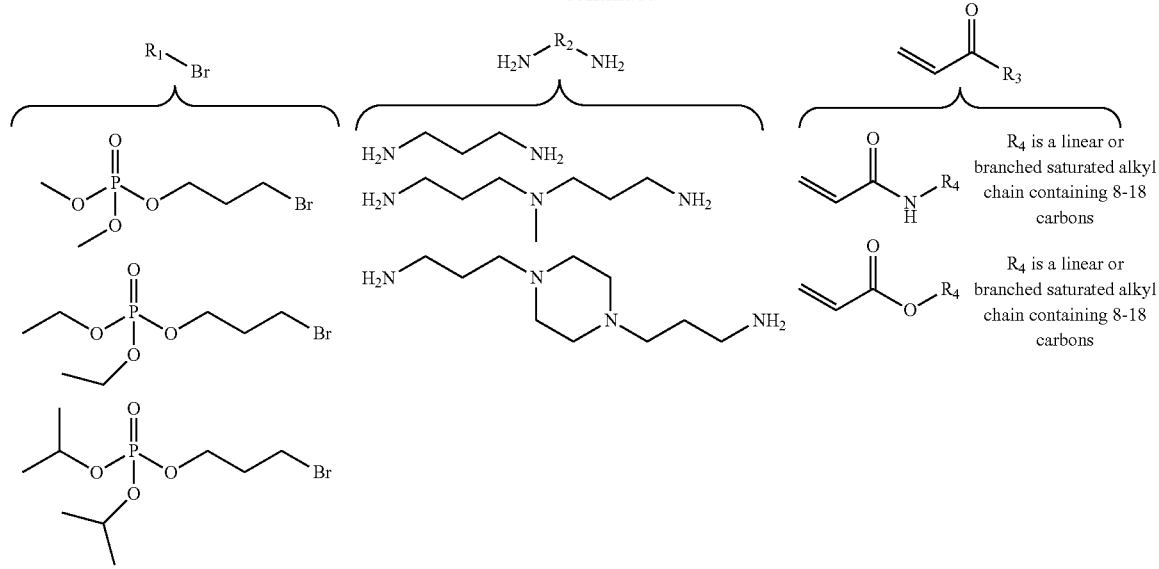

B

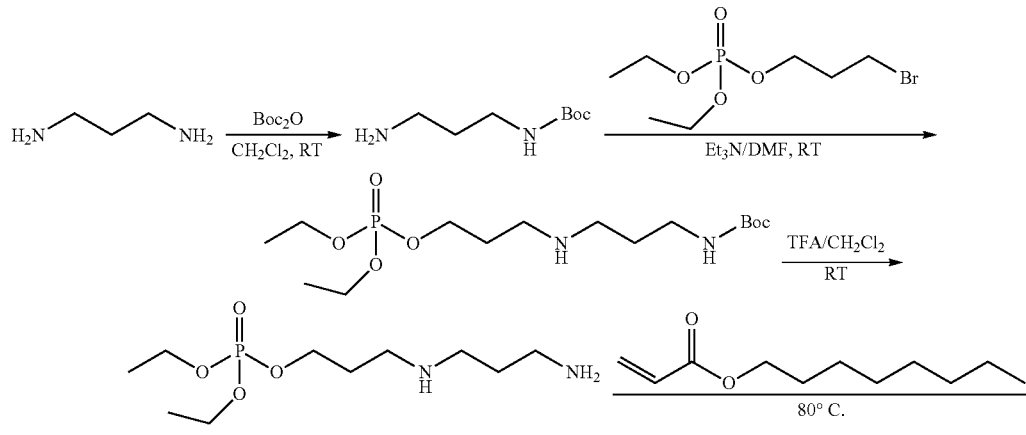

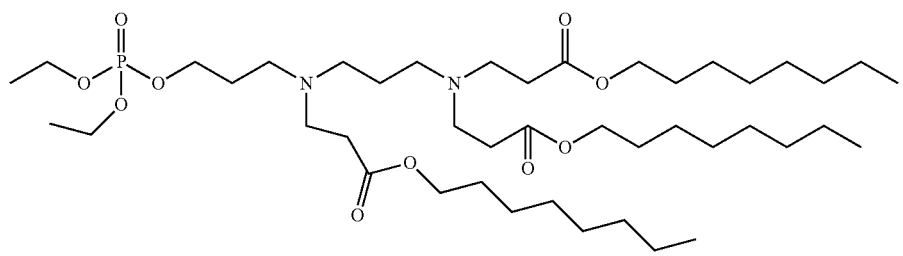

PL-17

Synthetic Route of PL-17:

To a solution of diamine in CHCl$_3$ was slowly added a solution of Boc$_2$O in CHCl$_3$ via an additional funnel over 2.5 h. The resulting suspension was stirred and NaHCO$_3$ (1N) was slowly added. The organic layer was washed with 1N NaHCO$_3$ and brine, and then dried over solid MgSO$_4$. The solution was then filtered, evaporated and dried under high vacuum in order to afford intermediate 1.

Intermediate 1 was stirred in DMF with Diethyl phosphate derivative and trimethylamine for 48 h. After adding CH$_2$Cl$_2$ the organic phase was washed with water for three times and then dried over solid MgSO$_4$. The solution was then filtered, evaporated and dried under high vacuum. The product was purified by silica column chromatography in order to afford intermediate 2.

Intermediate 2 was stirred in excess amount of trifluoroacetic acid for 2 h at room temperature. The reacting mixture was evaporated under reduced pressure to yield intermediate 3 that was used for the next step without further purification.

Intermediate 3 was stirred within excess amount of n-Octyl acrylate at 120° C. for 8 h. After cooling to room temperature, the reacting mixture was purified through silica column chromatography to afford PL-17.

Scheme 8: (A) General synthetic routes of phospholipids using epoxide containing chains; (B) One example, synthesis of PL-18.
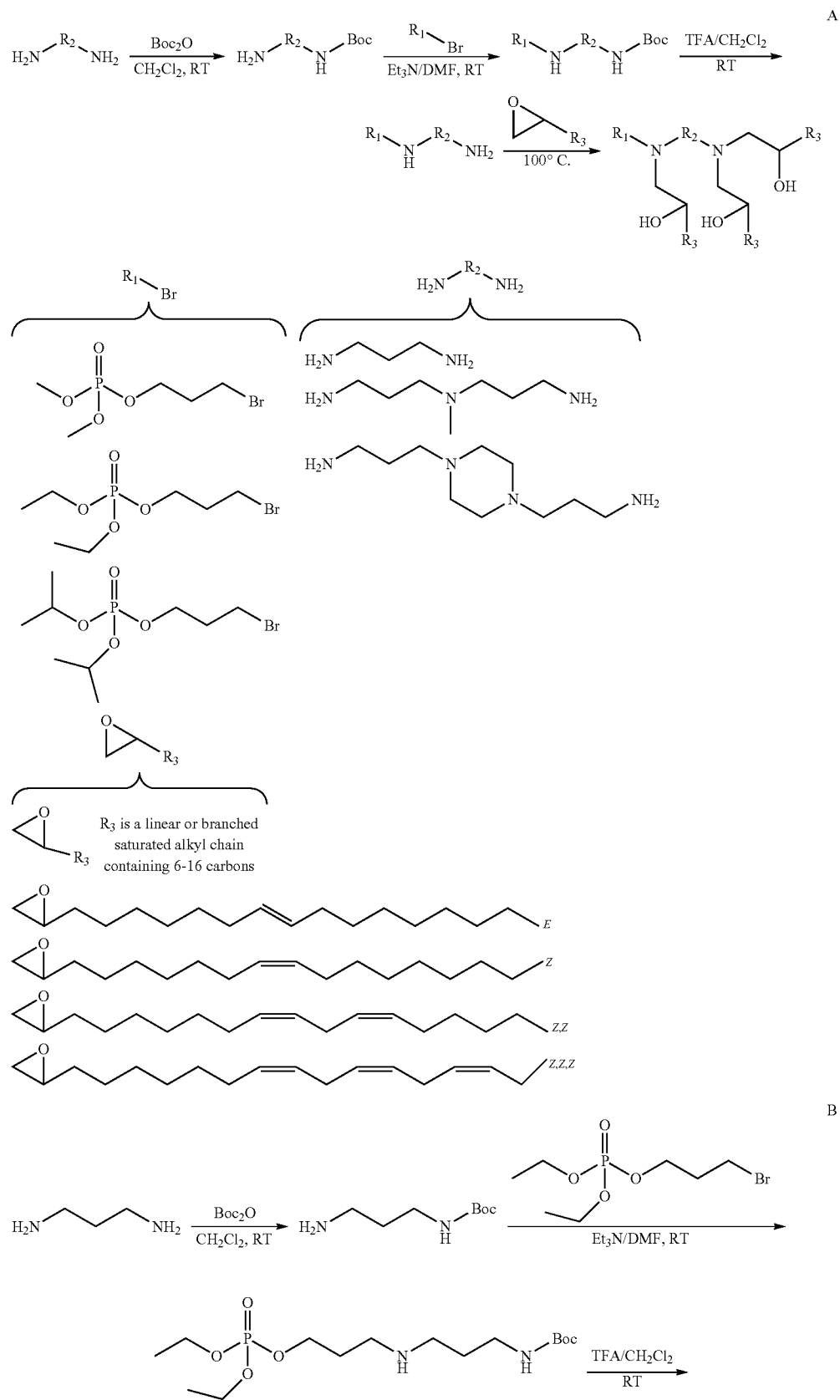

-continued

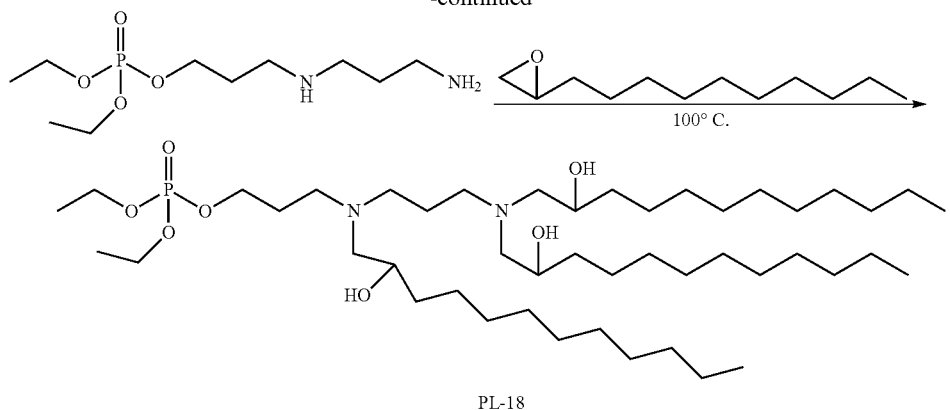

PL-18

Synthetic Route of PL-18:

To a solution of diamine in CHCl$_3$ was slowly added a solution of Boc$_2$O in CHCl$_3$ via an additional funnel over 2.5 h. The resulting suspension was stirred and NaHCO$_3$ (1N) was slowly added. The organic layer was washed with 1N NaHCO$_3$ and brine, and then dried over solid MgSO$_4$. The solution was then filtered, evaporated and dried under high vacuum in order to afford intermediate 1.

Intermediate 1 was stirred in DMF with Diethyl phosphate derivative and trimethylamine for 48 h. After adding CH$_2$Cl$_2$ the organic phase was washed with water for three times and then dried over solid MgSO$_4$. The solution was then filtered, evaporated and dried under high vacuum. The product was purified by silica column chromatography in order to afford intermediate 2.

Intermediate 2 was stirred in excess amount of trifluoroacetic acid for 2 h at room temperature. The reacting mixture was evaporated under reduced pressure to yield intermediate 3 that was used for the next step without further purification.

Scheme 9

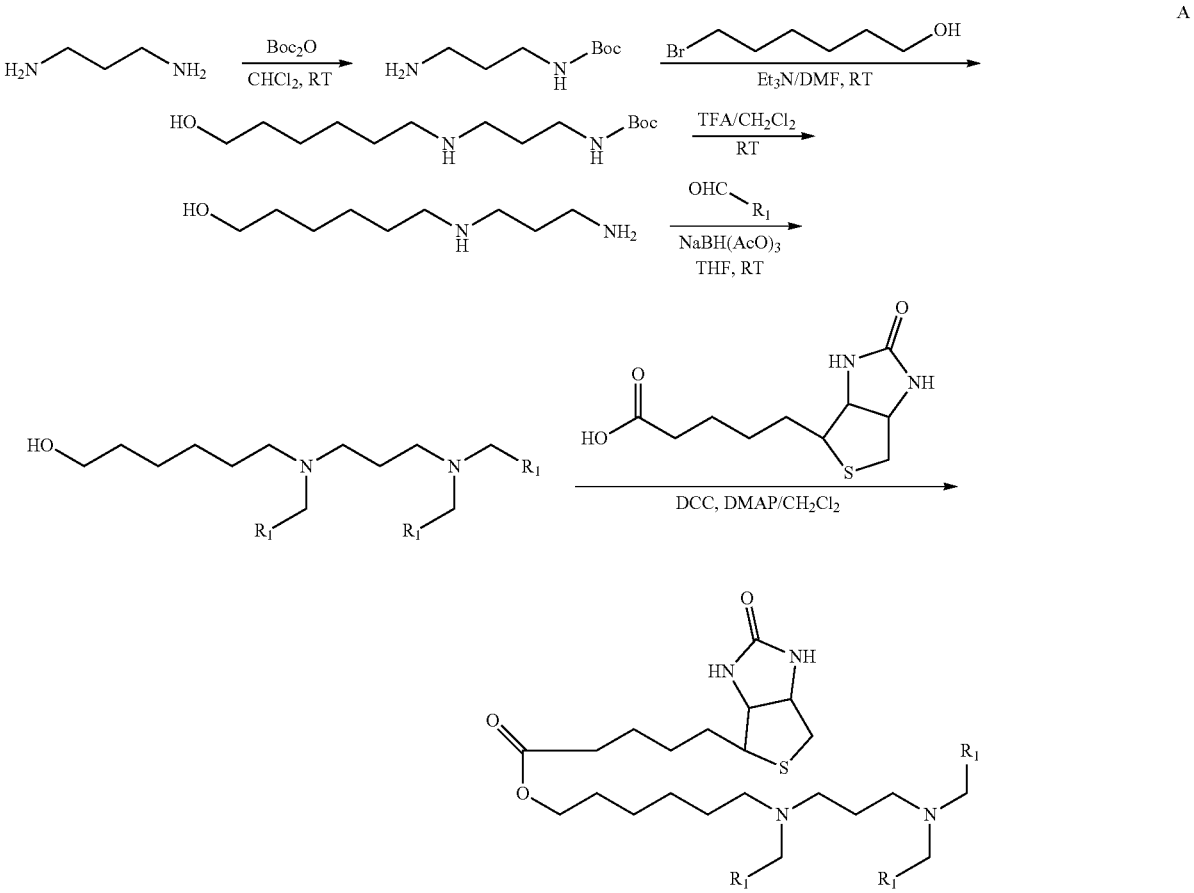

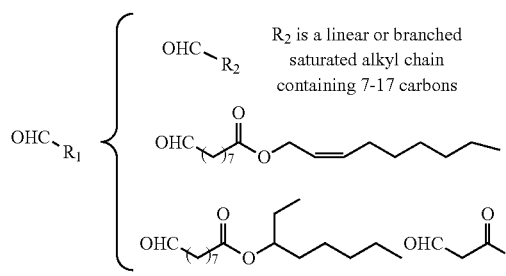
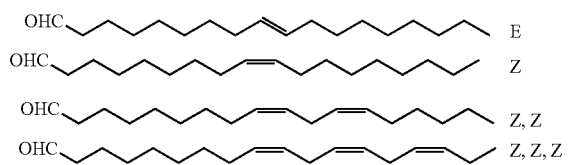
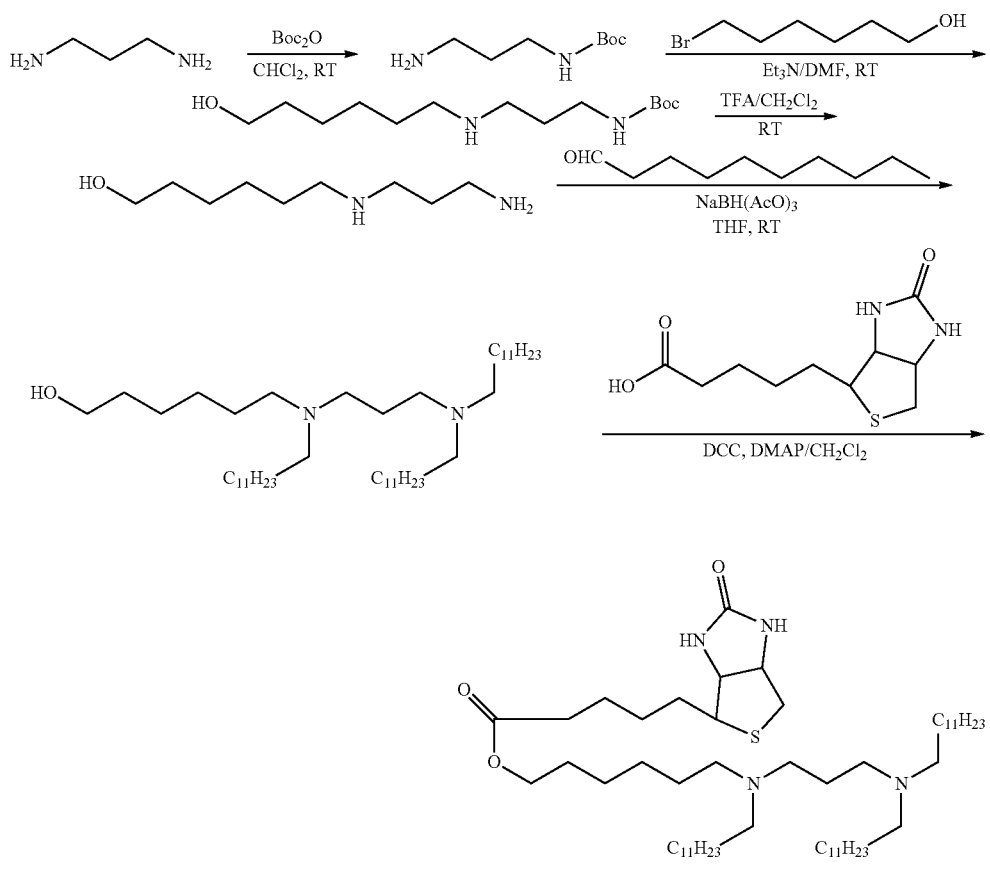

(A) General synthetic routes of biotin-lipids using aldehyde containing chains; (B) One example, synthesis of VL-1.

Synthetic Route of VL-1:

To a solution of diamine in $CHCl_3$ was slowly added a solution of $Boc_2O$ in $CHCl_3$ via an additional funnel over 2.5 h. The resulting suspension was stirred and $NaHCO_3$ (1N) was slowly added. The organic layer was washed with 1N $NaHCO_3$ and brine, and then dried over solid $MgSO_4$. The solution was then filtered, evaporated and dried under high vacuum in order to afford intermediate 1.

Intermediate 1 was stirred in DMF with 6-bromo-1-hexanol and trimethylamine for 48 h. After adding $CH_2Cl_2$ the organic phase was washed with water for three times and then dried over solid $MgSO_4$. The solution was then filtered, evaporated and dried under high vacuum. The product was purified by silica column chromatography in order to afford intermediate 2.

Intermediate 2 was stirred in excess amount of trifluoroacetic acid for 2 h at room temperature. The reacting mixture was evaporated under reduced pressure to yield intermediate 3 that was used for the next step without further purification.

To a solution of intermediate 3 in THF was added trimethylamine, decanal and sodium triacetoxyborohydride. The reacting mixture was stirred at room temperature for 24 h and was evaporated under reduced pressure. The resulting product was purified through silica column chromatography to afford intermediate 4.

Intermediate 4 and biotin were stirred in $CH_2Cl_2$ at room temperature followed by adding 1-(3-Dimethylaminopropyl)-3-ethylcarbodiimide hydrochloride and 4-dimethylaminopyridine for 24 h. After adding $CH_2Cl_2$ the organic phase was washed with water for three times and then dried over solid $MgSO_4$. The solution was then filtered, evaporated and dried under high vacuum. The product was purified by silica column chromatography in order to afford VL-1.

Scheme 10: (A) General synthetic routes of biotin-lipids using allyl containing chains; (B) One example, synthesis of VL-7.
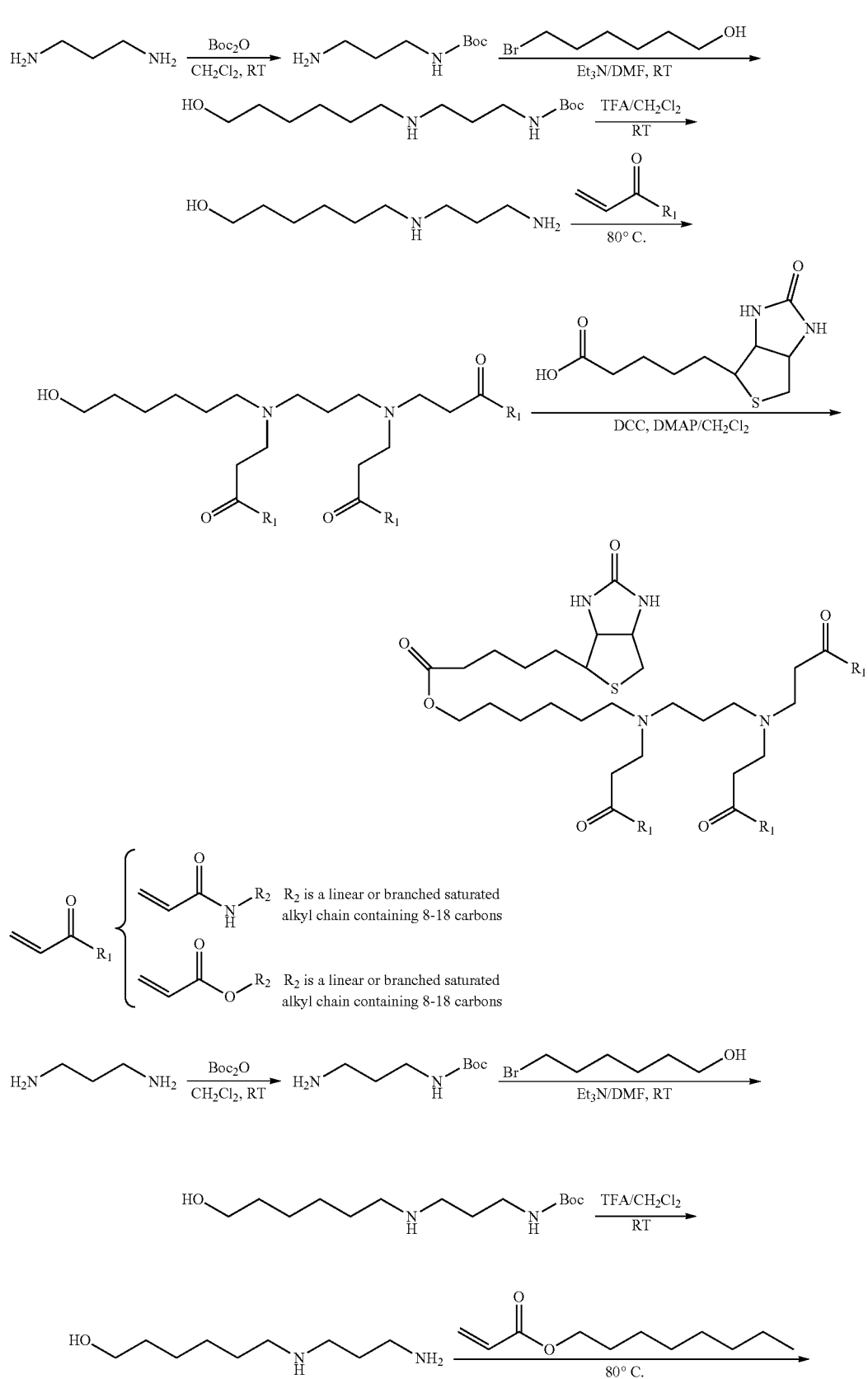

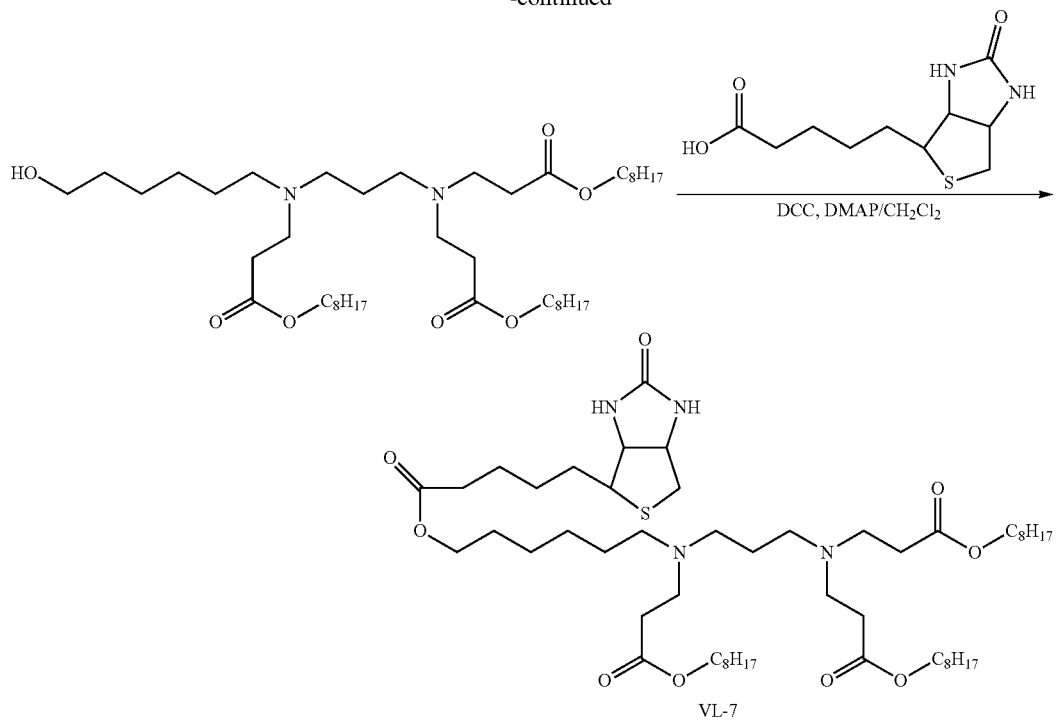

Synthetic Route of VL-7:

To a solution of diamine in CHCl₃ was slowly added a solution of Boc₂O in CHCl₃ via an additional funnel over 2.5 h. The resulting suspension was stirred and NaHCO₃ (1N) was slowly added. The organic layer was washed with 1N NaHCO₃ and brine, and then dried over solid MgSO₄. The solution was then filtered, evaporated and dried under high vacuum in order to afford intermediate 1.

Intermediate 1 was stirred in DMF with 6-bromo-1-hexanol and trimethylamine for 48 h. After adding CH₂Cl₂ the organic phase was washed with water for three times and then dried over solid MgSO₄. The solution was then filtered, evaporated and dried under high vacuum. The product was purified by silica column chromatography in order to afford intermediate 2.

Intermediate 2 was stirred in excess amount of trifluoroacetic acid for 2 h at room temperature. The reacting mixture was evaporated under reduced pressure to yield intermediate 3 that was used for the next step without further purification.

Intermediate 3 was stirred within excess amount of n-Octyl acrylate at 120° C. for 8 h. After cooling to room temperature, the reacting mixture was purified through silica column chromatography to afford intermediate 4.

Intermediate 4 and biotin were stirred in CH₂Cl₂ at room temperature followed by adding 1-(3-Dimethylaminopropyl)-3-ethylcarbodiimide hydrochloride and 4-dimethylaminopyridine for 24 h. After adding CH₂Cl₂ the organic phase was washed with water for three times and then dried over solid MgSO₄. The solution was then filtered, evaporated and dried under high vacuum. The product was purified by silica column chromatography in order to afford VL-7.

Scheme 11: (A) General synthetic routes of biotin-lipids using aldehyde containing chains; (B) One example, synthesis of VL-2.

A

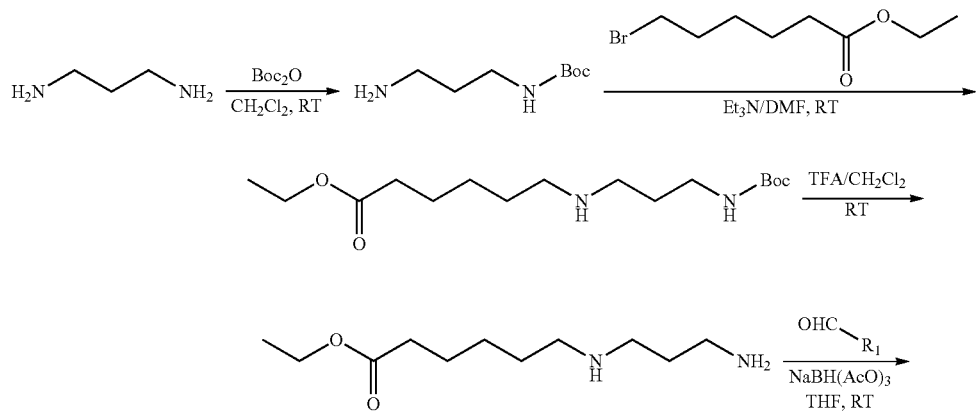

-continued
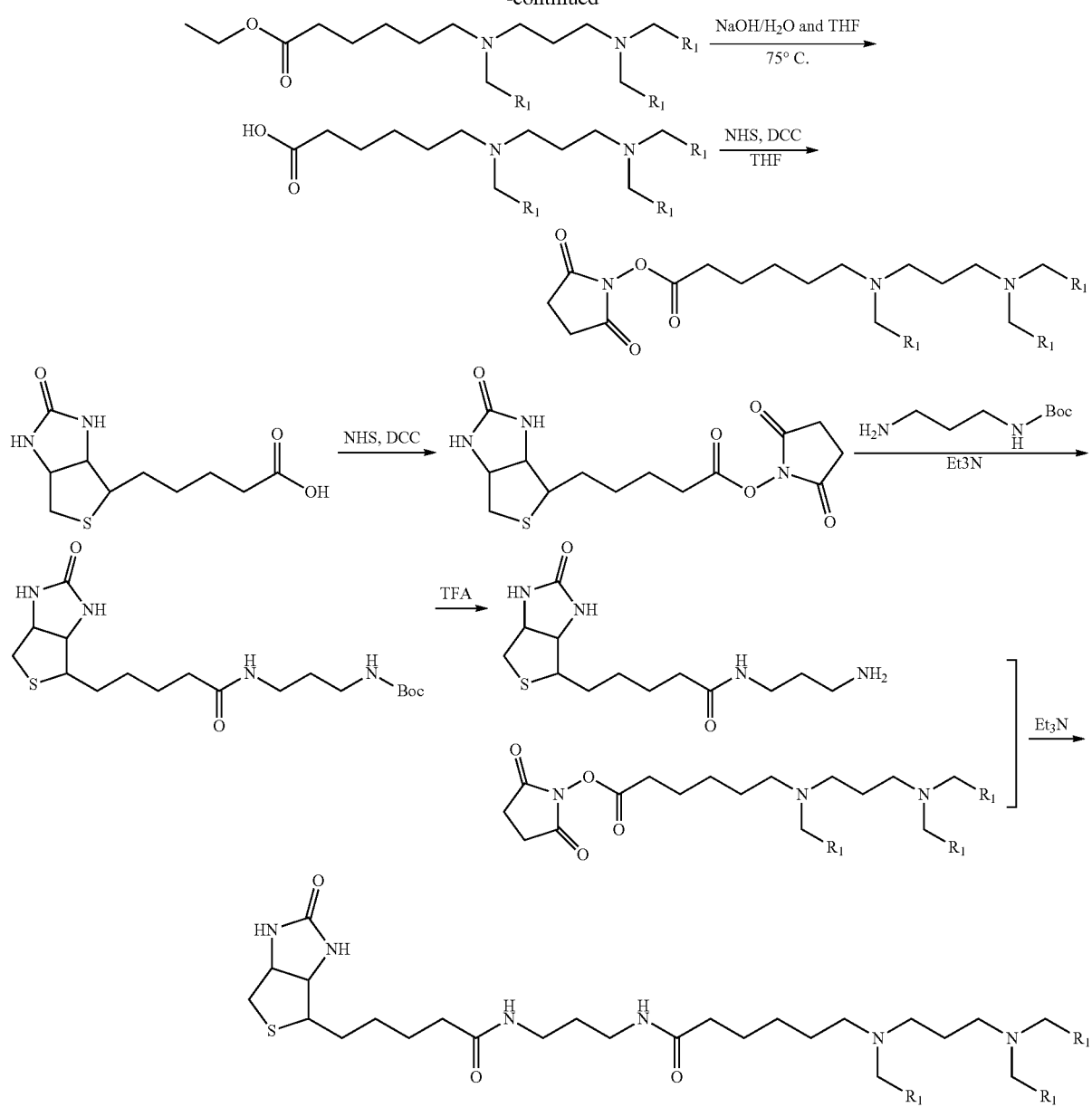
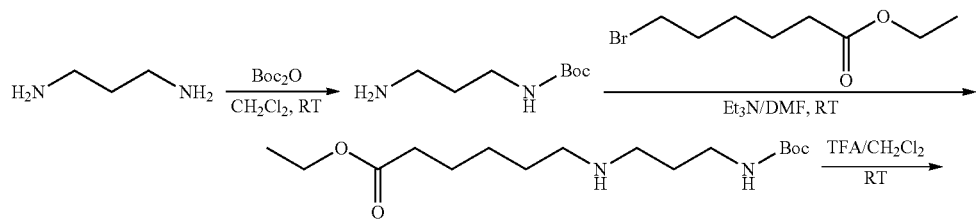

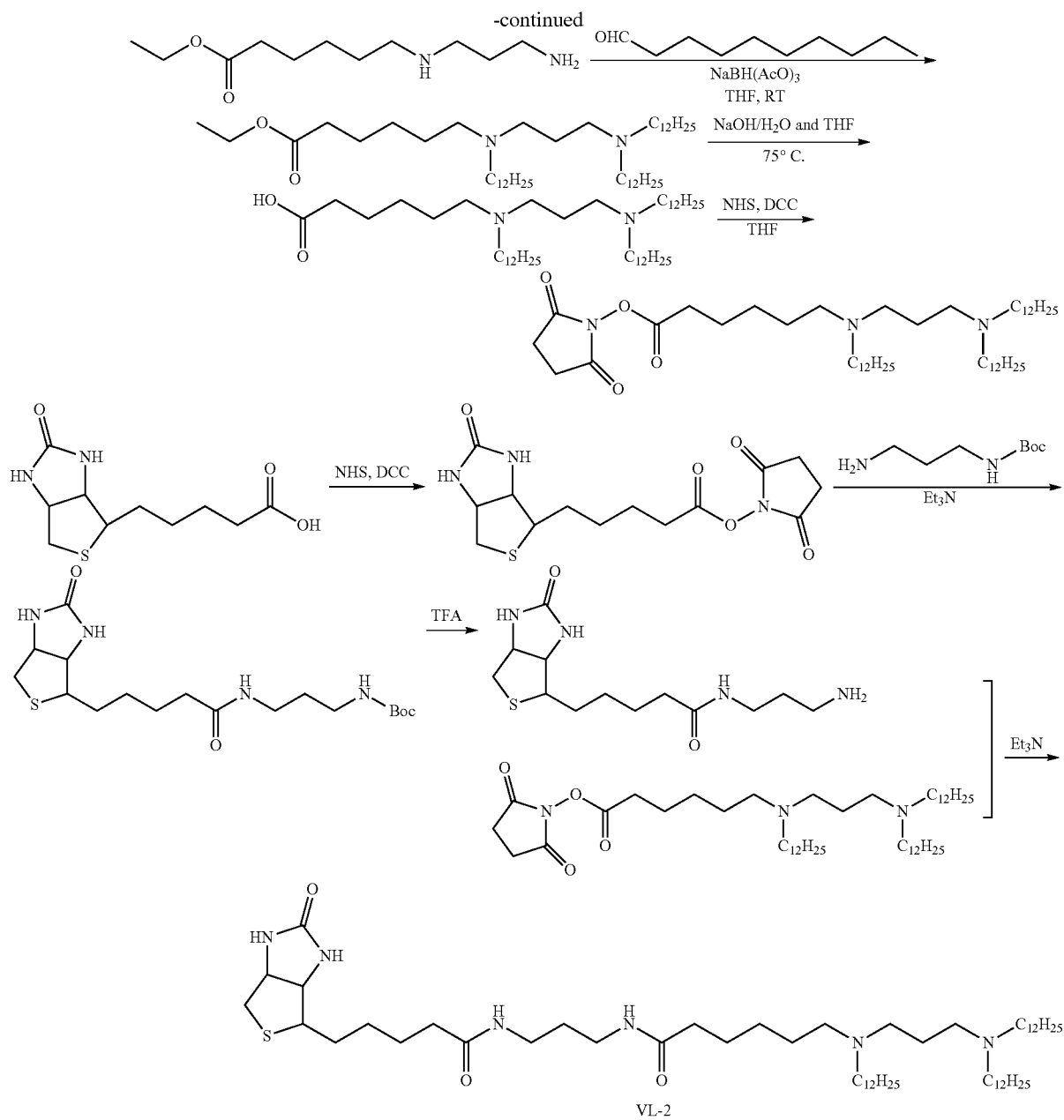

Synthetic Route of VL-2:

To a solution of diamine in CHCl₃ was slowly added a solution of Boc₂O in CHCl₃ via an additional funnel over 2.5 h. The resulting suspension was stirred and NaHCO₃ (1N) was slowly added. The organic layer was washed with 1N NaHCO₃ and brine, and then dried over solid MgSO₄. The solution was then filtered, evaporated and dried under high vacuum in order to afford intermediate 1.

Intermediate 1 was stirred in DMF with 6-Bromohexanoic acid ethyl ester and trimethylamine for 48 h. After adding CH₂Cl₂ the organic phase was washed with water for three times and then dried over solid MgSO₄. The solution was then filtered, evaporated and dried under high vacuum. The product was purified by silica column chromatography in order to afford intermediate 2.

Intermediate 2 was stirred in excess amount of trifluoroacetic acid for 2 h at room temperature. The reacting mixture was evaporated under reduced pressure to yield intermediate 3 that was used for the next step without further purification.

To a solution of intermediate 3 in THF was added trimethylamine, decanal and sodium triacetoxyborohydride. The reacting mixture was stirred at room temperature for 24 h and was evaporated under reduced pressure. The resulting product was purified through silica column chromatography to afford intermediate 4.

To a solution of intermediate 4 in THF was added methanol and 1 M NaOH aqueous. The resulting mixture was stirred at 70° C. for 5 h and was evaporated under reduced pressure. The resulting mixture was purified through silica column chromatography to afford intermediate 5.

To intermediate 5 in CH₂Cl₂ was added N-Hydroxysuccinimide, 1-(3-Dimethylaminopropyl)-3-ethylcarbodiimide hydrochloride and 4-dimethylaminopyridine. The reacting mixture was stirred at room temperature for 12 h. After filtration, the resulting solution of intermediate 6 was collected and used for the next step.

To biotin in CH$_2$Cl$_2$ was added N-Hydroxysuccinimide, 1-(3-Dimethylaminopropyl)-3-ethylcarbodiimide hydrochloride and 4-dimethylaminopyridine. The reacting mixture was stirred at room temperature for 12 h. After filtration, the resulting solution of intermediate 7 was collected and used for the next step.

To the solution of intermediate 7 was added trimethylamine and intermediate 1 in THF. The resulting mixture was stirred at room temperature for 12 h. After adding CH$_2$Cl$_2$, the organic phase was washed with water for three times and then dried over solid MgSO$_4$. The solution was then filtered, evaporated and dried under high vacuum. The product was purified by silica column chromatography in order to afford intermediate 8.

Intermediate 8 was stirred in excess amount of trifluoroacetic acid for 2 h at room temperature. The reacting mixture was evaporated under reduced pressure to yield intermediate 9 and was used for the next step without further purification.

Intermediate 9 was dissolved in the solution of intermediate 6, followed by adding trimethylamine. The resulting mixture was stirred at room temperature for 12 h. After adding CH$_2$Cl$_2$, the organic phase was washed with water for three times and then dried over solid MgSO$_4$. The solution was then filtered, evaporated and dried under high vacuum. The product was purified by silica column chromatography in order to afford VL-2.

Scheme 12: (A) General synthetic routes of Vitamin B-lipids using aldehyde containing chains; (B) One example, synthesis of VL-3.

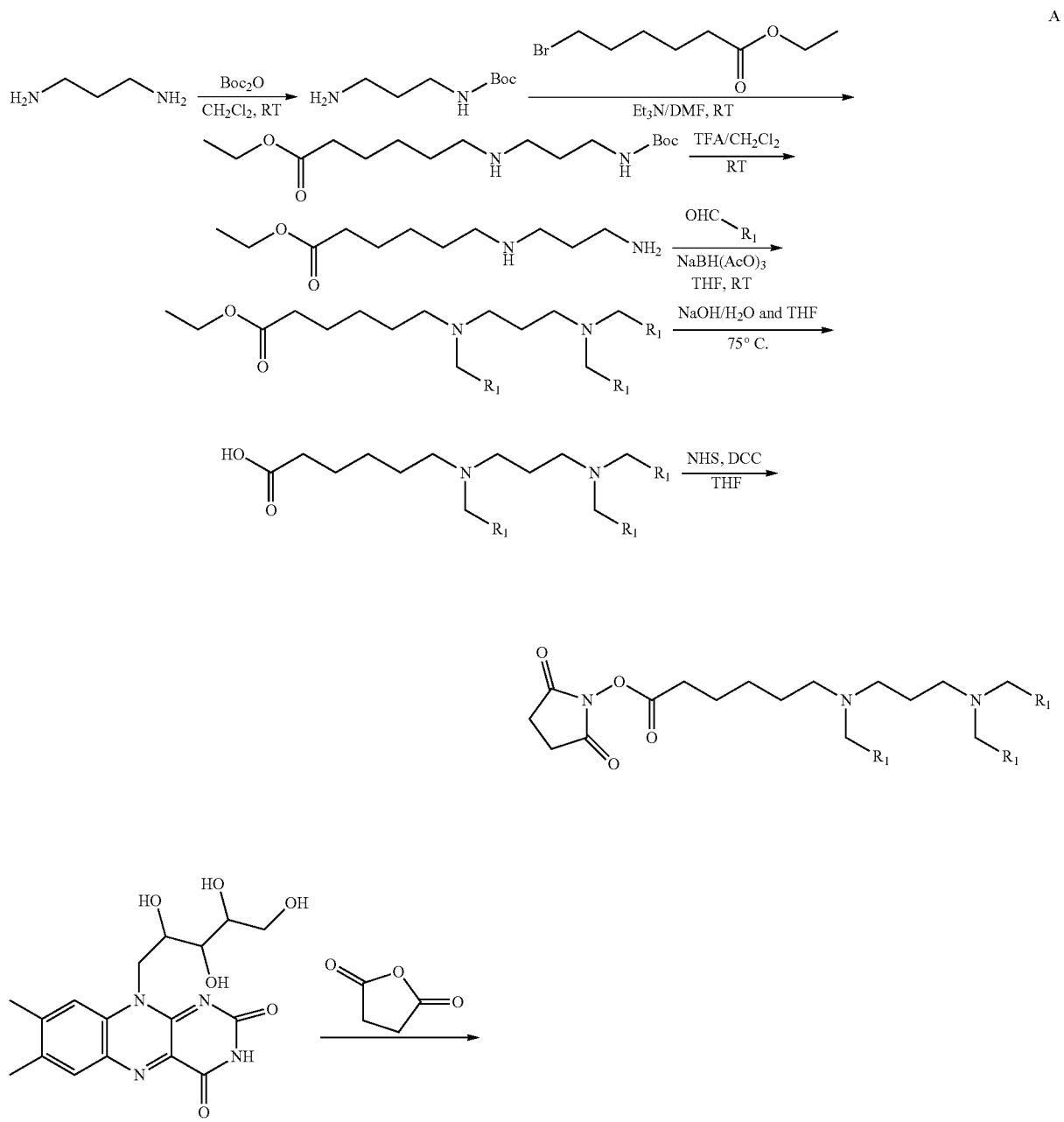

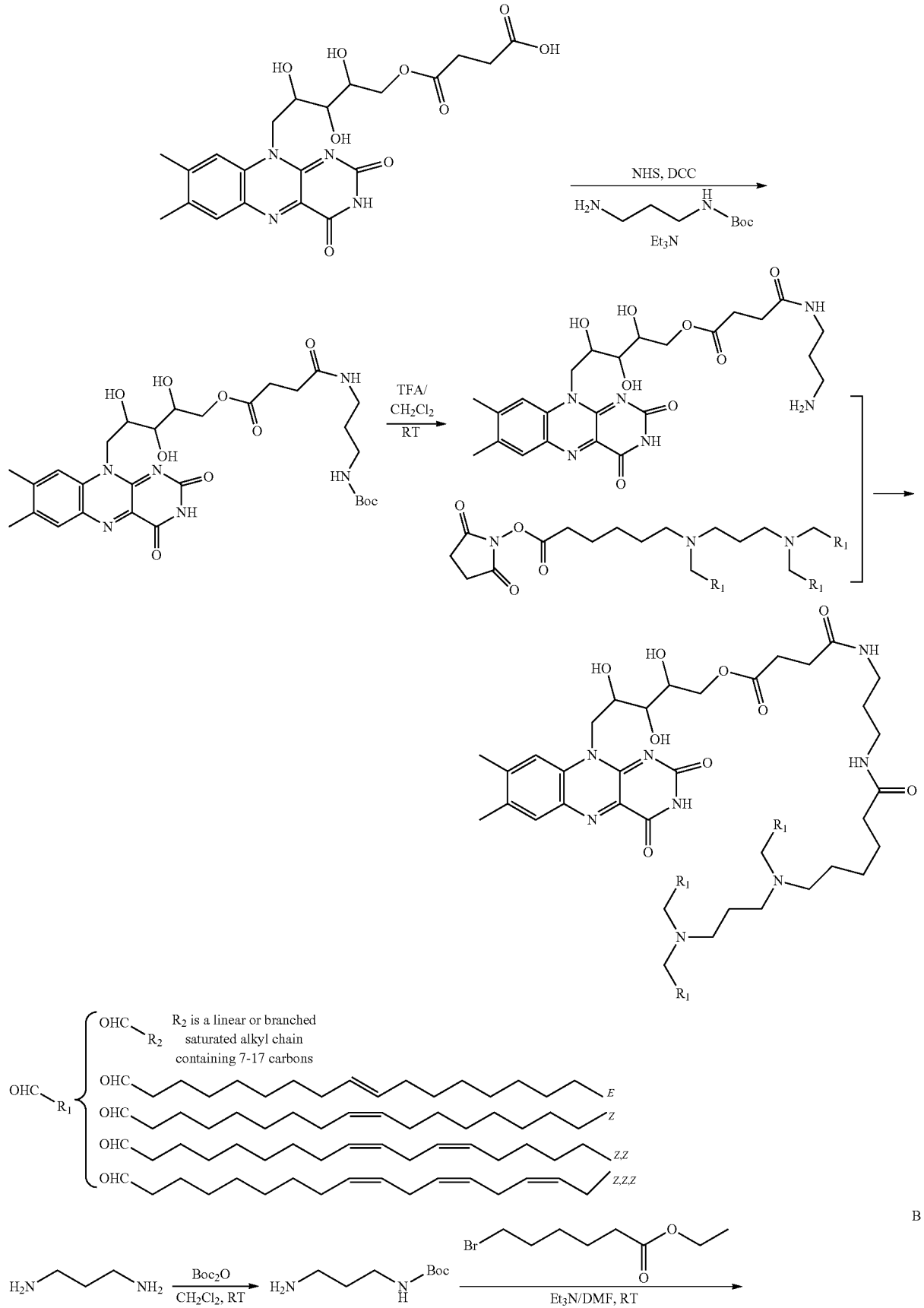

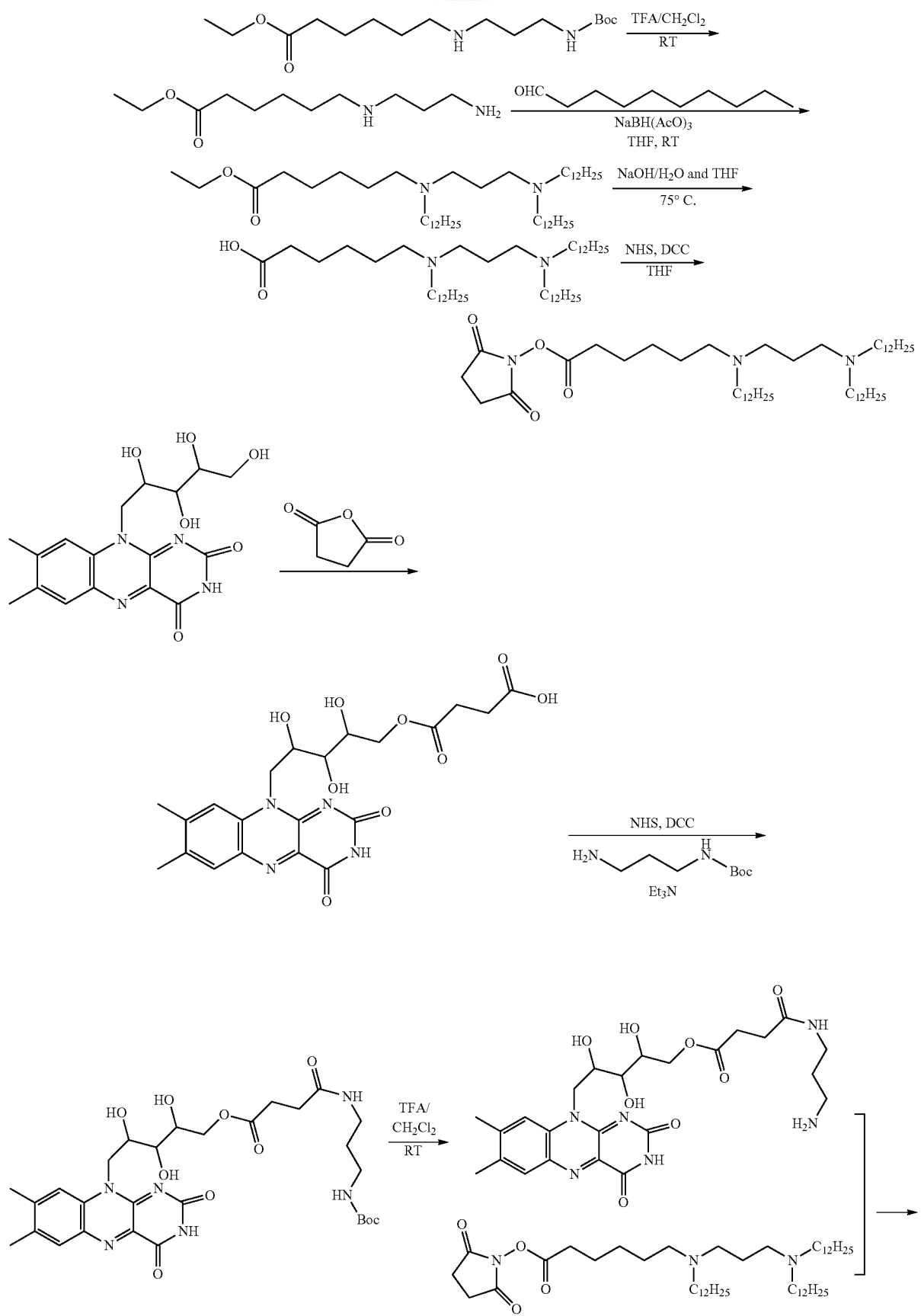
-continued

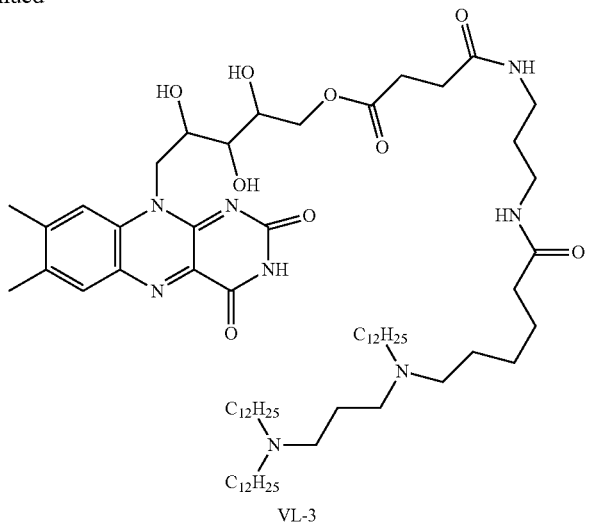

VL-3

Synthetic Route of VL-3:

To a solution of diamine in CHCl₃ was slowly added a solution of Boc₂O in CHCl₃ via an additional funnel over 2.5 h. The resulting suspension was stirred and NaHCO₃ (1N) was slowly added. The organic layer was washed with 1N NaHCO₃ and brine, and then dried over solid MgSO₄. The solution was then filtered, evaporated and dried under high vacuum in order to afford intermediate 1.

Intermediate 1 was stirred in DMF with 6-Bromohexanoic acid ethyl ester and trimethylamine for 48 h. After adding CH₂Cl₂ the organic phase was washed with water for three times and then dried over solid MgSO₄. The solution was then filtered, evaporated and dried under high vacuum. The product was purified by silica column chromatography in order to afford intermediate 2.

Intermediate 2 was stirred in excess amount of trifluoroacetic acid for 2 h at room temperature. The reacting mixture was evaporated under reduced pressure to yield intermediate 3 that was used for the next step without further purification.

To a solution of intermediate 3 in THF was added trimethylamine, decanal and sodium triacetoxyborohydride. The reacting mixture was stirred at room temperature for 24 h and was evaporated under reduced pressure. The resulting product was purified through silica column chromatography to afford intermediate 4.

To a solution of intermediate 4 in THF was added methanol and 1 M NaOH aqueous. The resulting mixture was stirred at 70° C. for 5 h and was evaporated under reduced pressure. The resulting mixture was purified through silica column chromatography to afford intermediate 5.

To intermediate 5 in CH₂Cl₂ was added N-Hydroxysuccinimide, 1-(3-Dimethylaminopropyl)-3-ethylcarbodiimide hydrochloride and 4-dimethylaminopyridine. The reacting mixture was stirred at room temperature for 12 h. After filtration, the resulting solution of intermediate 6 was collected and used for the next step.

To Vitamin B in DMF was added Succinic anhydride and pyridine. The reacting mixture was stirred at 80° C. for 24 h. After adding CH₂Cl₂, yellow particles were formed and collected through centrifuge. The yellow solid intermediate 7 was used for the next step.

To a solution of intermediate 7 in DMF was added intermediate 1 in THF, trimethylamine, NHS and DCC. The resulting mixture was stirred at room temperature for 12 h. After adding CH₂Cl₂, the organic phase was washed with water for three times and then dried over solid MgSO₄. The solution was then filtered, evaporated and dried under high vacuum. The product was purified by silica column chromatography in order to afford intermediate 8.

Intermediate 8 was stirred in excess amount of trifluoroacetic acid for 2 h at room temperature. The reacting mixture was evaporated under reduced pressure to yield intermediate 9 and was used for the next step without further purification.

Intermediate 9 was dissolved in the solution of intermediate 6, followed by adding trimethylamine. The resulting mixture was stirred at room temperature for 12 h. After adding CH₂Cl₂, the organic phase was washed with water for three times and then dried over solid MgSO₄. The solution was then filtered, evaporated and dried under high vacuum. The product was purified by silica column chromatography in order to afford VL-3.

Scheme 13: (A) General synthetic routes of folate-lipids using aldehyde containing chains; (B) One example, synthesis of VL-4.

A

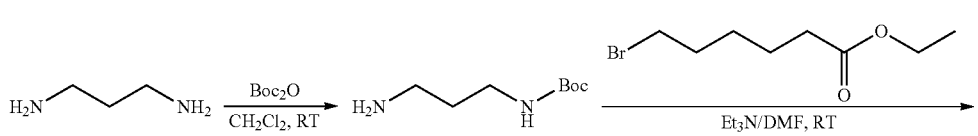

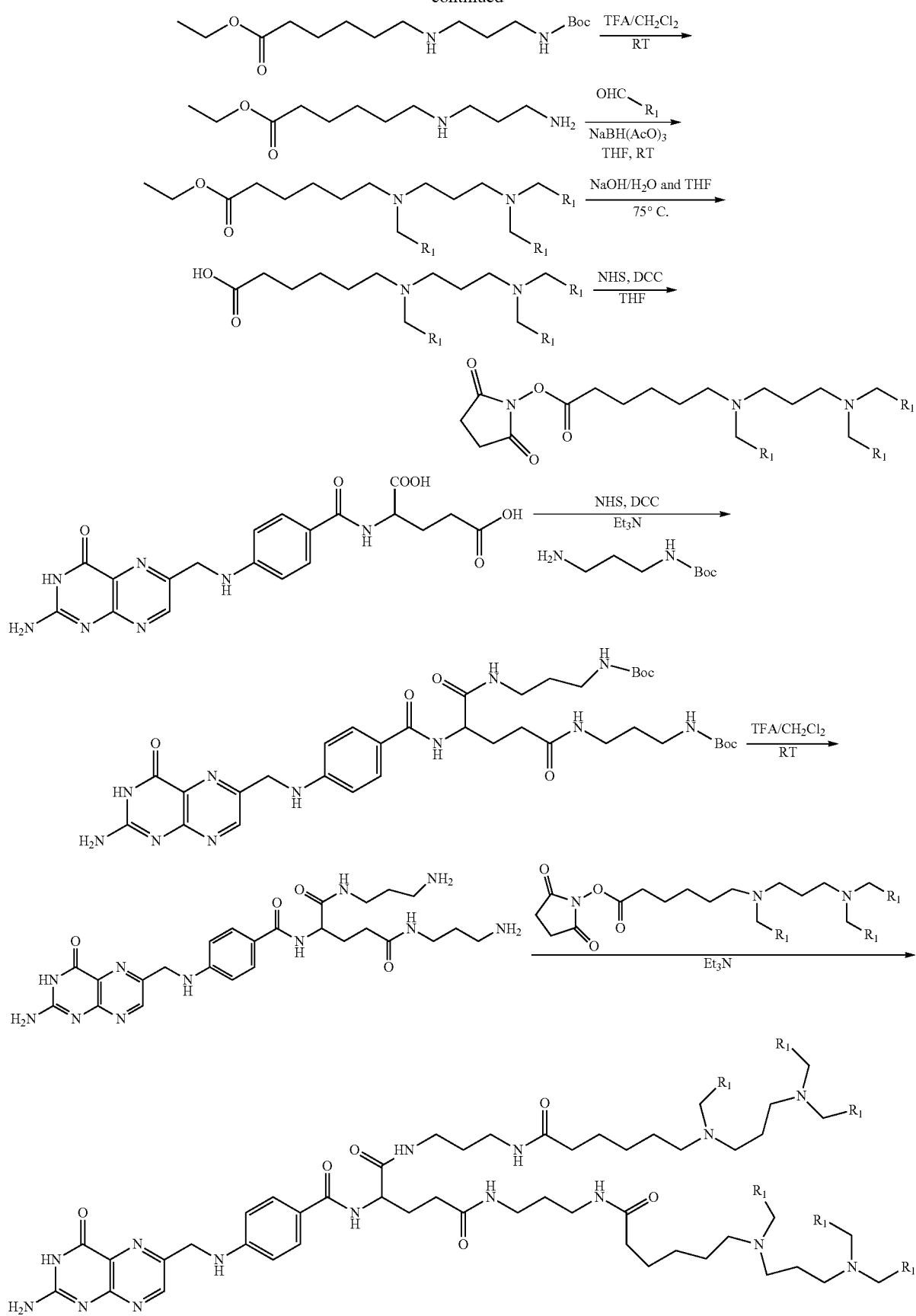

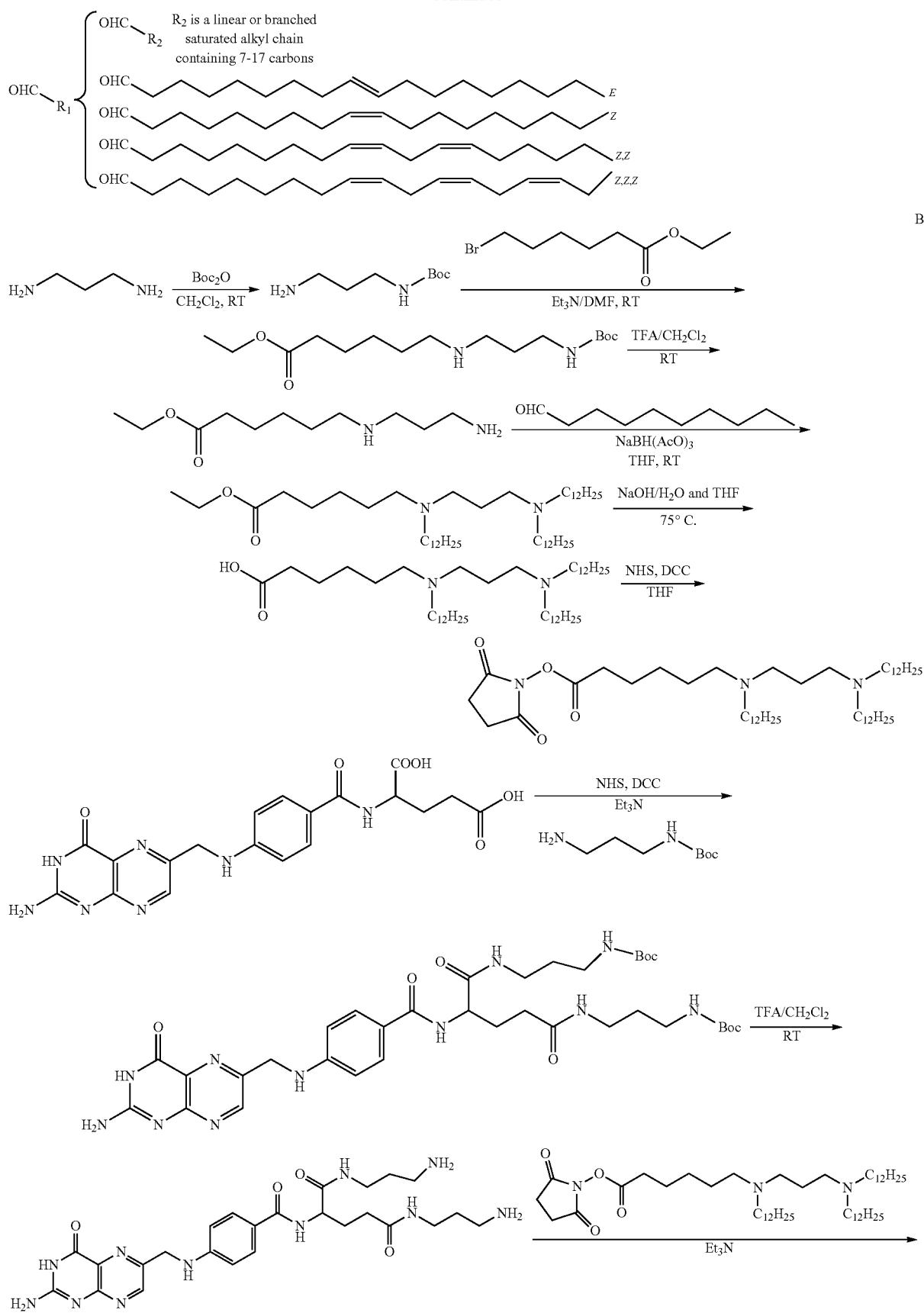

115

-continued

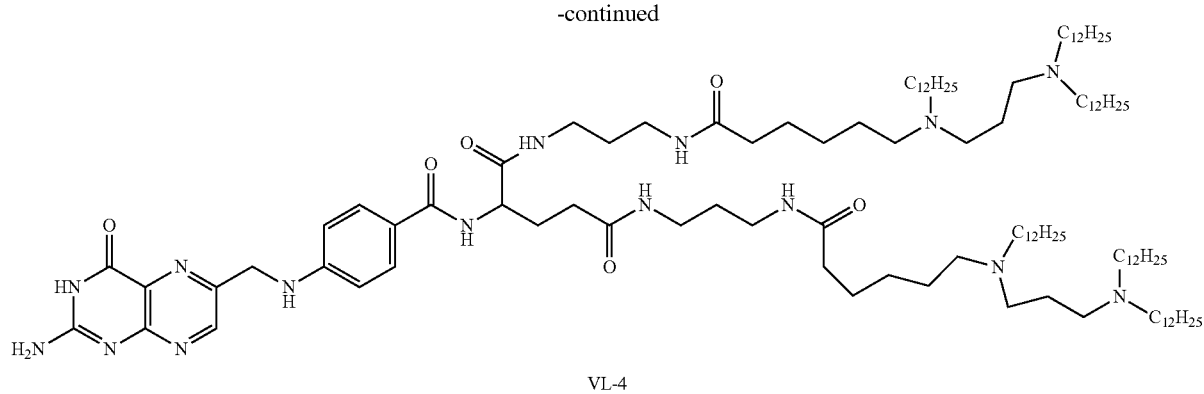

VL-4

Synthetic Route of VL-4:

To a solution of diamine in CHCl$_3$ was slowly added a solution of Boc$_2$O in CHCl$_3$ via an additional funnel over 2.5 h. The resulting suspension was stirred and NaHCO$_3$ (1N) was slowly added. The organic layer was washed with 1N NaHCO$_3$ and brine, and then dried over solid MgSO$_4$. The solution was then filtered, evaporated and dried under high vacuum in order to afford intermediate 1.

Intermediate 1 was stirred in DMF with 6-Bromohexanoic acid ethyl ester and trimethylamine for 48 h. After adding CH$_2$Cl$_2$ the organic phase was washed with water for three times and then dried over solid MgSO$_4$. The solution was then filtered, evaporated and dried under high vacuum. The product was purified by silica column chromatography in order to afford intermediate 2.

Intermediate 2 was stirred in excess amount of trifluoroacetic acid for 2 h at room temperature. The reacting mixture was evaporated under reduced pressure to yield intermediate 3 that was used for the next step without further purification.

To a solution of intermediate 3 in THF was added trimethylamine, decanal and sodium triacetoxyborohydride. The reacting mixture was stirred at room temperature for 24 h and was evaporated under reduced pressure. The resulting product was purified through silica column chromatography to afford intermediate 4.

To a solution of intermediate 4 in THF was added methanol and 1 M NaOH aqueous. The resulting mixture was stirred at 70° C. for 5 h and was evaporated under reduced pressure. The resulting mixture was purified through silica column chromatography to afford intermediate 5.

To intermediate 5 in CH$_2$Cl$_2$ was added N-Hydroxysuccinimide, 1-(3-Dimethylaminopropyl)-3-ethylcarbodiimide hydrochloride and 4-dimethylaminopyridine. The reacting mixture was stirred at room temperature for 12 h. After filtration, the resulting solution of intermediate 6 was collected and used for the next step.

To folic acid in DMF was added intermediate 1 in THF, trimethylamine, NHS and DCC. The resulting mixture was stirred at room temperature for 12 h. After adding CH$_2$Cl$_2$, the organic phase was washed with water for three times and then dried over solid MgSO$_4$. The solution was then filtered, evaporated and dried under high vacuum. The product was purified by silica column chromatography in order to afford intermediate 7.

Intermediate 7 was stirred in excess amount of trifluoroacetic acid for 2 h at room temperature. The reacting mixture was evaporated under reduced pressure to yield intermediate 8 and was used for the next step without further purification.

Intermediate 8 was dissolved in the solution of intermediate 6, followed by adding trimethylamine. The resulting mixture was stirred at room temperature for 12 h. After adding CH$_2$Cl$_2$, the organic phase was washed with water for three times and then dried over solid MgSO$_4$. The solution was then filtered, evaporated and dried under high vacuum. The product was purified by silica column chromatography in order to afford VL-4.

Scheme 14: (A) General synthetic routes of Vitamin C-lipids using aldehyde containing chains; (B) One example, synthesis of VL-5.

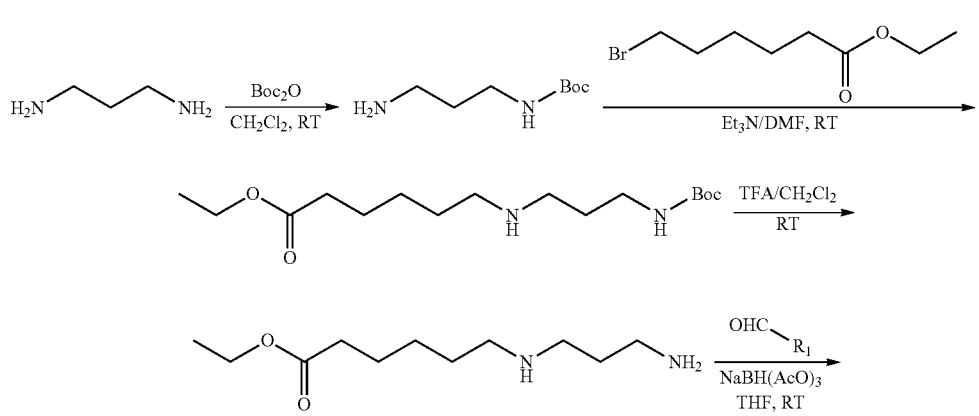

A

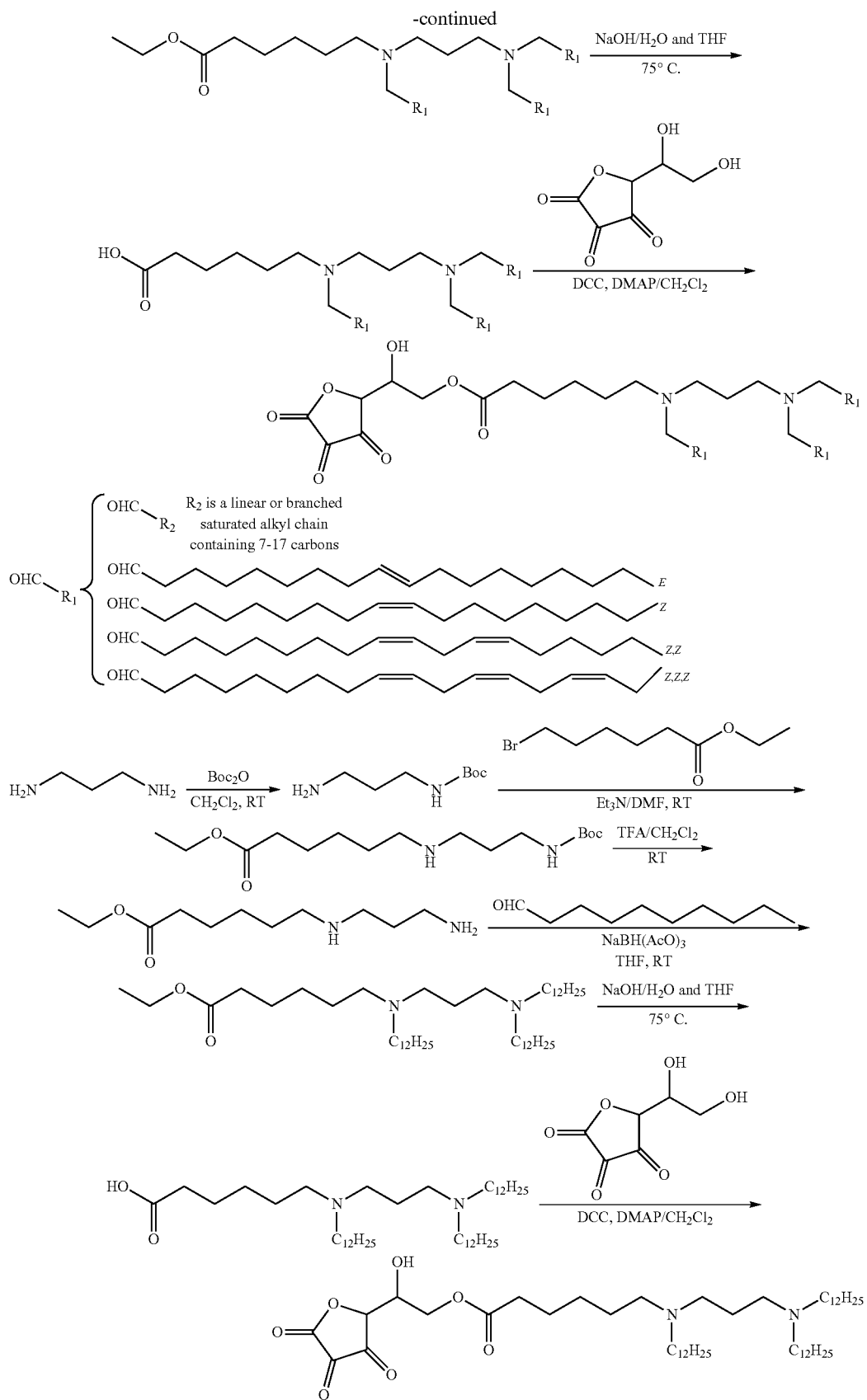

Synthetic Route of VL-5:

To a solution of diamine in CHCl₃ was slowly added a solution of Boc₂O in CHCl₃ via an additional funnel over 2.5 h. The resulting suspension was stirred and NaHCO₃ (1N) was slowly added. The organic layer was washed with 1N NaHCO₃ and brine, and then dried over solid MgSO₄. The solution was then filtered, evaporated and dried under high vacuum in order to afford intermediate 1.

Intermediate 1 was stirred in DMF with 6-Bromohexanoic acid ethyl ester and trimethylamine for 48 h. After adding CH₂Cl₂ the organic phase was washed with water for three times and then dried over solid MgSO₄. The solution was then filtered, evaporated and dried under high vacuum. The product was purified by silica column chromatography in order to afford intermediate 2.

Intermediate 2 was stirred in excess amount of trifluoroacetic acid for 2 h at room temperature. The reacting mixture was evaporated under reduced pressure to yield intermediate 3 that was used for the next step without further purification.

To a solution of intermediate 3 in THF was added trimethylamine, decanal and sodium triacetoxyborohydride. The reacting mixture was stirred at room temperature for 24 h and was evaporated under reduced pressure. The resulting product was purified through silica column chromatography to afford intermediate 4.

To a solution of intermediate 4 in THF was added methanol and 1 M NaOH aqueous. The resulting mixture was stirred at 70° C. for 5 h and was evaporated under reduced pressure. The resulting mixture was purified through silica column chromatography to afford intermediate 5.

Vitamin C derivative and intermediate 5 were stirred in CH₂Cl₂ followed by adding DCC and DMAP. The reacting mixture was stirred at room temperature for 12 h. After adding CH₂Cl₂, the organic phase was washed with water for three times and then dried over solid MgSO₄. The solution was then filtered, evaporated and dried under high vacuum. The product was purified by silica column chromatography in order to afford VL-5.

Scheme 15: (A) General synthetic routes of Vitamin C-lipids using aldehyde containing chains; (B) One example, synthesis of VL-6.

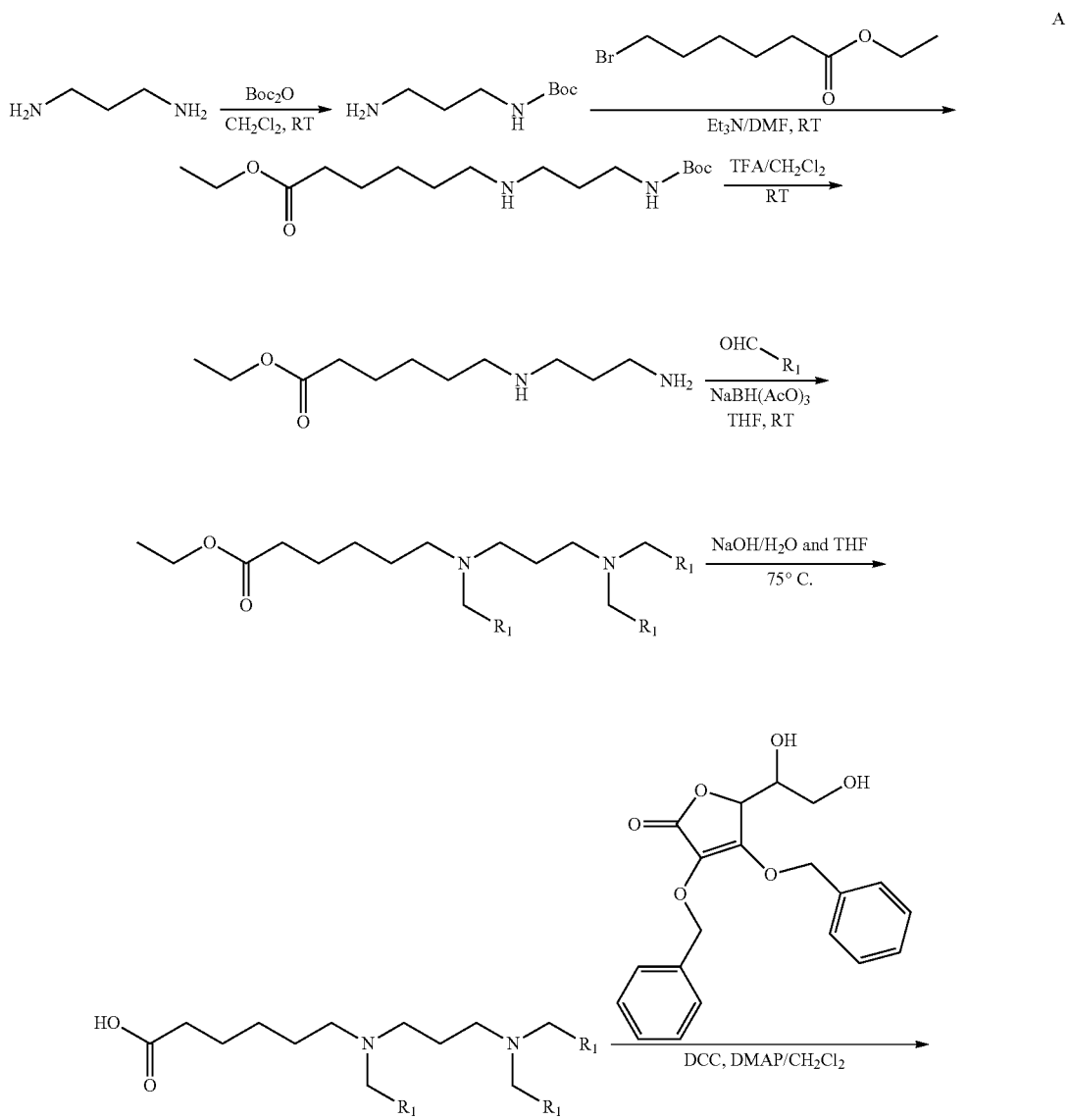

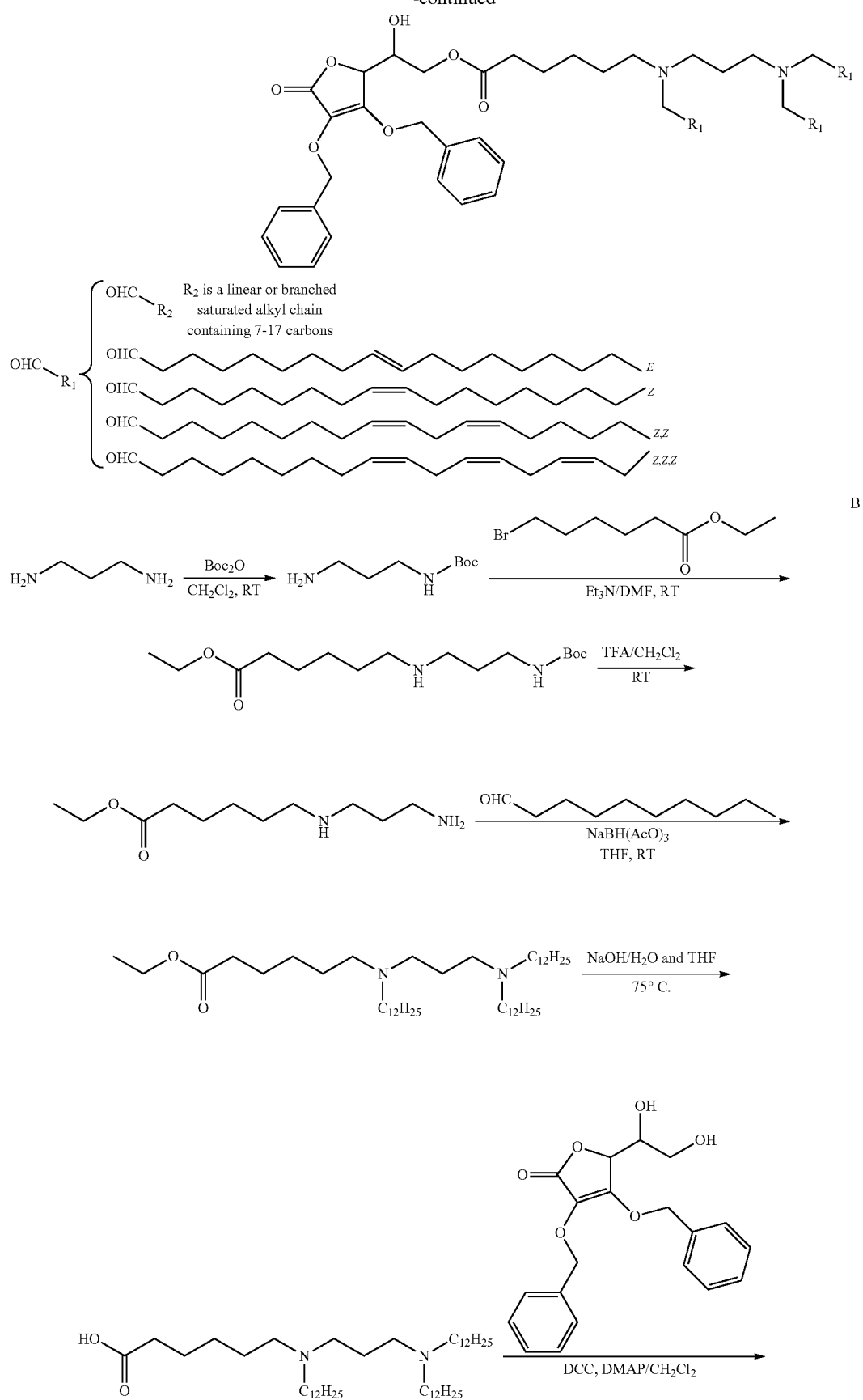

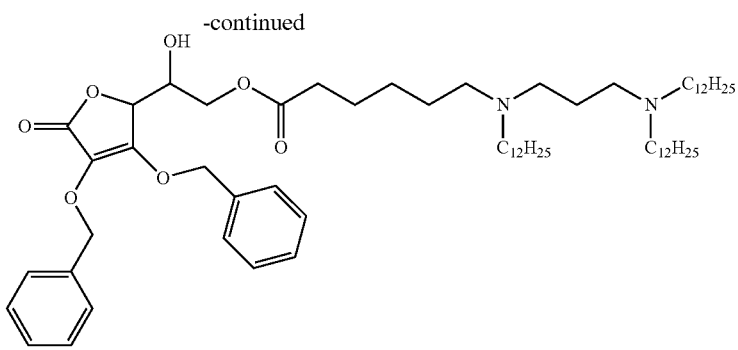

VL-6

Synthetic Route of VL-6:

To a solution of diamine in CHCl$_3$ was slowly added a solution of Boc$_2$O in CHCl$_3$ via an additional funnel over 2.5 h. The resulting suspension was stirred and NaHCO$_3$ (1N) was slowly added. The organic layer was washed with 1N NaHCO$_3$ and brine, and then dried over solid MgSO$_4$. The solution was then filtered, evaporated and dried under high vacuum in order to afford intermediate 1.

Intermediate 1 was stirred in DMF with 6-Bromohexanoic acid ethyl ester and trimethylamine for 48 h. After adding CH$_2$Cl$_2$ the organic phase was washed with water for three times and then dried over solid MgSO$_4$. The solution was then filtered, evaporated and dried under high vacuum. The product was purified by silica column chromatography in order to afford intermediate 2.

Intermediate 2 was stirred in excess amount of trifluoroacetic acid for 2 h at room temperature. The reacting mixture was evaporated under reduced pressure to yield intermediate 3 that was used for the next step without further purification.

To a solution of intermediate 3 in THF was added trimethylamine, decanal and sodium triacetoxyborohydride. The reacting mixture was stirred at room temperature for 24 h and was evaporated under reduced pressure. The resulting product was purified through silica column chromatography to afford intermediate 4.

To a solution of intermediate 4 in THF was added methanol and 1 M NaOH aqueous. The resulting mixture was stirred at 70° C. for 5 h and was evaporated under reduced pressure. The resulting mixture was purified through silica column chromatography to afford intermediate 5.

Vitamin C derivative and intermediate 5 were stirred in CH$_2$Cl$_2$ followed by adding DCC and DMAP. The reacting mixture was stirred at room temperature for 12 h. After adding CH$_2$Cl$_2$, the organic phase was washed with water for three times and then dried over solid MgSO$_4$. The solution was then filtered, evaporated and dried under high vacuum. The product was purified by silica column chromatography in order to afford VL-6.

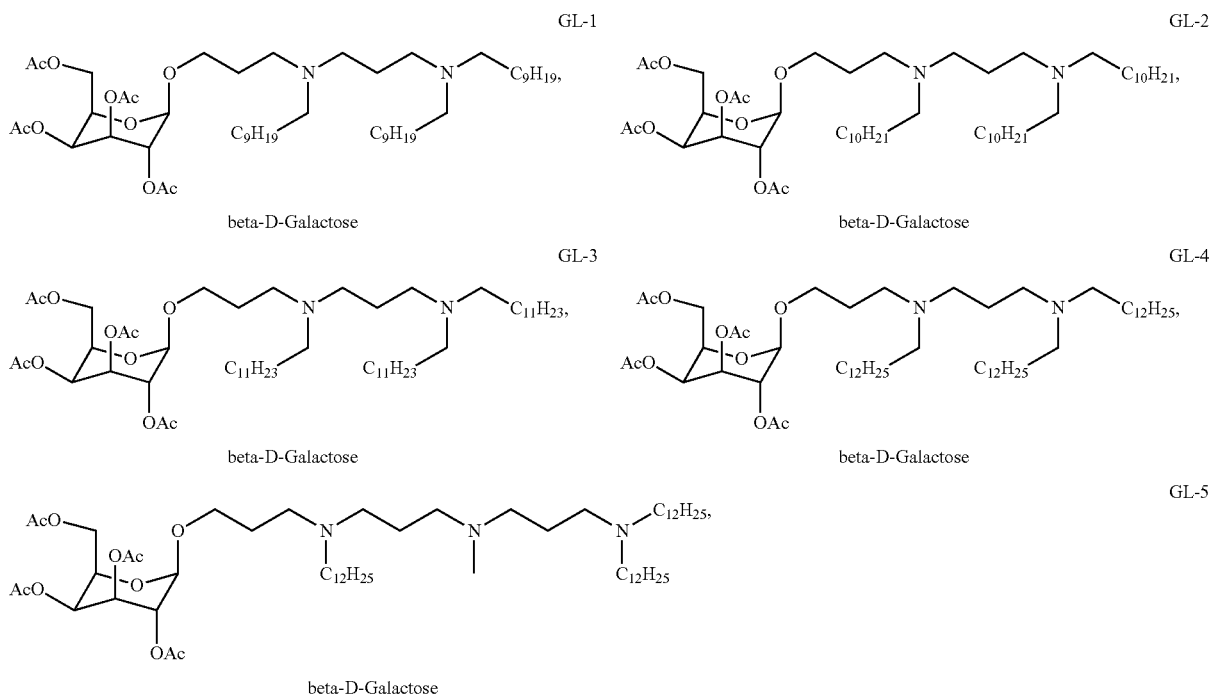

Scheme 16: Structures of synthesized glycolipids GL 1-18.

-continued
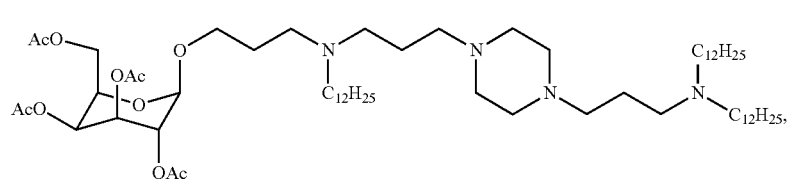
GL-6
beta-D-Galactose
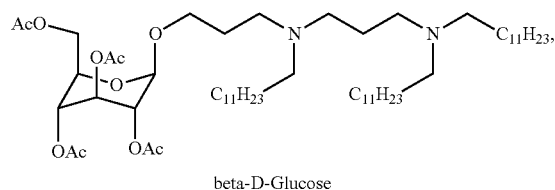
GL-7
beta-D-Glucose
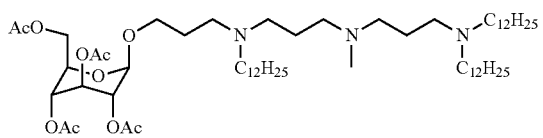
GL-8
beta-D-Glucose
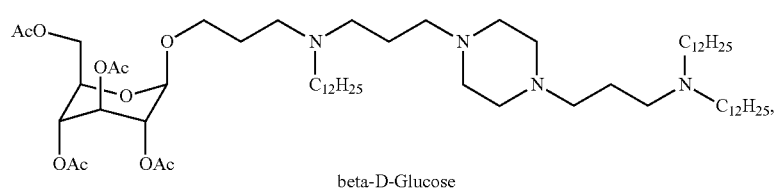
GL-9
beta-D-Glucose
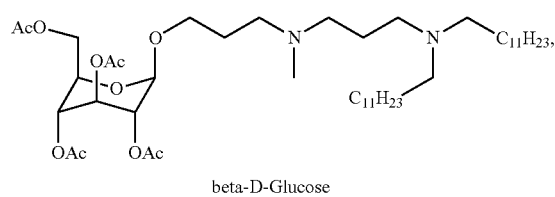
GL-14
beta-D-Glucose
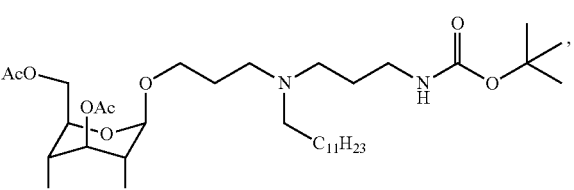
GL-15
beta-D-Glucose
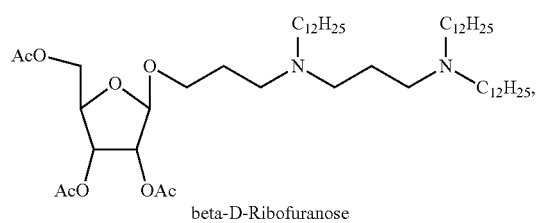
GL-16
beta-D-Ribofuranose
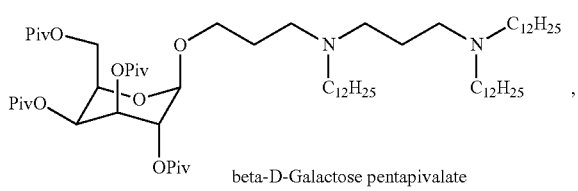
GL-18
beta-D-Galactose pentapivalate
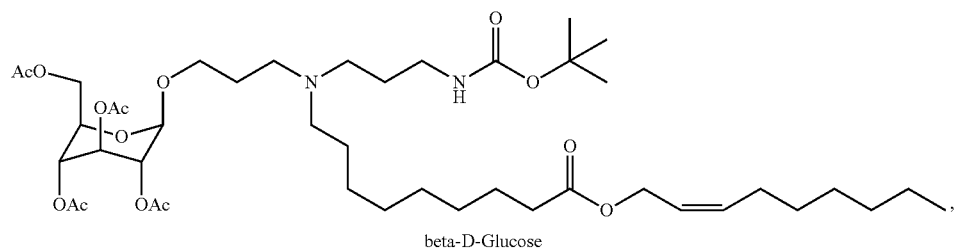
GL-11
beta-D-Glucose -continued
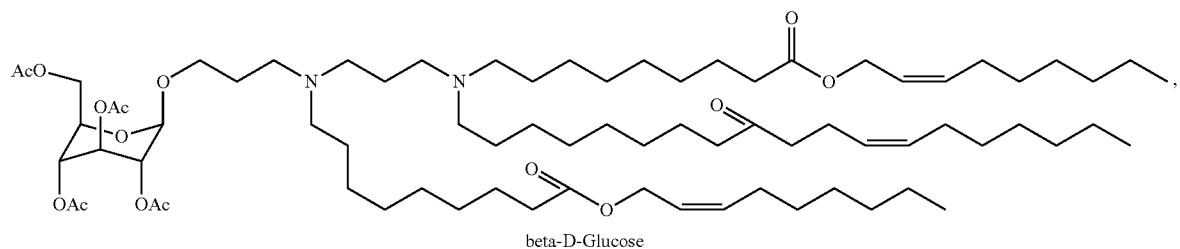
GL-10
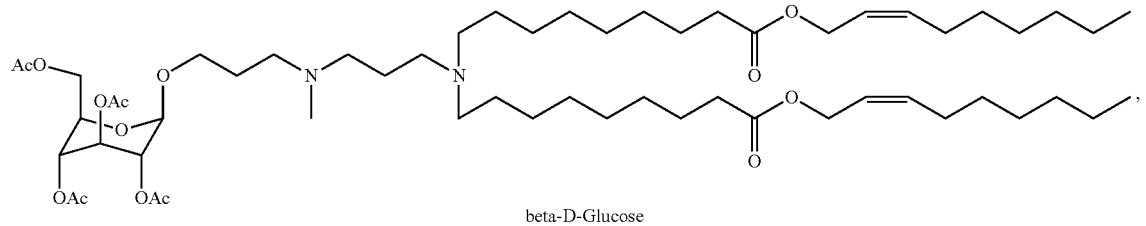
GL-2
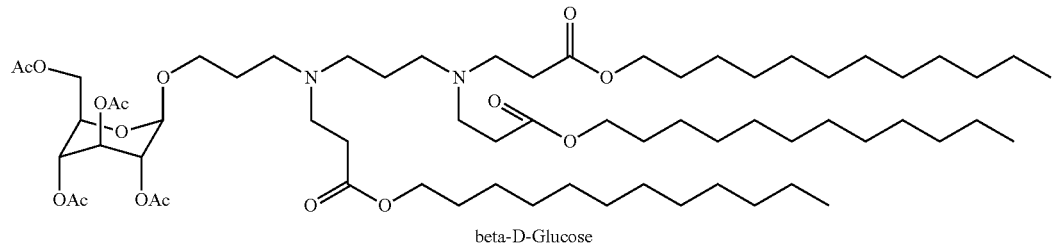
GL-13
Scheme 17: Structures of a synthesized phospholipids PL 1-16.
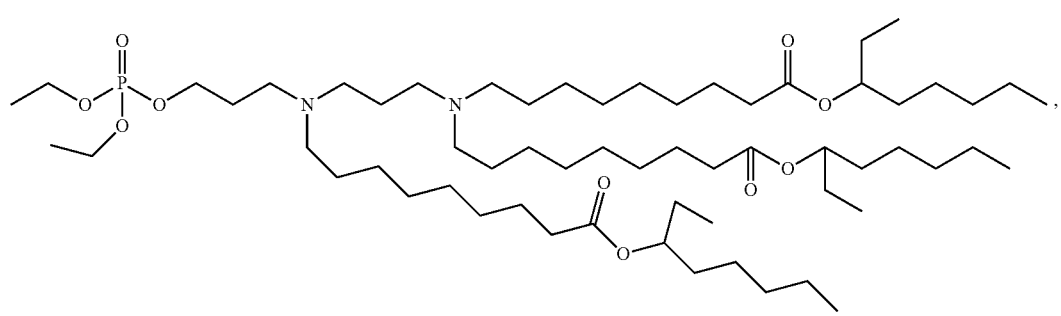
PL-1
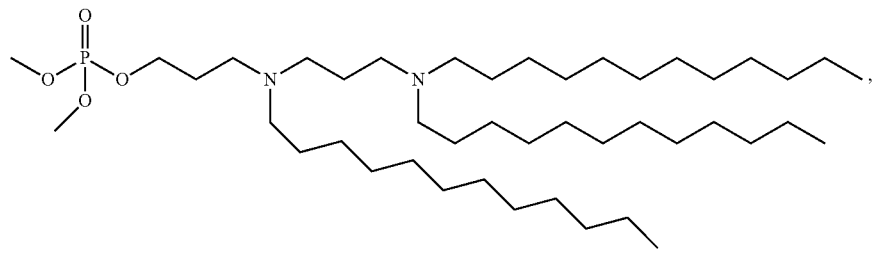
PL-2

-continued
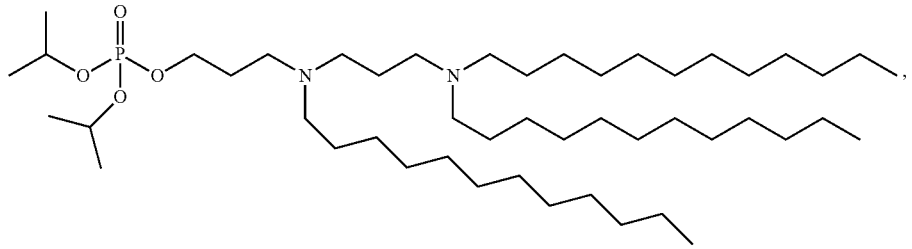
PL-3
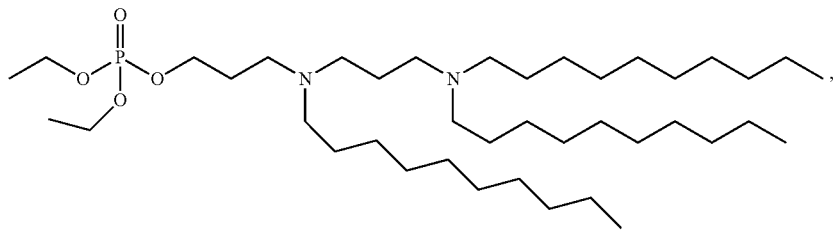
PL-4
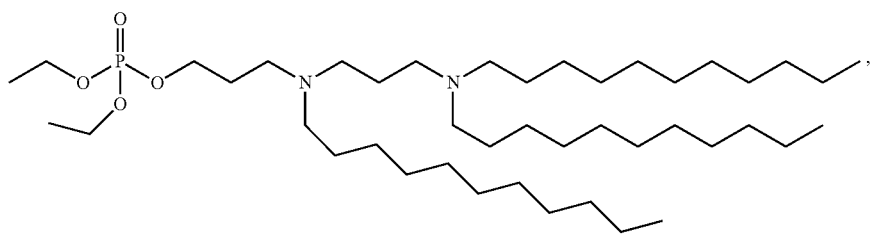
PL-5
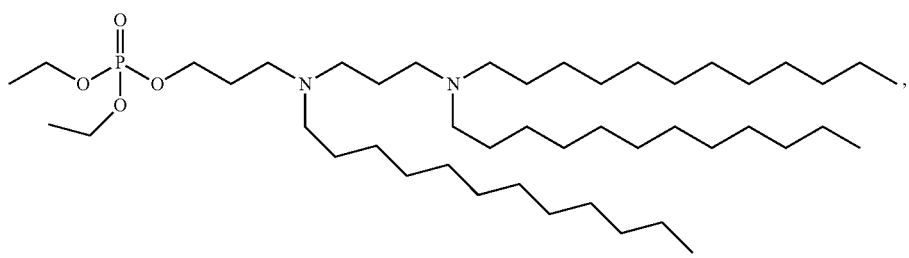
PL-6
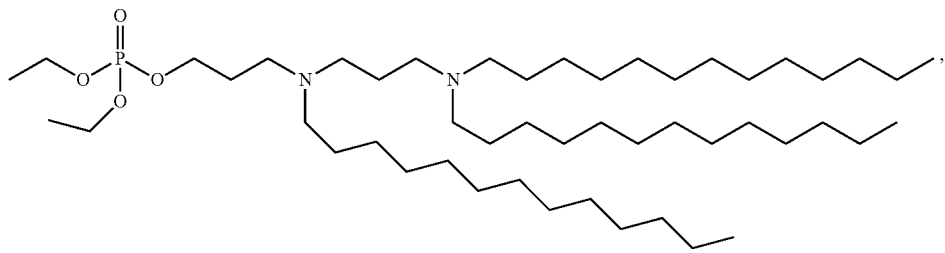
PL-7
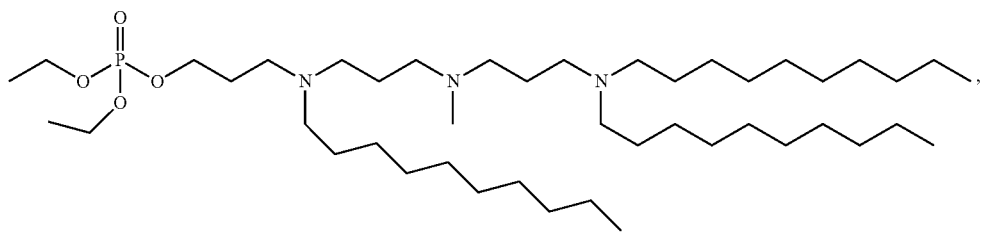
PL-8

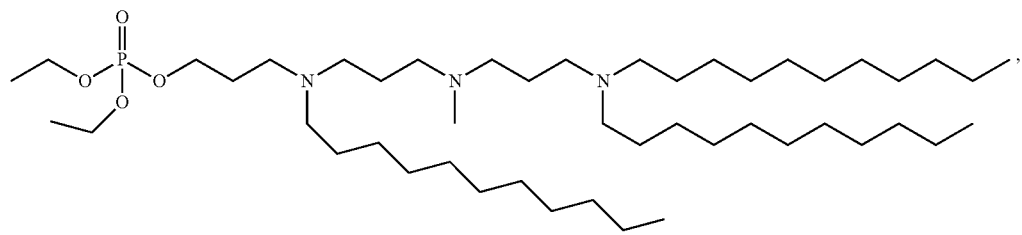
PL-9
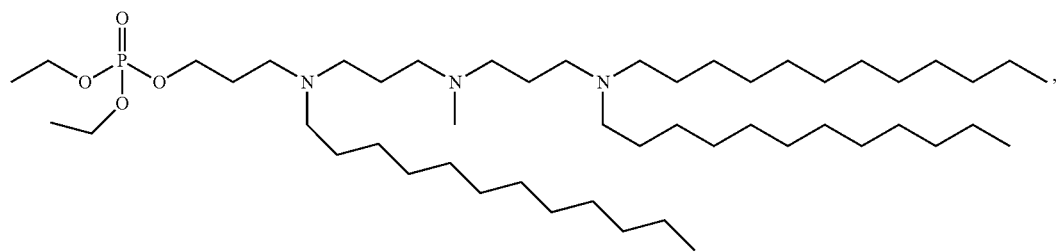
PL-10
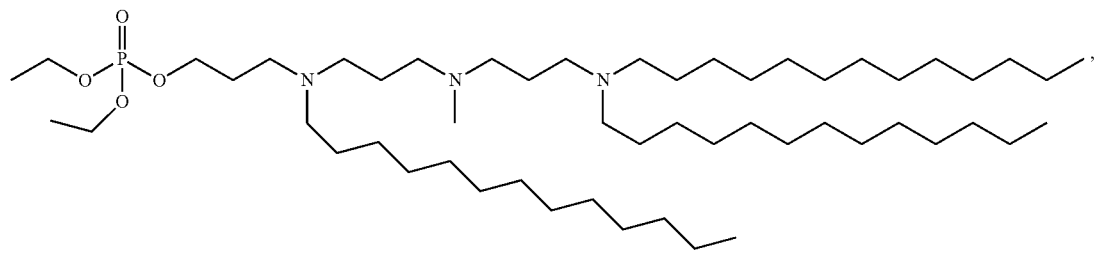
PL-11
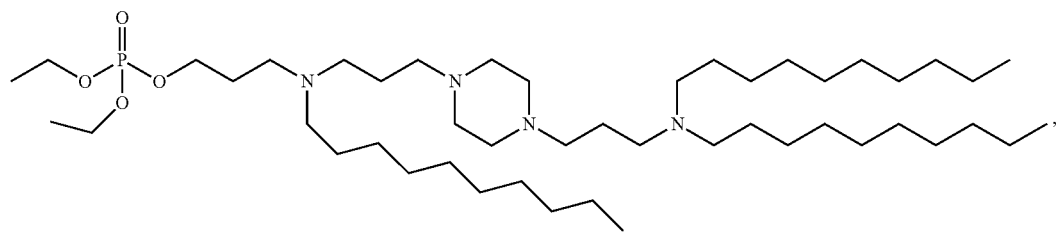
PL-12
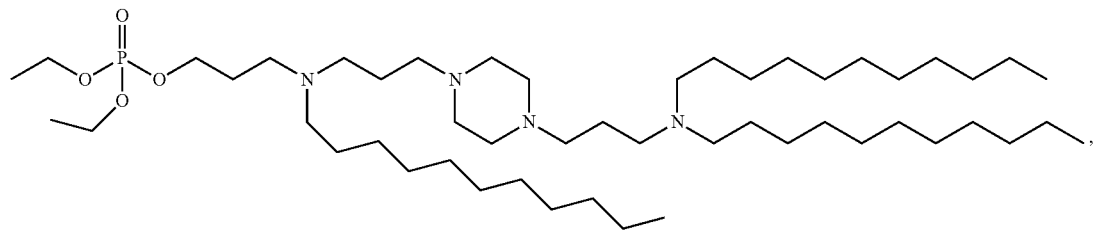
PL-13
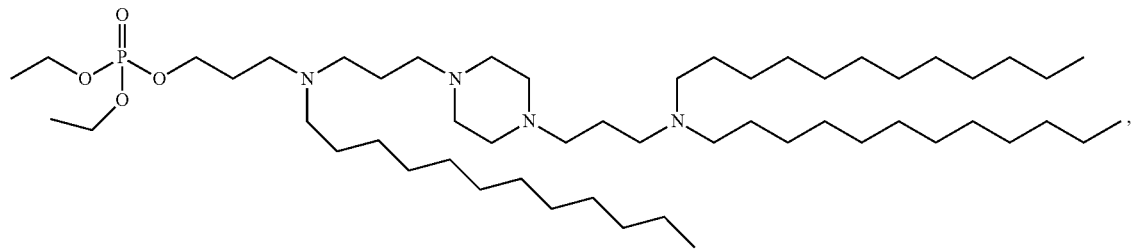
PL-14

PL-15
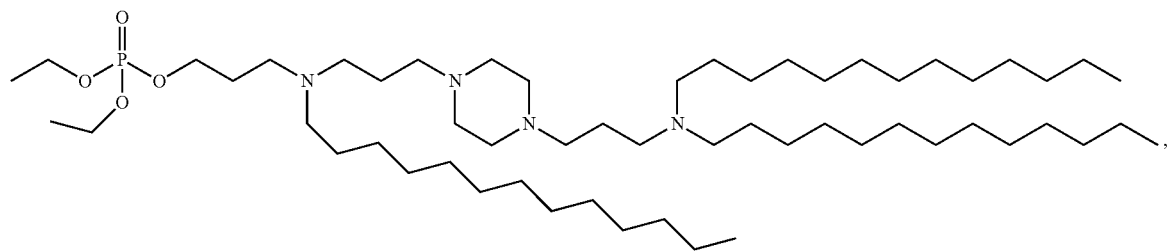
PL-16
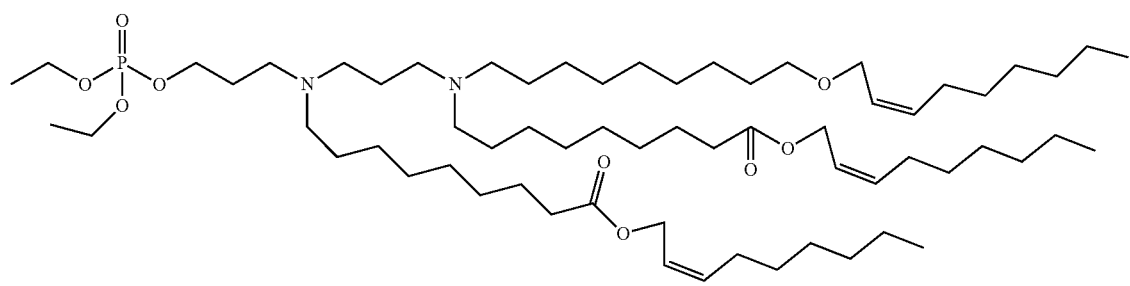
Scheme 18: Structures of synthesized Vitamin-lipids VL 1-6.
VL-1
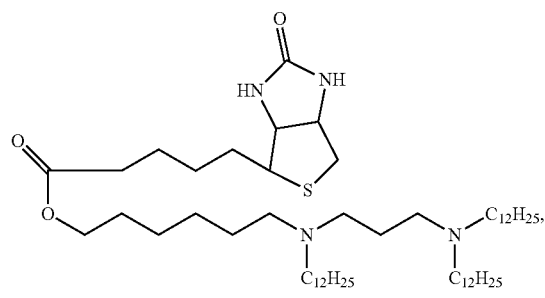
VL-2
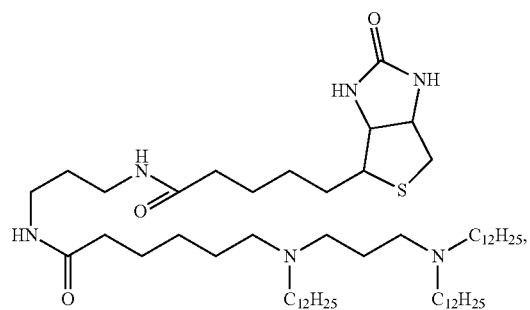
VL-3
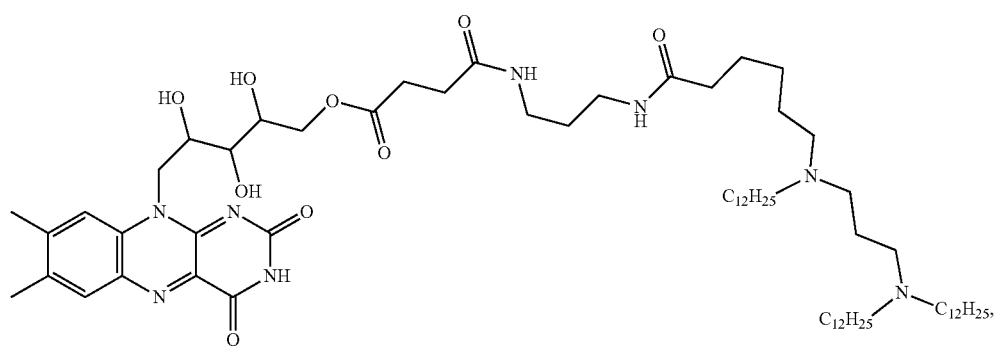

-continued

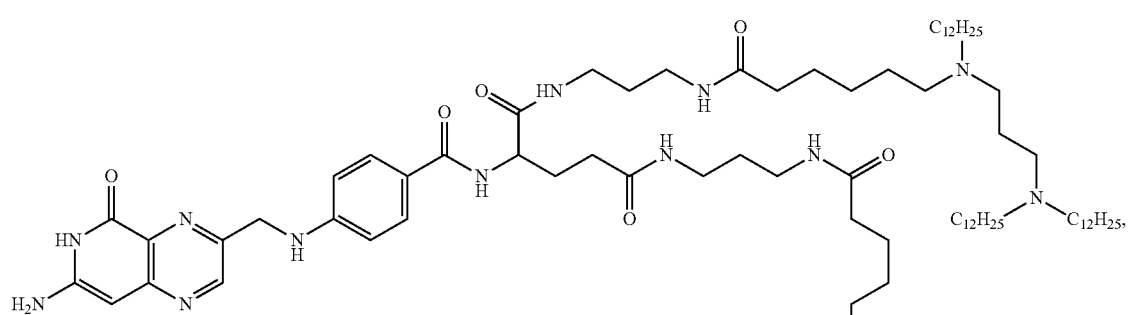
VL-4

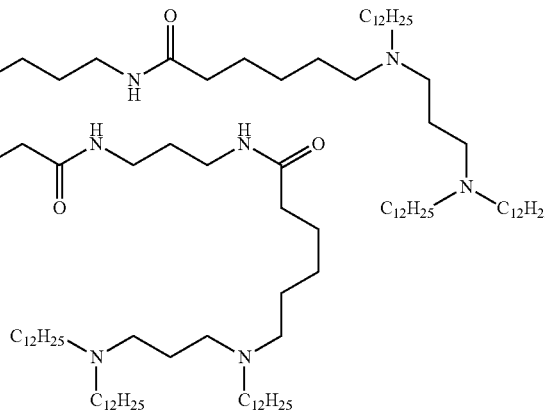

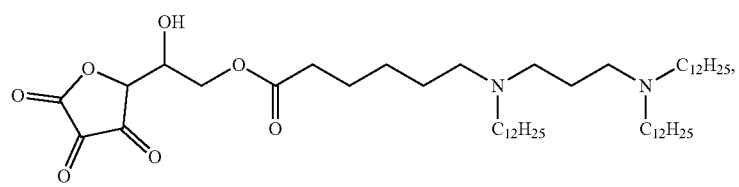
VL-5

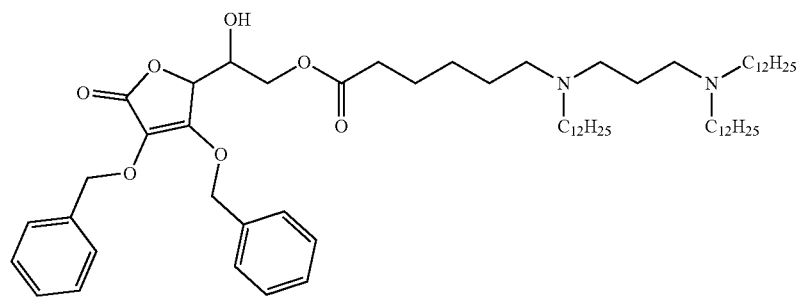
VL-6

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:
1. A compound selected from:

GL-1
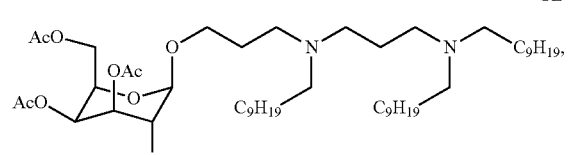
beta-D-Galactose

-continued

GL-2
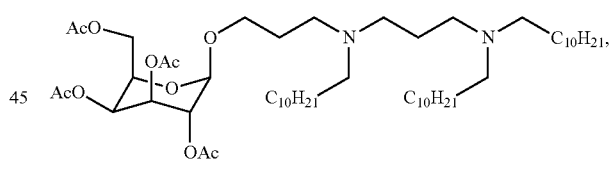
beta-D-Galactose

GL-3
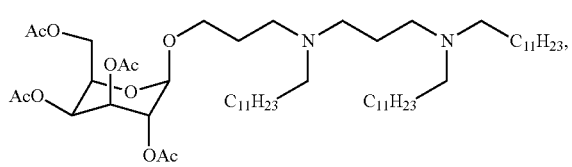
beta-D-Galactose

GL-4
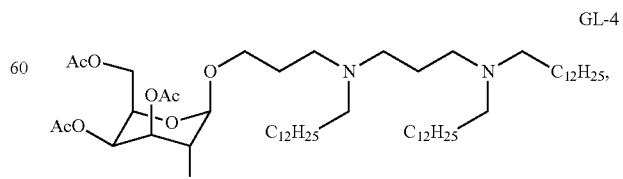
beta-D-Galactose

137
-continued
GL-5
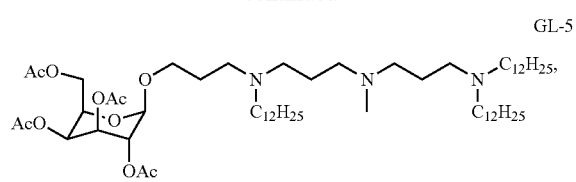
beta-D-Galactose
GL-6
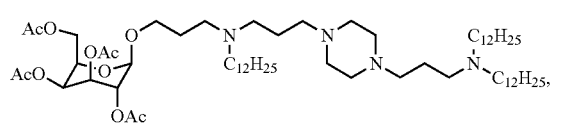
beta-D-Galactose
GL-7
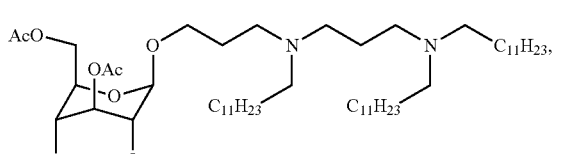
beta-D-Glucose
GL-8
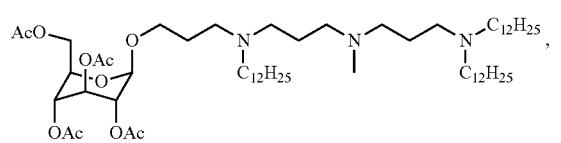
beta-D-Glucose
GL-9
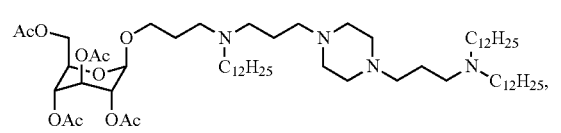
beta-D-Glucose
GL-10
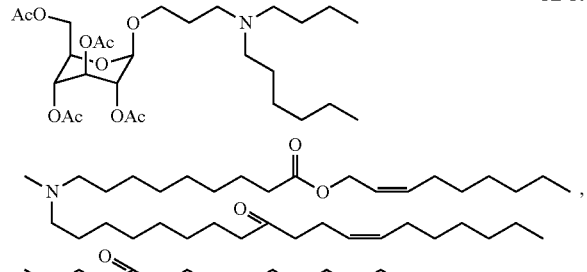
GL-13
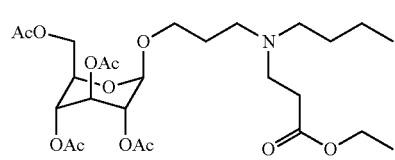
138
-continued
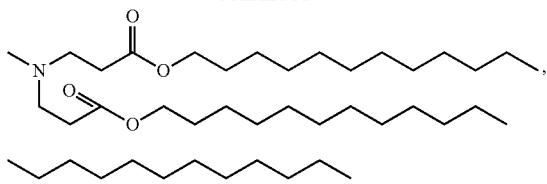
beta-D-Glucose
GL-16
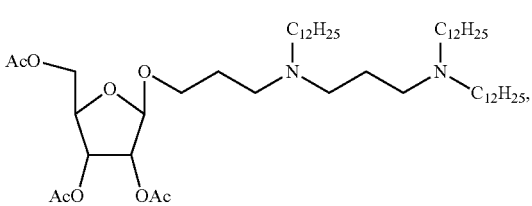
beta-D-Ribofuranose
GL-17
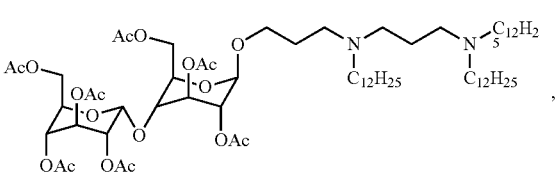
beta-D-Maltose
GL-18
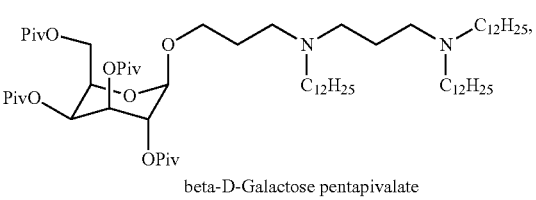
beta-D-Galactose pentapivalate
GL-19
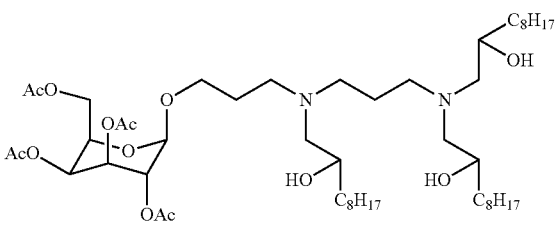
G-20
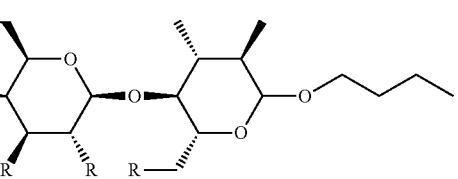

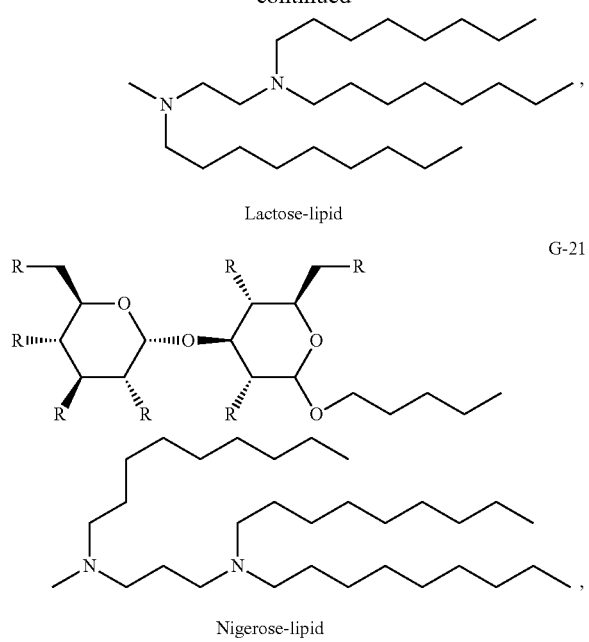
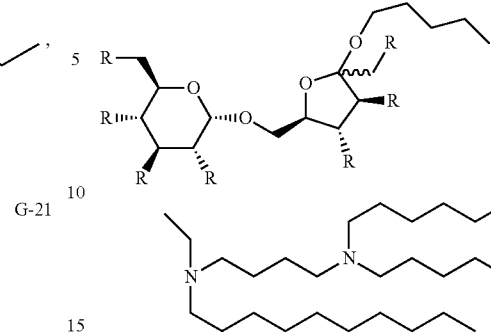
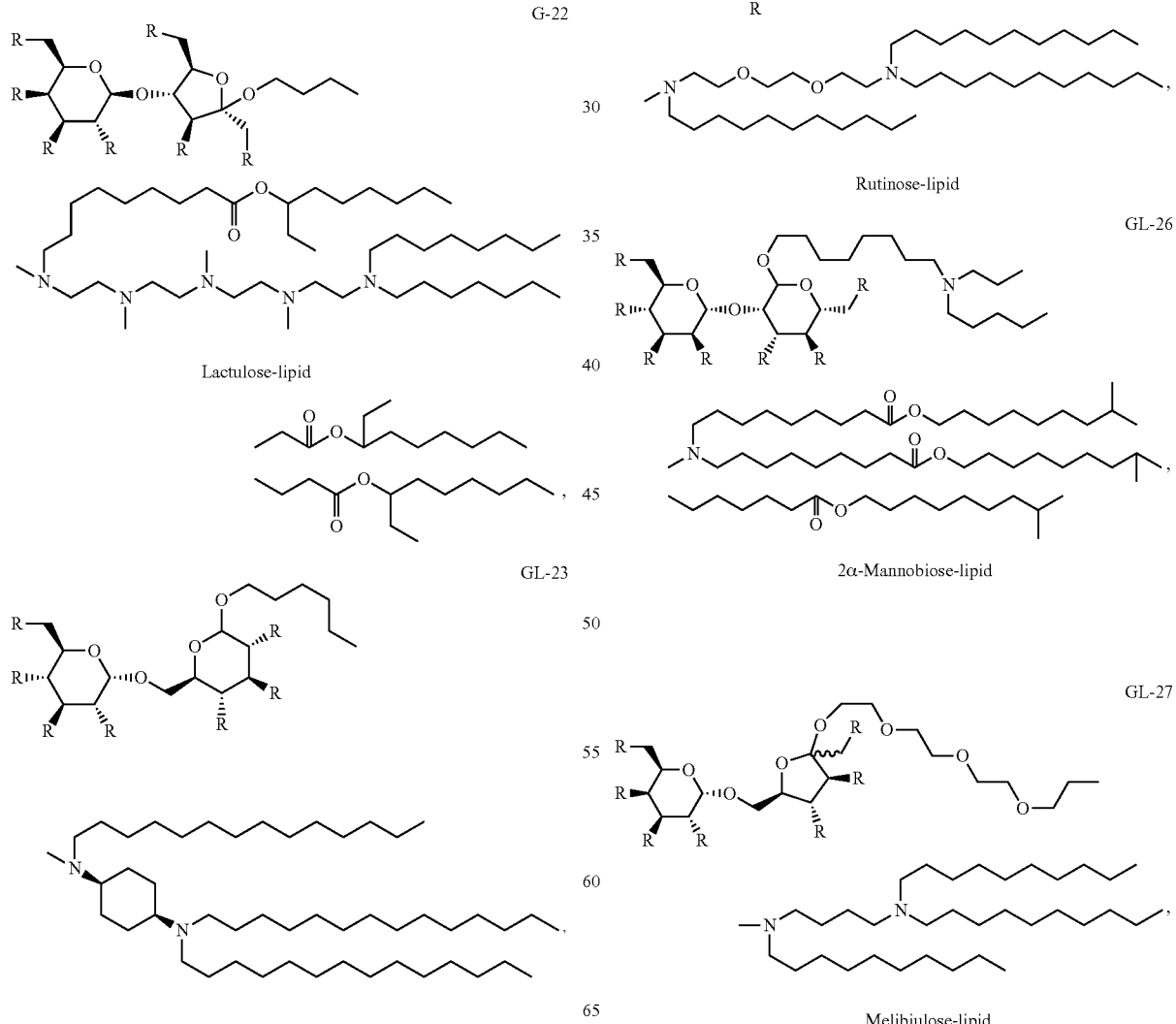

141
-continued
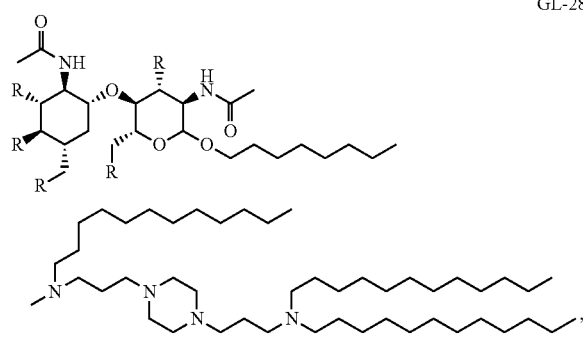
Chitobiose-lipid
GL-28
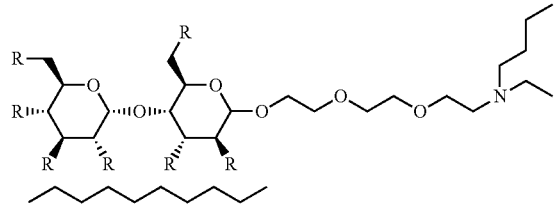
Maltose-lipid
GL-29
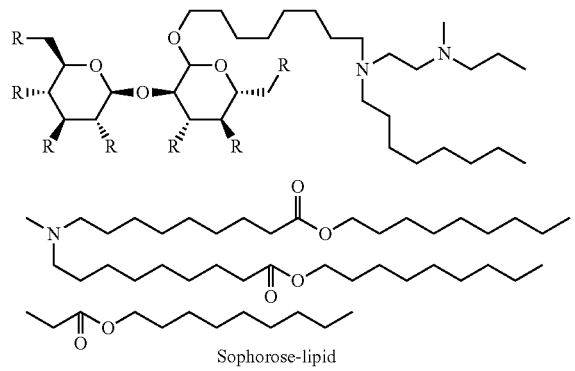
Sophorose-lipid
GL-30
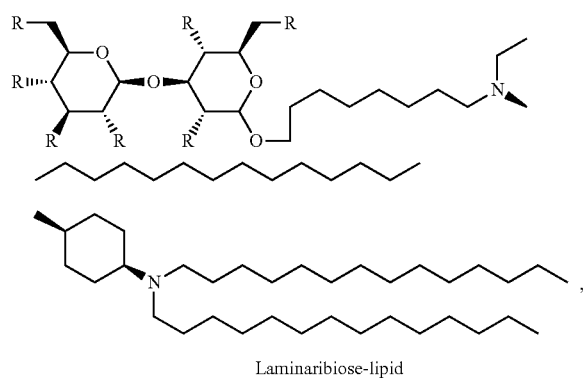
Laminaribiose-lipid
GL-31
142
-continued
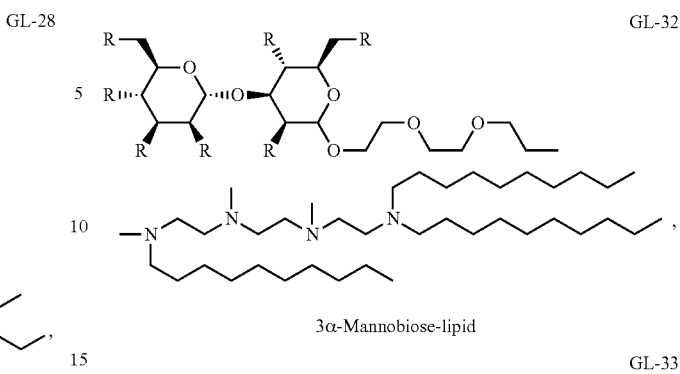
3α-Mannobiose-lipid
GL-32
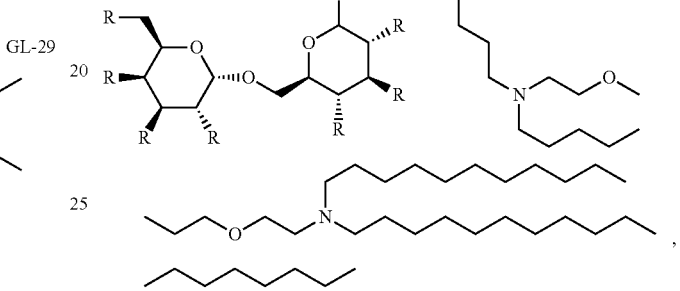
Melibiose-lipid
GL-33
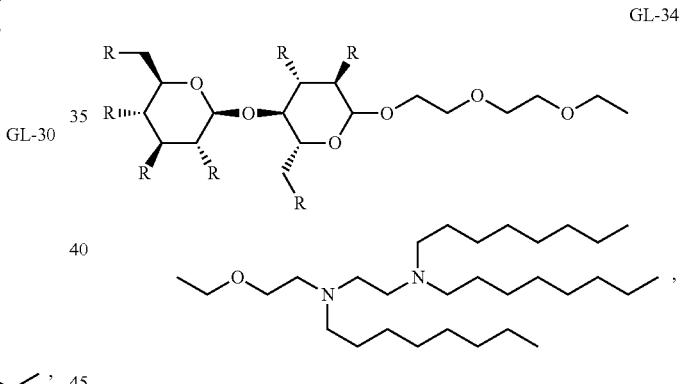
Cellobiose-lipid
GL-34
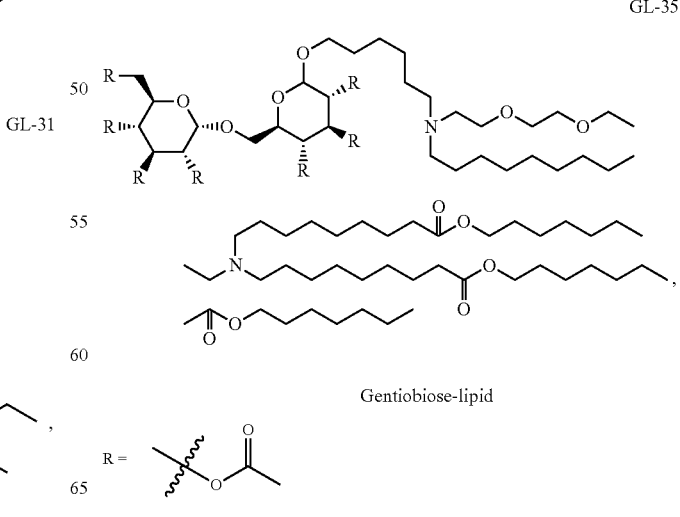
Gentiobiose-lipid
GL-35

PL-1
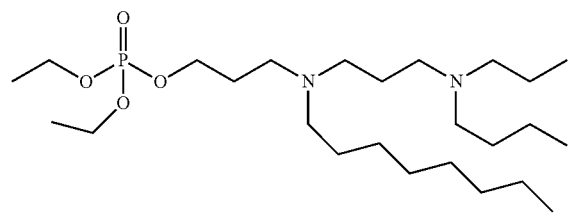
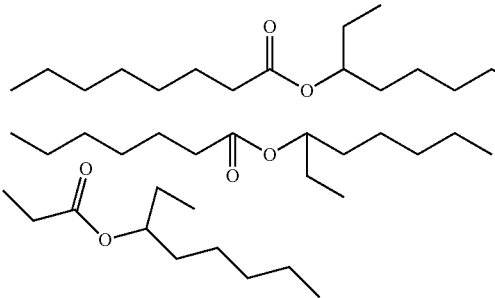
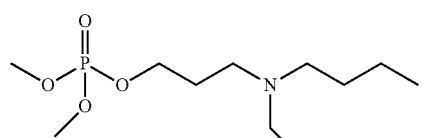
PL-2
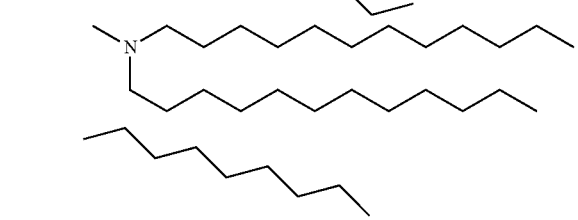
PL-3
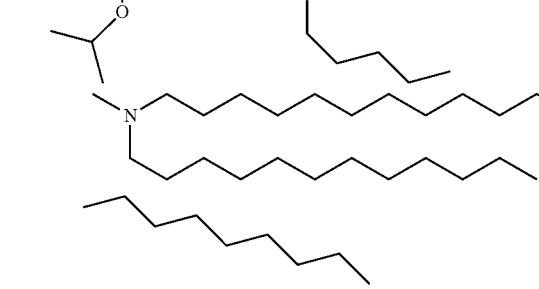
PL-4
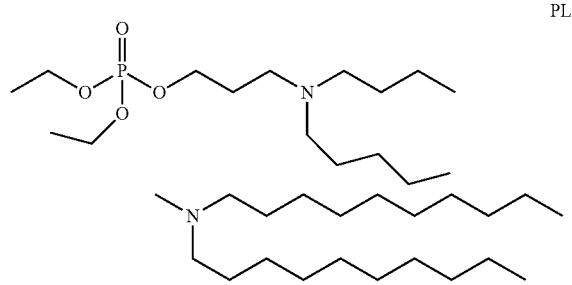
PL-5
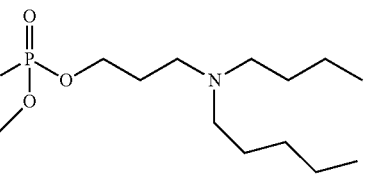
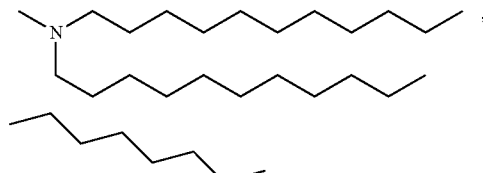
PL-6
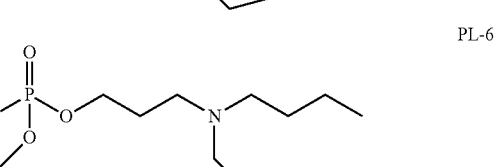
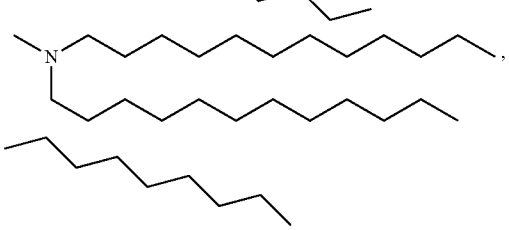
PL-7
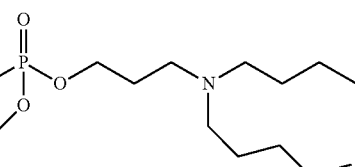
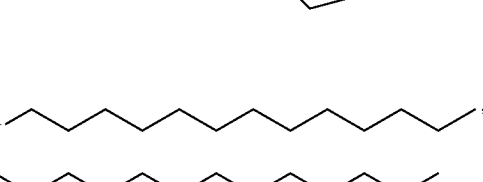
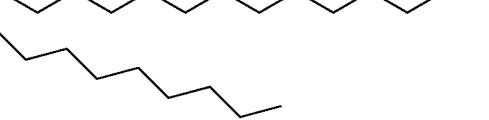
PL-8
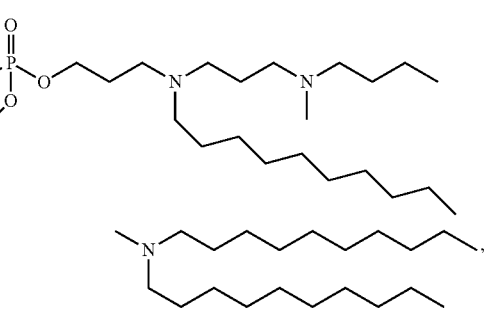

PL-9
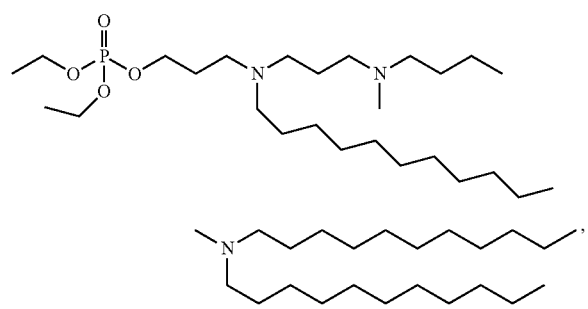
PL-10
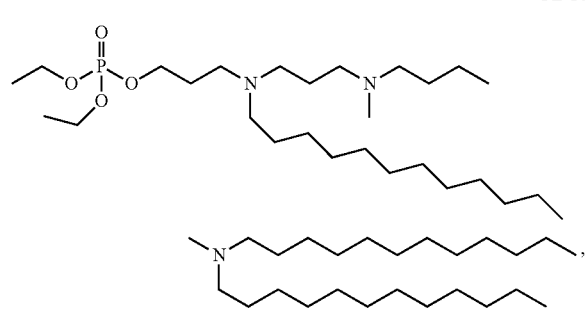
PL-11
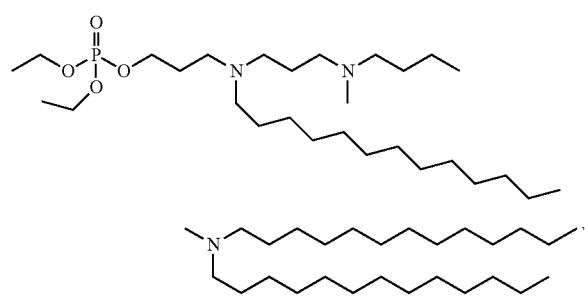
PL-12
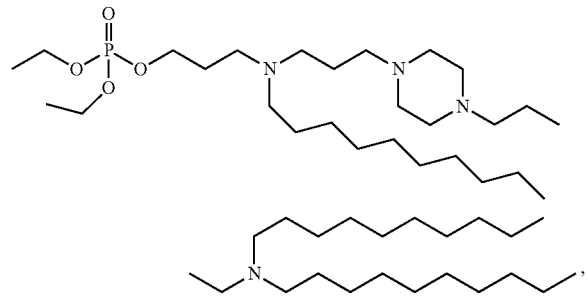
PL-13
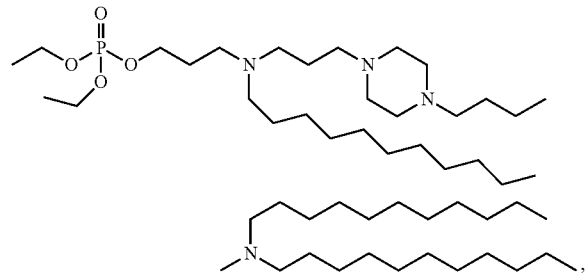
PL-14
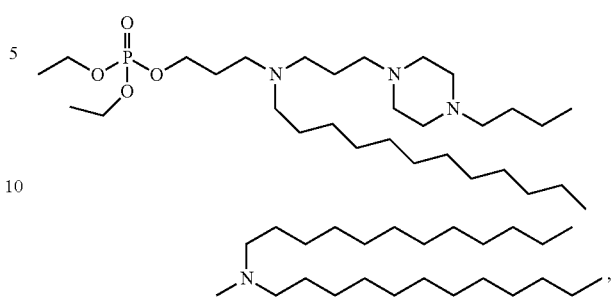
PL-15
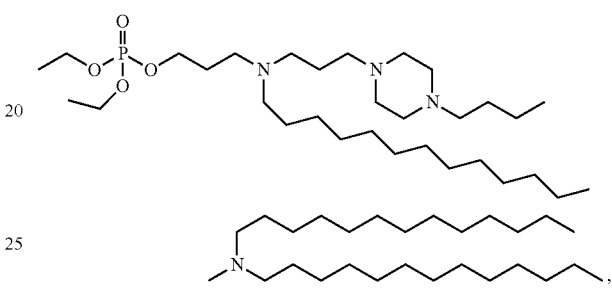
PL-16
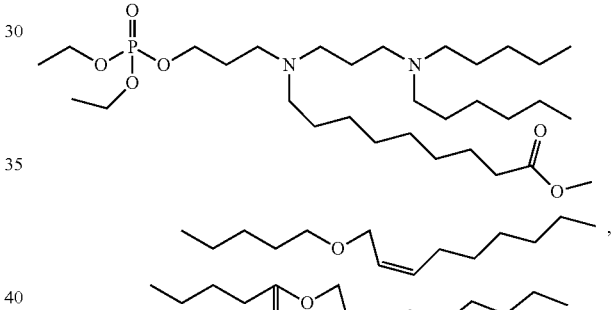
PL-17
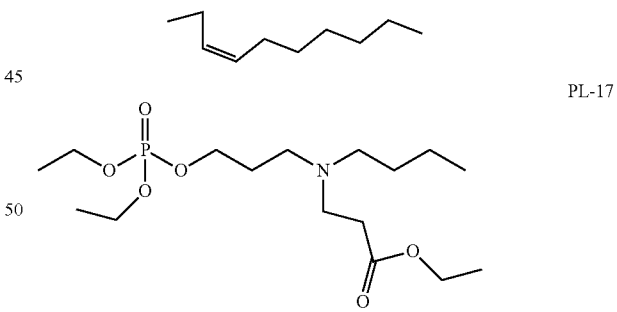
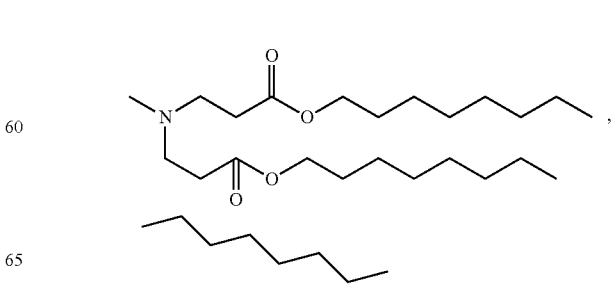

147
-continued
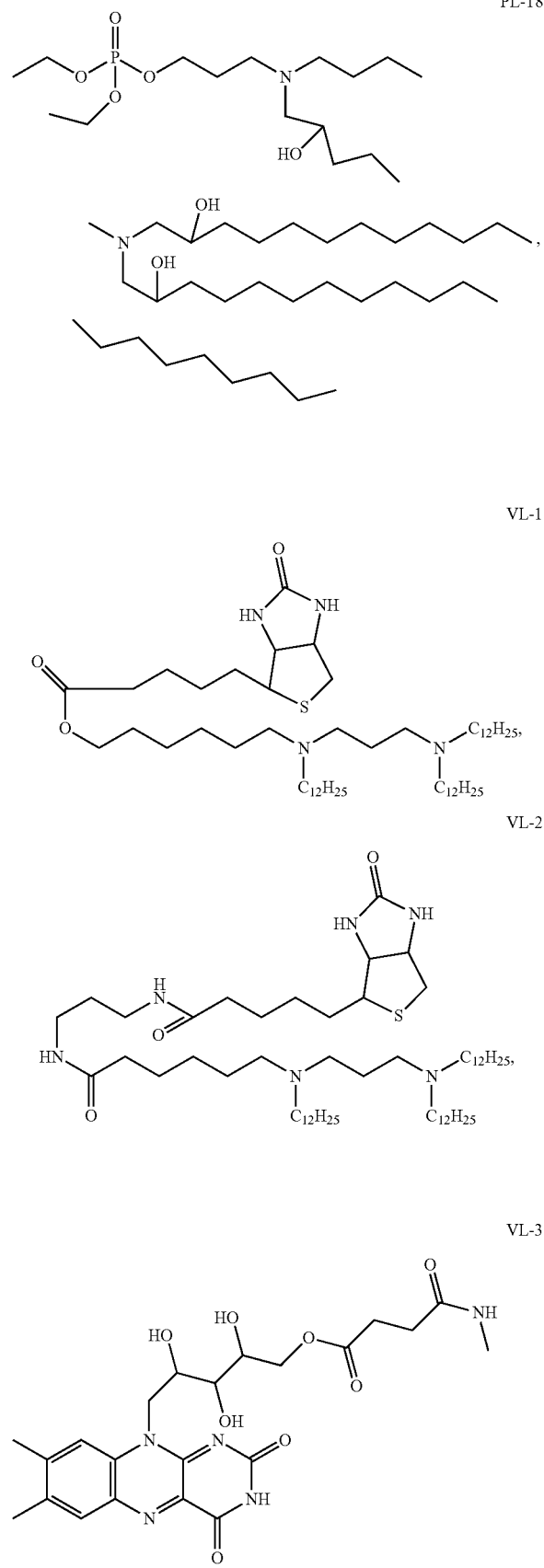
148
-continued
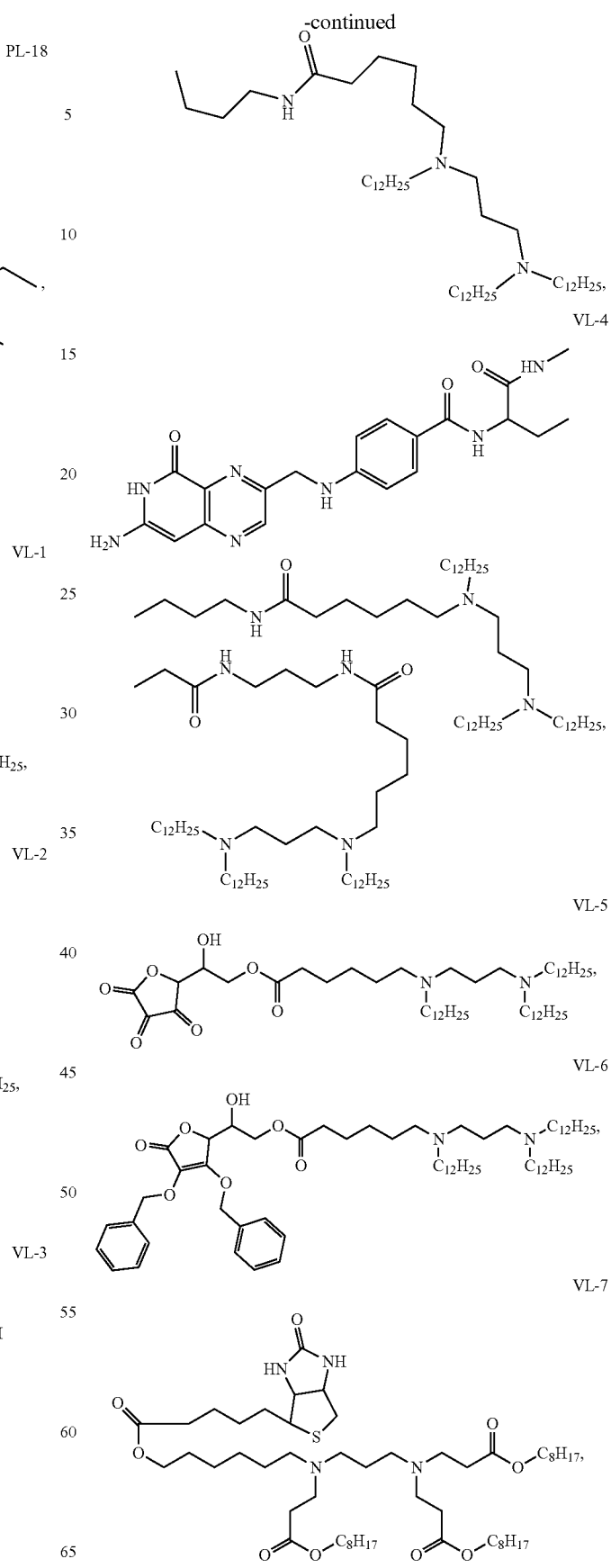

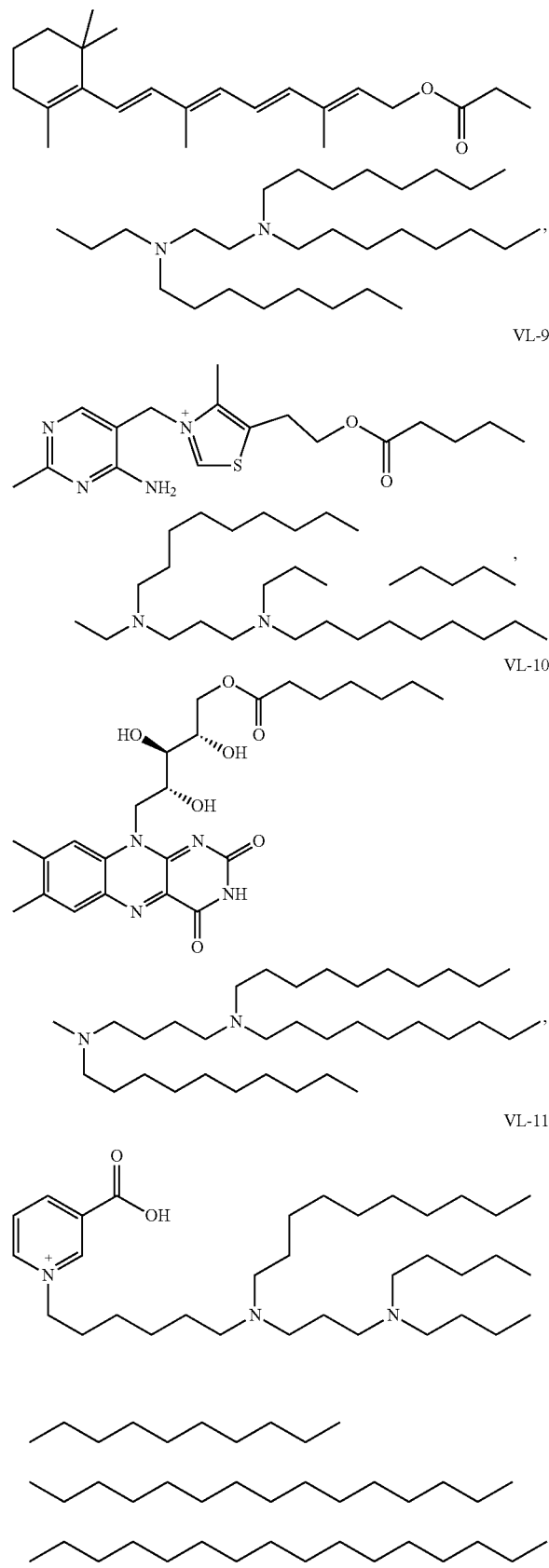
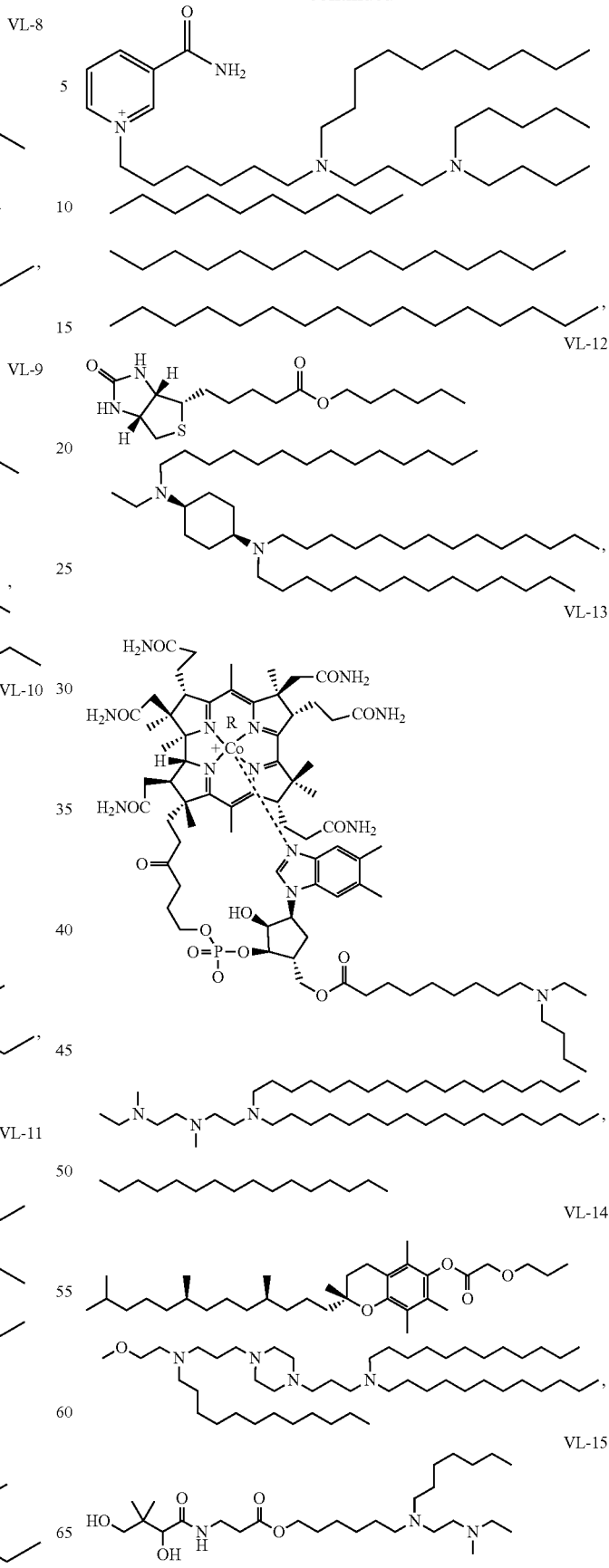

-continued
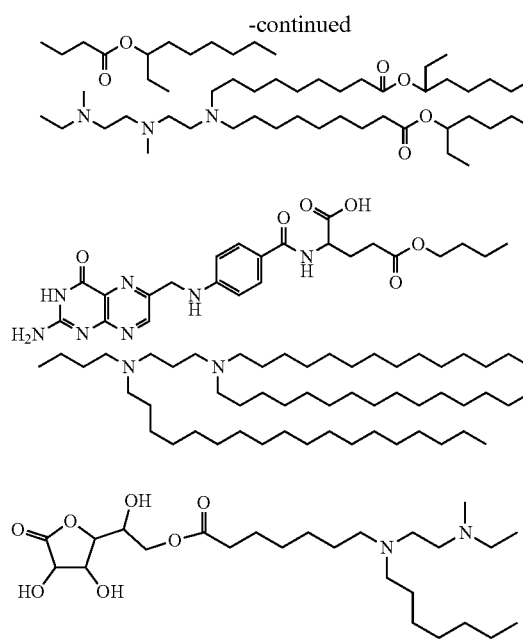
VL-16
VL-17
-continued
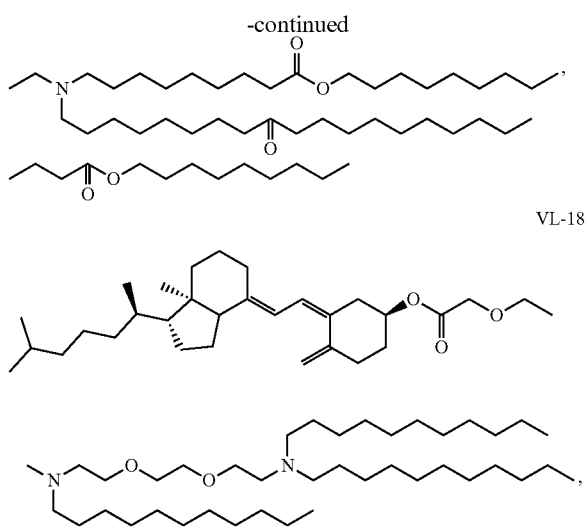
VL-18
or a salt thereof.
2. The compound of claim 1, wherein the compound is selected from the following:
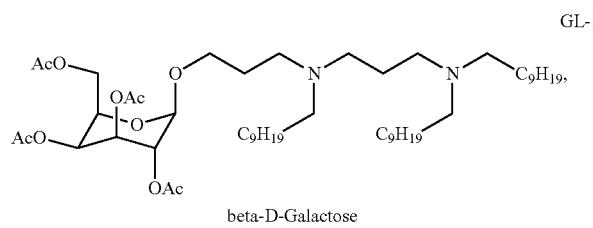
GL-1
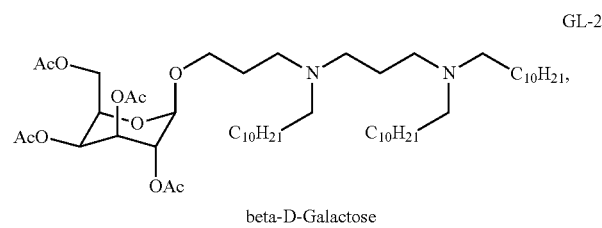
GL-2
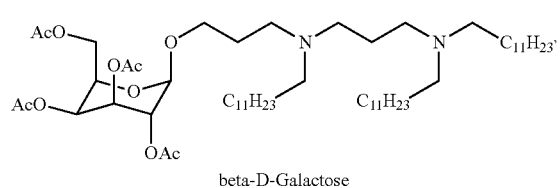
GL-3
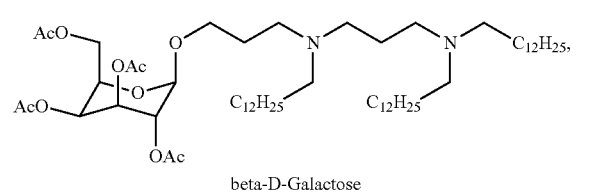
GL-4
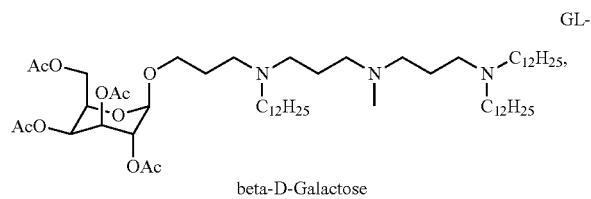
GL-5
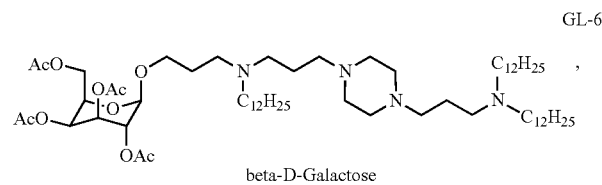
GL-6
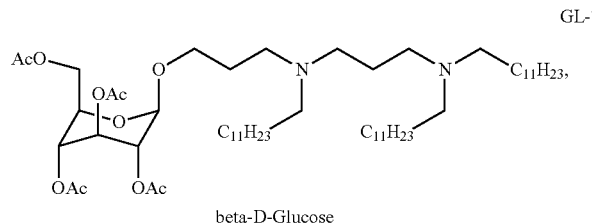
GL-7
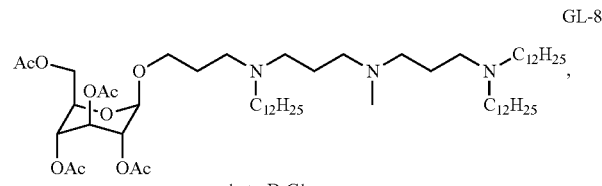
GL-8

-continued
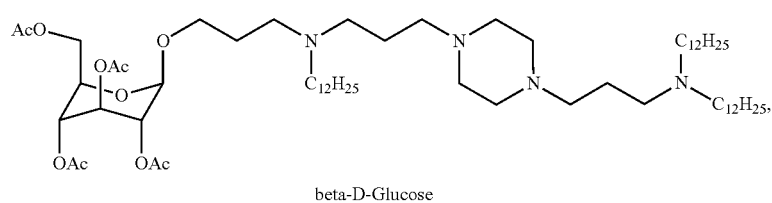
GL-9
beta-D-Glucose
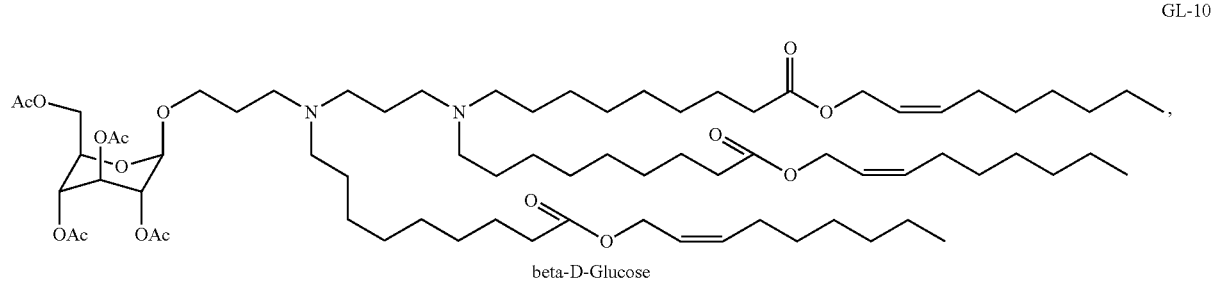
GL-10
beta-D-Glucose
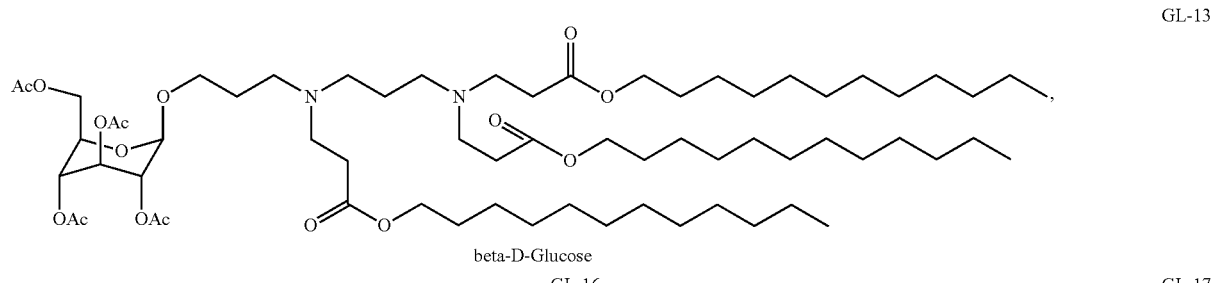
GL-13
beta-D-Glucose
GL-16
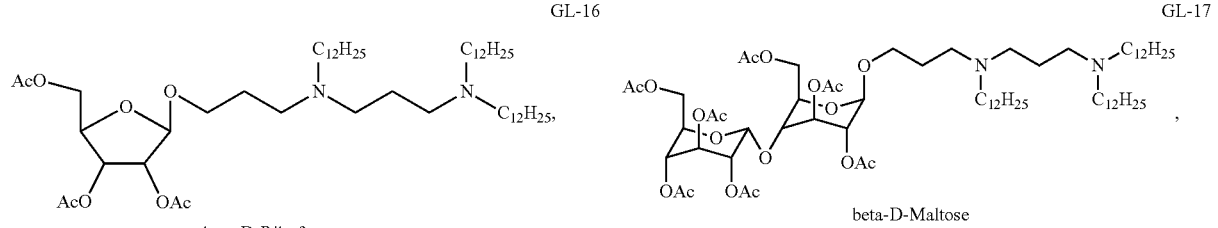
beta-D-Ribofuranose
GL-17
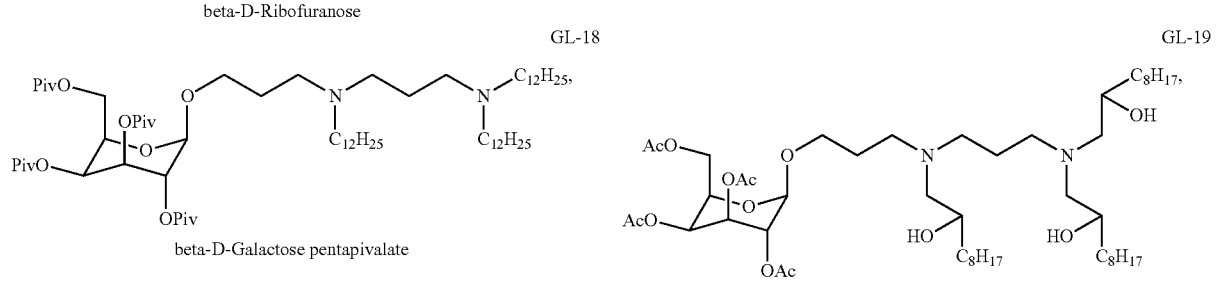
beta-D-Maltose
GL-18
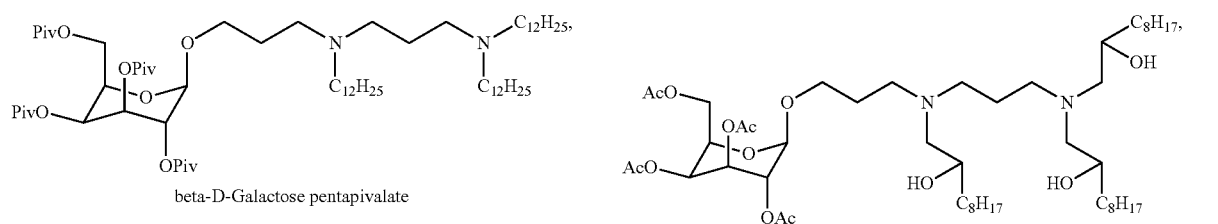
beta-D-Galactose pentapivalate
GL-19
3. The compound of claim 1, wherein the compound is selected from the following:
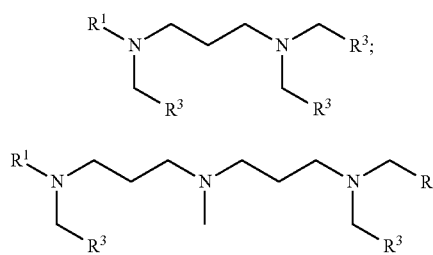
Formula I
Formula II
-continued
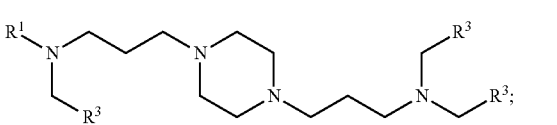
Formula III
Formula IV
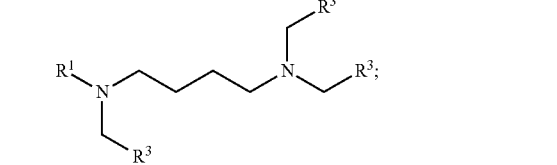

-continued
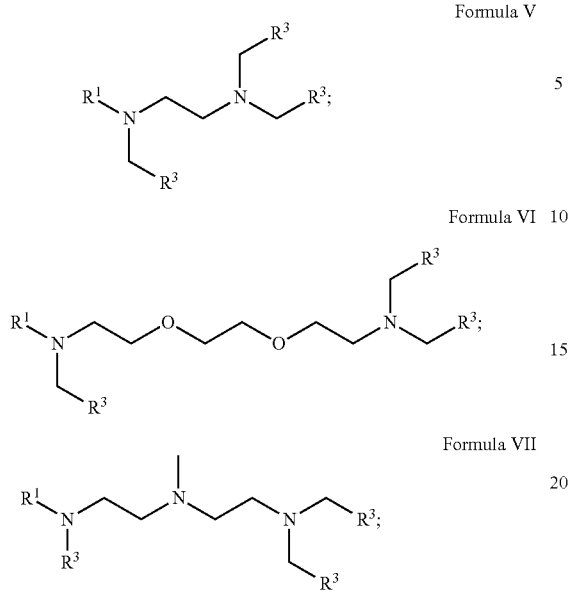
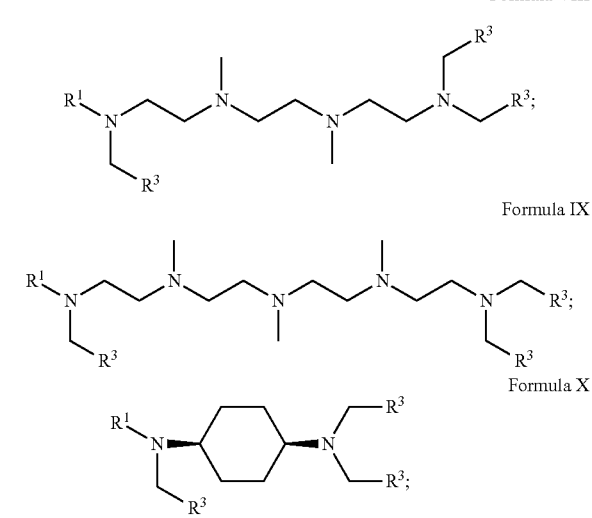
or a salt thereof.
4. The compound of claim 1, wherein the compound is selected from the following:
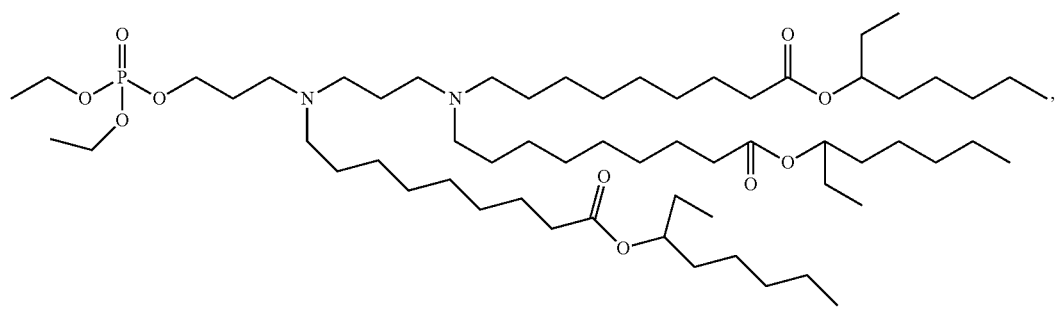
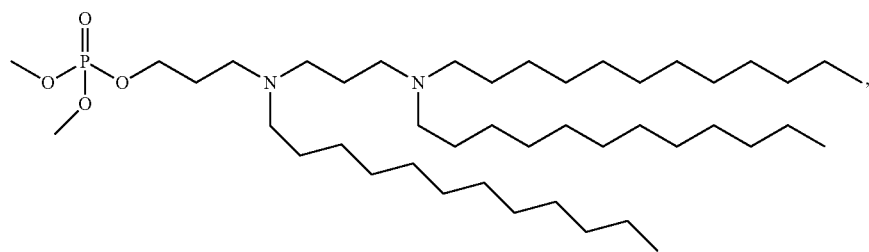
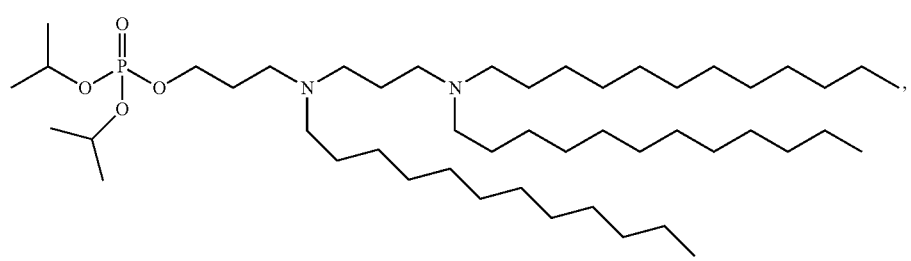

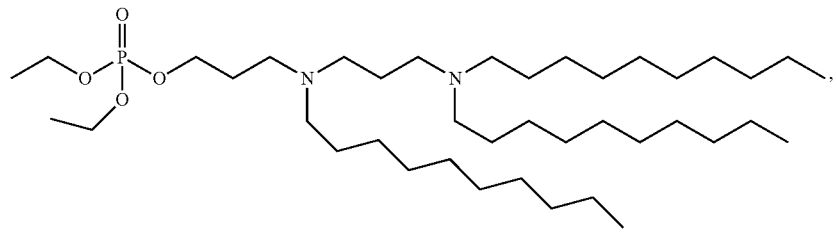
PL-4
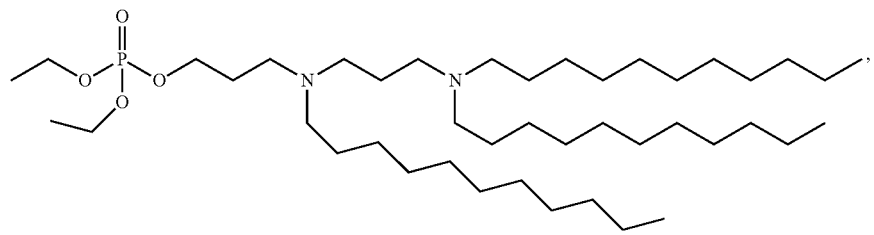
PL-5
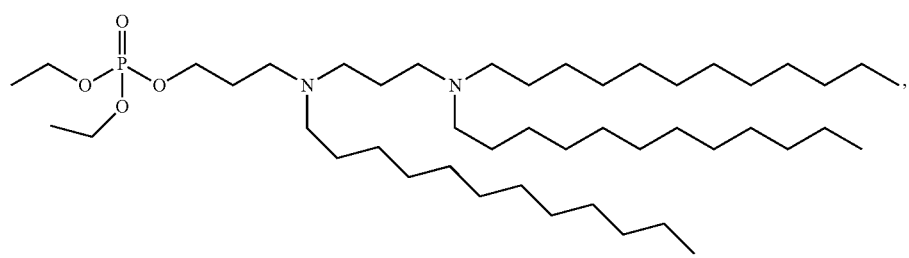
PL-6
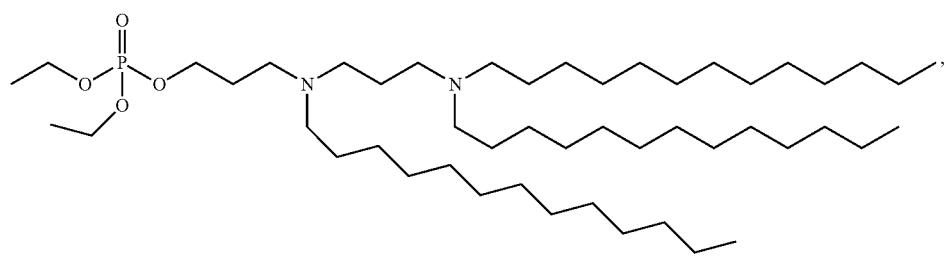
PL-7
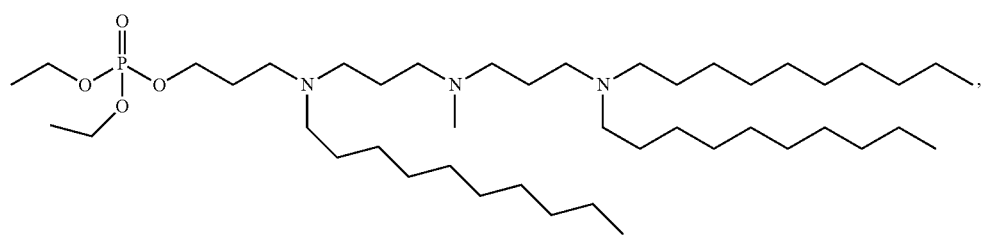
PL-8
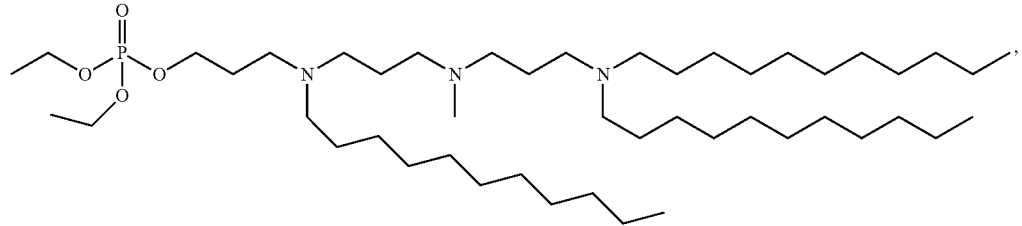
PL-9

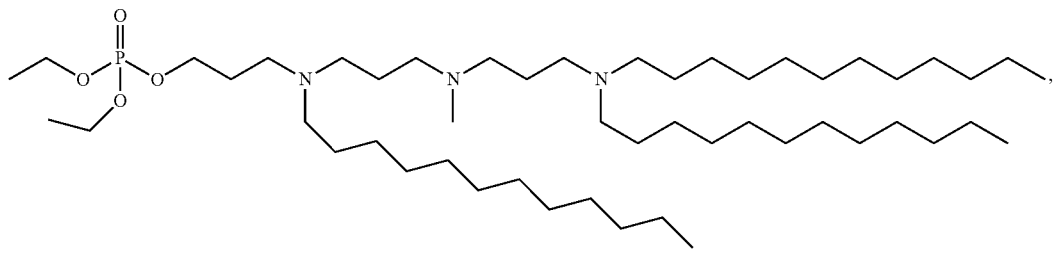
PL-10
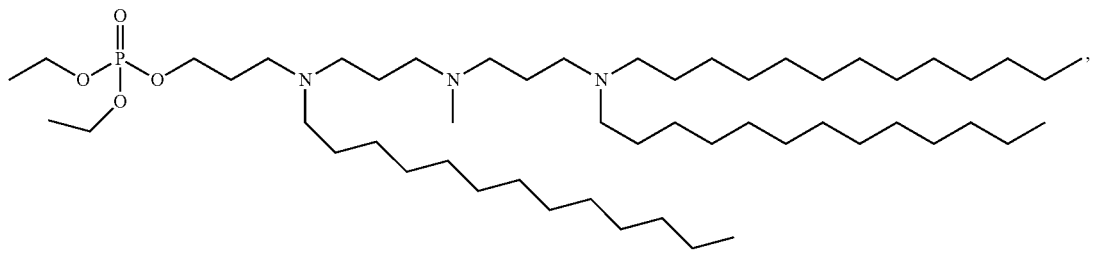
PL-11
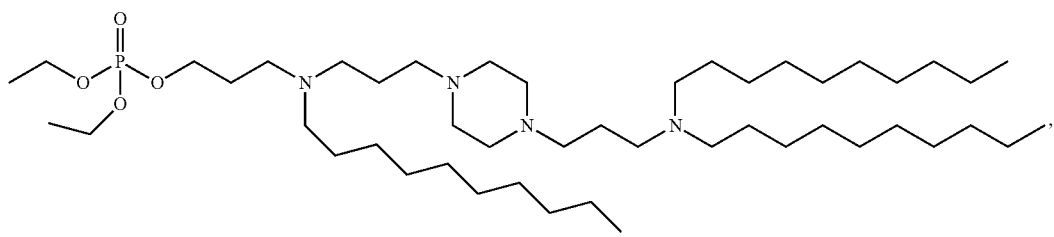
PL-12
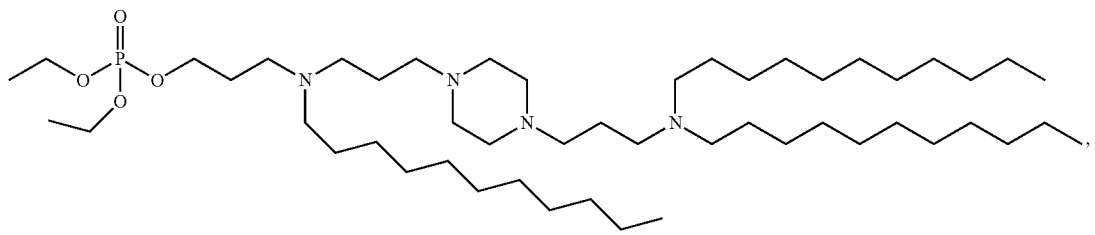
PL-13
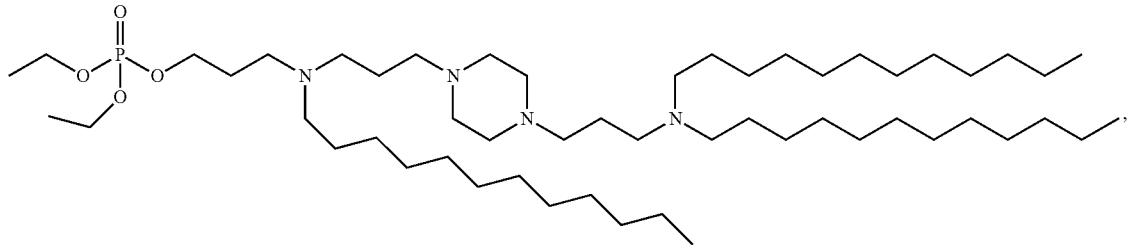
PL-14
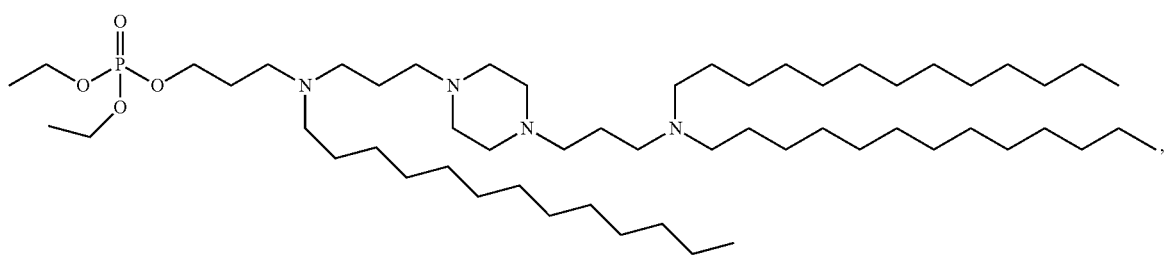
PL-15

PL-16
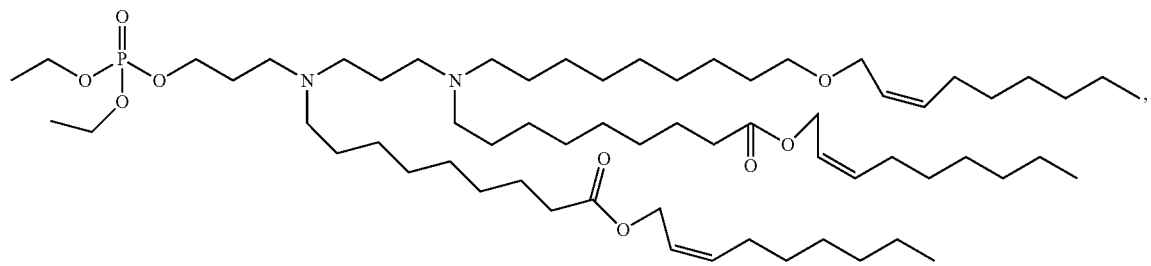
PL-17
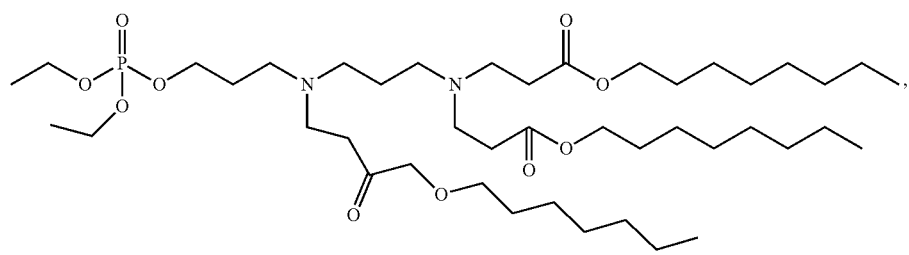
PL-18
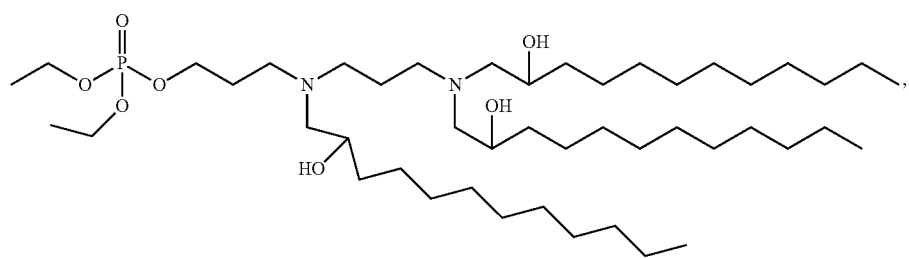
or a salt thereof.
5. The compound of claim 1, wherein the compound is selected from the following:
VL-1
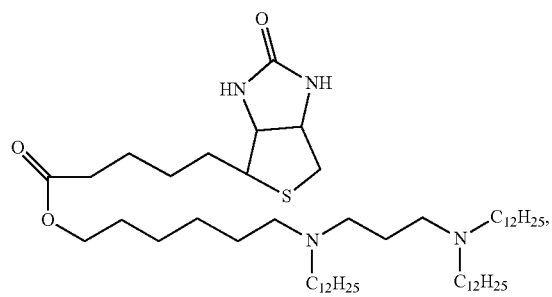
VL-2
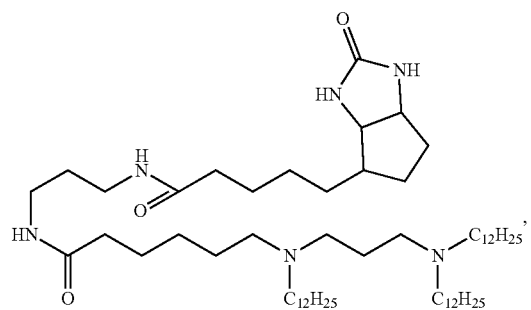
VL-3
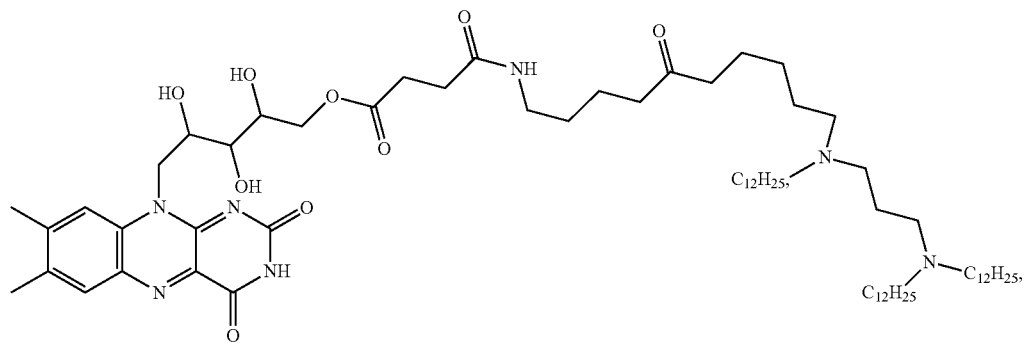

-continued
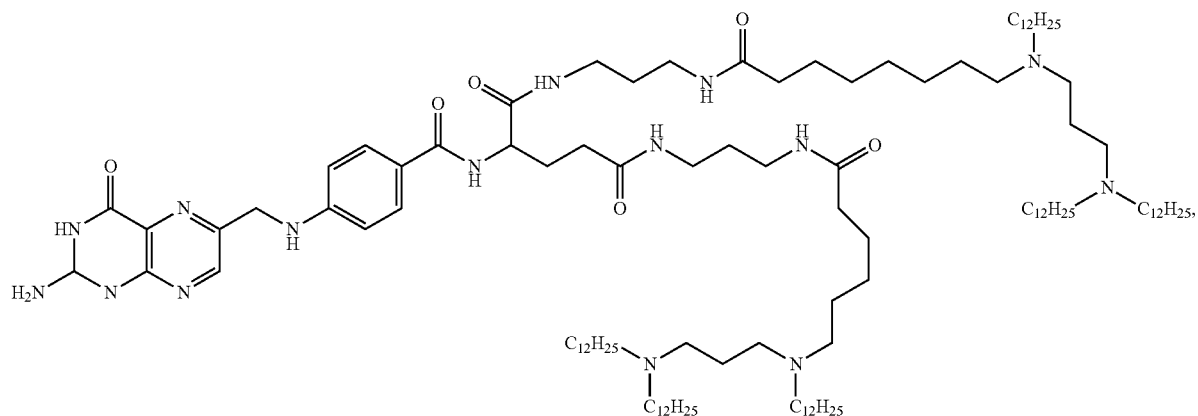
VL-4
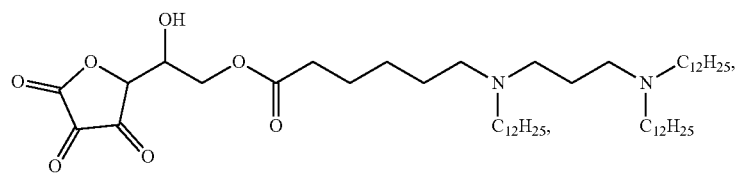
VL-5
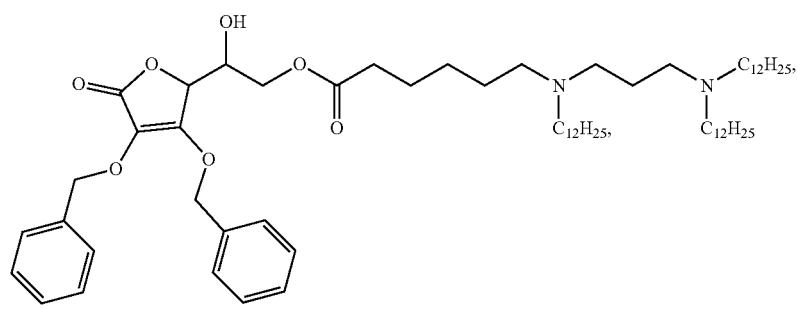
VL-6

VL-7
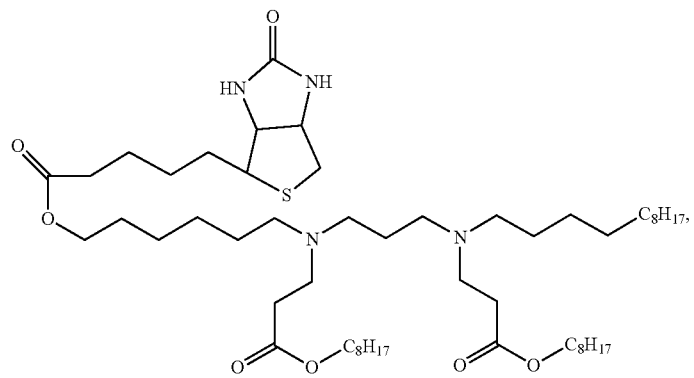
or a salt thereof.
6. The compound of claim 1, wherein the compound is selected from the following:
Vitamin A-lipid VL-8
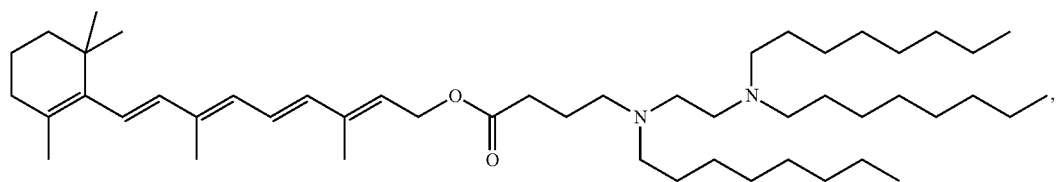
Vitamin B1-lipid VL-9
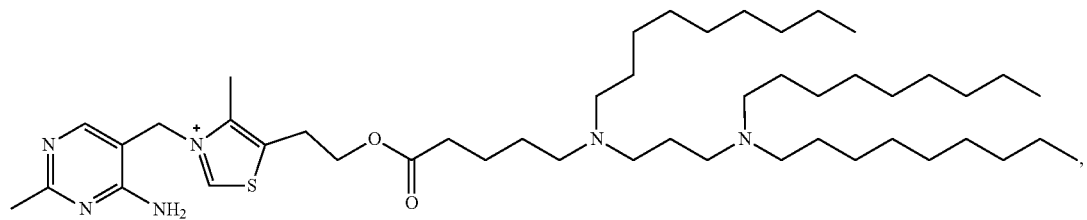
Vitamin B2-lipid VL-10
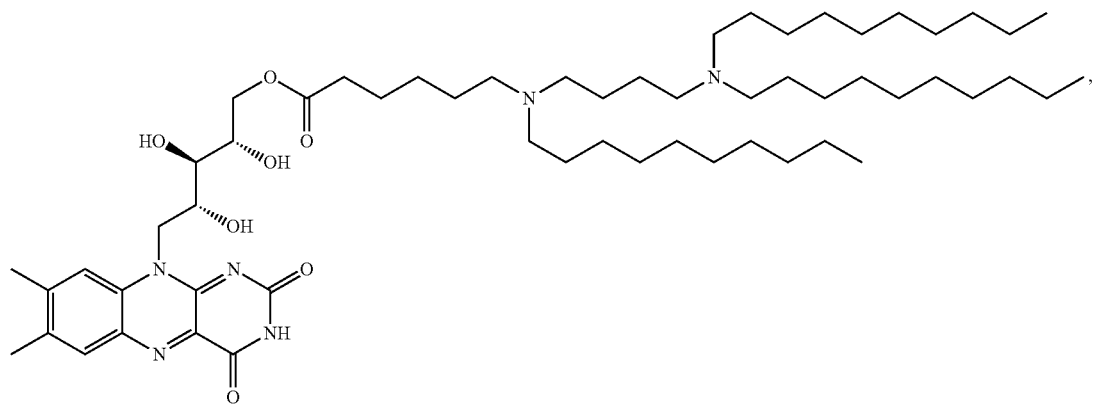

-continued
Vitamin B3-lipid VL-11
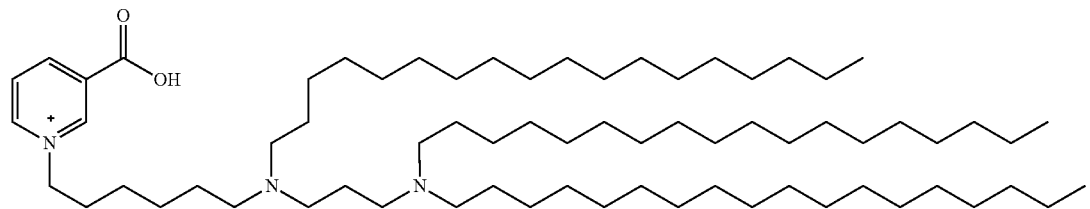
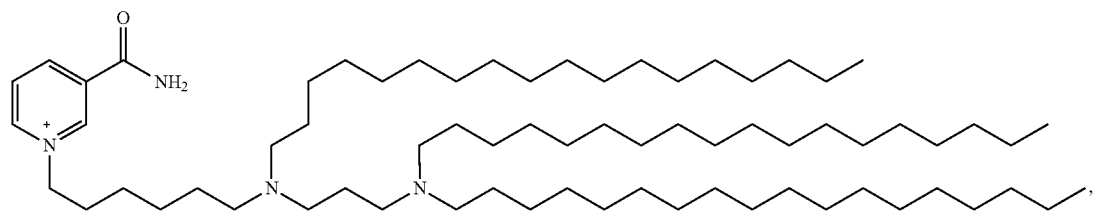
Vitamin B7-lipid VL-12
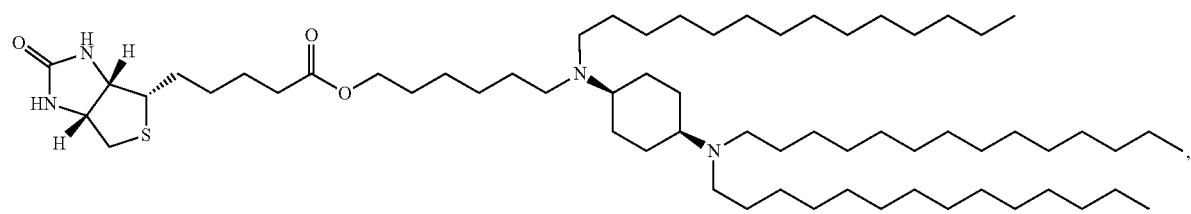
Vitamin B12-lipid VL-13
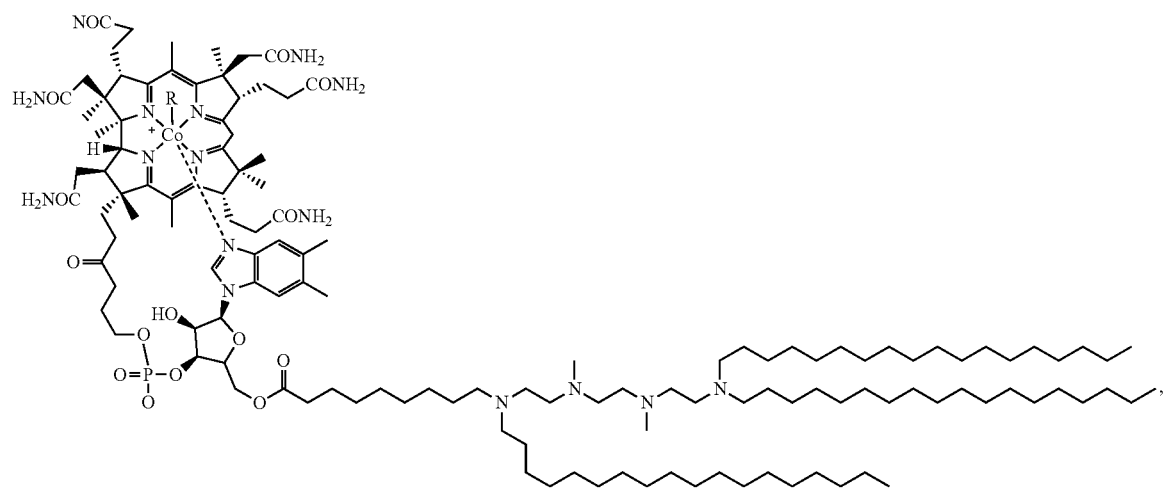
Vitamin E-lipid VL-14
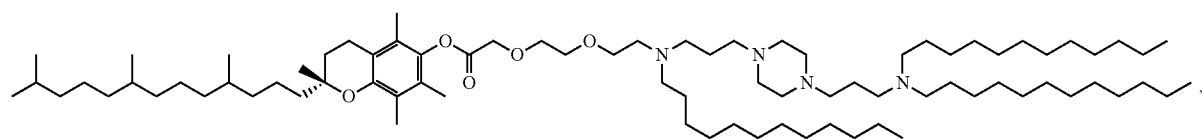
Vitamin B5-lipid VL-15
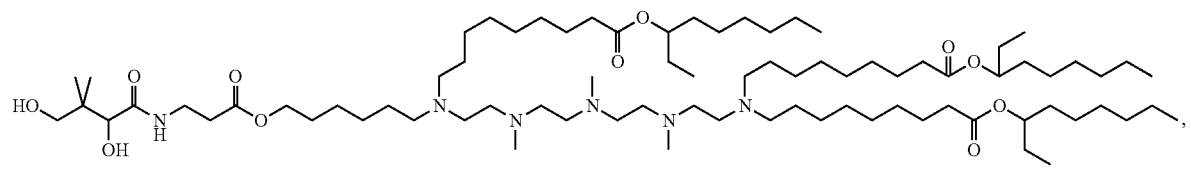

-continued

Vitamin B9-lipid VL-16

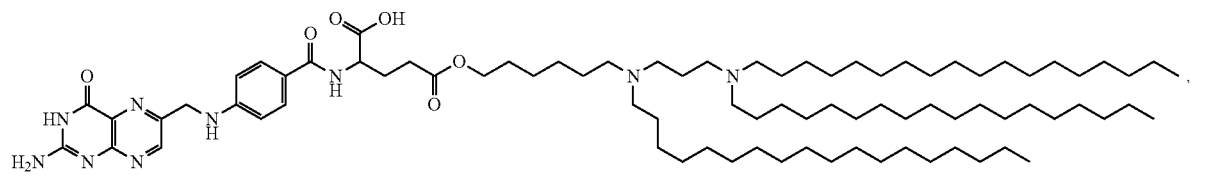

Vitamin C-lipid VL-17

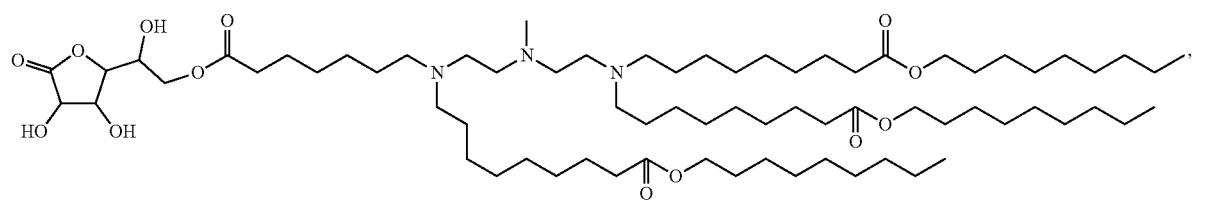

Vitamin D-lipid VL-18

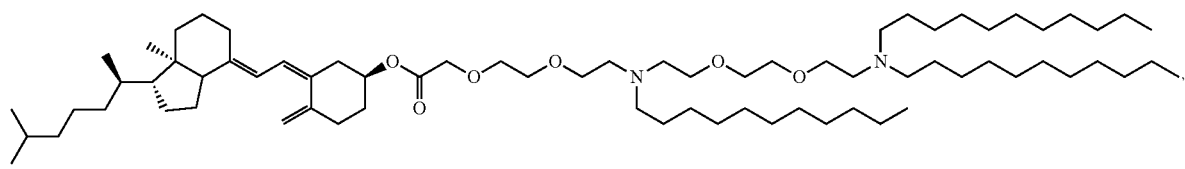

or a salt thereof.

7. A nanoparticle comprising:
the compound according to claim 1, or a salt thereof,
a non-cationic lipid;
a polyethylene glycol-lipid; and
a sterol.

8. A method for the delivery of an agent into a cell comprising;
introducing into the cell a composition comprising;
a nanoparticle comprising;
the compound according to claim 1, or a salt thereof;
a non-cationic lipid;
a polyethylene glycol-lipid; and
a sterol;
and
an agent.

9. The method of claim 8, wherein the agent is an mRNA.

* * * * *